(12) United States Patent
Potyrailo et al.

(10) Patent No.: US 11,971,399 B2
(45) Date of Patent: Apr. 30, 2024

(54) RESONANT SENSOR PROBE ASSEMBLY

(71) Applicant: Transportation IP Holdings, LLC, Norwalk, CT (US)

(72) Inventors: Radislav Alexandrovich Potyrailo, Niskayuna, NY (US); Craig Mack, Lisburn (GB); Christopher Calvert, Belfast (GB); Brian Scherer, Niskayuna, NY (US); James Schreiner, Erie, PA (US); Najeeb M. Kuzhiyil, Lawrence Park, PA (US); Subramani Adhiachari, Bangalore (IN); Partho Kayal, Bangalore (IN); Milan Karunaratne, Lawrence Park, PA (US); Nicholas E. Roddy, Schenectady, NY (US); Janaki Gadiyaram, Bangalore (IN); Steven Go, Schenectady, NY (US); Victor Manuel Salazar, Albany, NY (US)

(73) Assignee: TRANSPORTATION IP HOLDINGS, LLC, Norwalk, CT (US)

( * ) Notice: Subject to any disclaimer, the term of this patent is extended or adjusted under 35 U.S.C. 154(b) by 2 days.

(21) Appl. No.: 17/850,672

(22) Filed: Jun. 27, 2022

(65) Prior Publication Data
US 2022/0326212 A1 Oct. 13, 2022

Related U.S. Application Data

(63) Continuation-in-part of application No. 17/224,969, filed on Apr. 7, 2021, now Pat. No. 11,391,716, (Continued)

(51) Int. Cl.
| | |
|---|---|
| *G01M 15/09* | (2006.01) |
| *B61L 3/00* | (2006.01) |
| *G01N 27/02* | (2006.01) |
| *G01N 27/22* | (2006.01) |
| *G01N 33/28* | (2006.01) |

(52) U.S. Cl.
CPC .......... *G01N 33/2888* (2013.01); *B61L 3/002* (2013.01); *G01M 15/09* (2013.01); *G01N 27/026* (2013.01); *G01N 27/221* (2013.01); *G01N 33/28* (2013.01)

(58) Field of Classification Search
CPC ............. G01N 33/2888; G01N 27/026; G01N 27/221; G01M 15/09
See application file for complete search history.

(56) References Cited

U.S. PATENT DOCUMENTS

2010/0188111 A1* 7/2010 Fougere ............. G01N 33/2823
324/698
2017/0081997 A1* 3/2017 Potyrailo ............... F01M 11/12
(Continued)

*Primary Examiner* — Jamel E Williams
(74) *Attorney, Agent, or Firm* — Christopher R. Carroll; The Small Patent Law Group LLC

(57) ABSTRACT

A resonant sensor probe assembly includes a substrate formed from one or more dielectric materials and free-standing electrodes coupled with the substrate. The free-standing electrodes are configured to be placed into the fluid and to generate an electric field between the free-standing electrodes. A controller measures an impedance response of the sensor to the fluid between the electrodes to determine an aging effect of the sensor.

20 Claims, 34 Drawing Sheets

Related U.S. Application Data which is a continuation of application No. 16/146,322, filed on Sep. 28, 2018, now Pat. No. 10,996,210.

(60) Provisional application No. 62/612,855, filed on Jan. 2, 2018.

(56) References Cited

U.S. PATENT DOCUMENTS

2017/0138922 A1* 5/2017 Potyrailo ........... G01N 33/2888
2017/0363555 A1* 12/2017 Potyrailo ........... G01N 33/2888

* cited by examiner

RESONANT SENSOR PROBE ASSEMBLY

CROSS-REFERENCE TO RELATED APPLICATIONS

This application is a continuation-in-part of U.S. patent application Ser. No. 17/224,969, filed 7 Apr. 2021, which is a continuation of U.S. patent application Ser. No. 16/146,322, filed 28 Sep. 2018, which claims priority to U.S. Provisional Application No. 62/612,855, filed 2 Jan. 2018. The entire disclosures of these applications are incorporated herein by reference.

BACKGROUND

Technical Field

Embodiments of the subject matter disclosed herein generally relate to sensor probe assemblies that monitor and evaluate an operational condition of oil in various environments, such as when oil is utilized as a lubricant in engines, gearboxes, or generators, or as an electrical isolator in electrical transformers. Not all embodiments of the subject matter described herein, however, are limited to monitoring and evaluating the operational condition of oil in engines, gearboxes, or transformers.

Discussion of Art

Real time monitoring and evaluation of operational condition of engine or gearbox lubricating oil can be important for various applications such as vehicles (e.g., locomotives, marine vessels, automobiles, and others), and wind turbine gearboxes where early detection of engine or gearbox lubricating oil degradation, oil aging, and/or leaks of other fluids into the oil. Some known sensors measure and evaluate various aspects of the oil operating condition including mechanical resonating sensors (such as tuning forks and acoustic wave devices), capacitive sensors, conductometric sensors, sensor arrays, dielectric spectroscopy sensors, and complex permittivity sensors. These sensors have several limitations, such as low sensitivity and little to no resolution between different effects on oil. These limitations can prevent use of the sensors for early diagnosis of leaks of process fluids into engine oil.

Dissolved gas analysis (DGA) of isolating transformer oil is used for diagnostic measurements of transformer health and prognosis. Additionally, monitoring substation transformer health via DGA of the insulating oil is important for predicting potentially catastrophic faults and failures. Concentrations of dissolved gases in oil are measured at the part-per-million (ppm) level, with target gases such as hydrogen $H_2$, carbon monoxide CO, carbon dioxide $CO_2$, methane $CH_4$, acetylene $C_2H_2$, ethylene $C_2H_4$, ethane $C_2H_6$, or the like. Current DGA systems use a method to extract gas from oil (e.g. headspace or membrane) and then measure in the gas phase to infer the ppm concentration in oil. Examples of existing technologies for the gas determination and sensing are gas chromatography and infrared spectroscopy. To selectively measure the required fault gases, the extraction and gas sensor components can be expensive and complex, have many moving parts, can have a wide range of failure modes or performance challenges, or the like. If conventional sensors are used in DGA systems, these sensors exhibit drift over time. Such drift prevents the use of these sensors for accurate DGA determinations in long term applications.

BRIEF DESCRIPTION

In one embodiment, a resonant sensor probe assembly is provided that includes a dielectric substrate, free-standing electrodes, and a controller. The free-standing electrodes are coupled with the substrate. The controller may control generation of an electric field between the free-standing electrodes and determine an impedance response of the sensor probe assembly to a fluid between the electrodes responsive to generation of the electric field between the free-standing electrodes.

In one embodiment, a method is provided that includes forming a substate from one or more dielectric materials. The method includes coupling free-standing electrodes to the substrate and placing the free-standing electrodes to the substrate. The method includes generating an electric field between the free-standing electrodes and measuring an impedance response of a sensor probe assembly to the fluid between the free-standing electrodes in response to generation of the electric field between the free-standing electrodes.

In one embodiment, a method is provided that includes forming a substate from one or more dielectric materials a system and coupling free-standing electrodes to the substrate. The method includes placing the free-standing electrodes into a fluid and controlling generation of an electric field between the free-standing electrodes. The method includes determining an impedance response of a sensor probe assembly to the fluid between the free-standing electrodes responsive to generation of the electric field between the free-standing electrodes.

In one embodiment, a resonant sensor probe assembly includes a substrate formed from one or more dielectric materials and free-standing electrodes coupled with the substrate. The free-standing electrodes are configured to be placed into a fluid under examination, to generate an electric field between and in proximity to the free-standing electrodes, and to measure an impedance response of the sensor to the fluid between and in proximity to the electrodes. The fluid can be a gas or a liquid.

In one embodiment, a method includes monitoring previous operational conditions of an engine that operates using fuel and a lubricant, identifying one or more of an impurity content of the fuel supplied to the engine or an elapsed time since a previous addition of additional lubricant to the lubricant in the engine, and determining whether a change of the lubricant is required prior to continued operation of the engine based on the previous operational conditions and the one or more of the impurity content of the fuel or the elapsed time since the previous addition of the additional lubricant to the lubricant in the engine.

In one embodiment, a method includes measuring an electrical response of a sensing material in a gas sensor probe assembly while the gas sensor probe assembly is in an OFF state, determining an aging effect of the gas sensor probe assembly based on the electrical response of the sensing material in the gas sensor probe assembly while the gas sensor probe assembly is in the OFF state, measuring an electrical response of the sensing material in the gas sensor probe assembly while the sensing material is exposed to a fluid under examination and while the gas sensor probe assembly is in an ON state, and correcting the electrical response of the sensing material in the gas sensor probe assembly that is measured while the gas sensor probe assembly is in the ON state using the aging effect of the gas sensor probe assembly.

BRIEF DESCRIPTION OF THE DRAWINGS

The presently described subject matter will be better understood from reading the following description of non-limiting embodiments, with reference to the attached drawings, wherein below.

DETAILED DESCRIPTION

Figure 1:
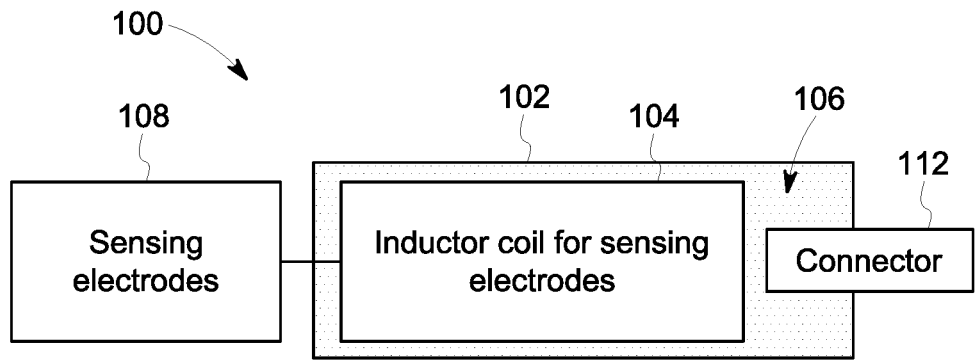
FIG. 1 illustrates a top view of one embodiment of a sensor probe assembly.

Some oil sensors are based on an inductor-capacitor-resistor (LCR) resonator structure that monitors aspects of oil operational conditions, such as levels of oil degradation and levels of external contaminants into oil. The LCR resonator operates in a multivariable mode where multiple outputs from the resonator are measured and used to detect independent changes in the oil operational conditions due to the leaks of water and fuel into the oil, and oil aging.

These types of sensors can involve a sensor probe comprised of two distinct components such as a sensing substrate onto which an electrode structure was deposited. The sensor probe may be a region of the sensor that is in operational contact with the measured industrial fluid (e.g., oil). Other portions of the sensor (such as sensor housing, transformer, electronics, electrical connectors, etc.) may not be in operational contact with the measured industrial fluid. The sensing substrate may be an inert material that allows the sensing electrodes to be presented to the fluid.

The sensing electrodes may be deposited only on one side of the substrate. This type of design may have significant limitations. First, the need for a substrate may not allow the entire surface of the electrodes to be in contact with the fluid under examination. Second, the substrate material can add a significant parasitic capacitance that reduces the sensitivity of the response of the sensor. Third, the substrate material can add a significant parasitic capacitance that reduces the selectivity of the response of the sensor to different constituents in the fluid under examination.

In one embodiment of the inventive subject matter described herein, a sensor probe assembly for monitoring of fluid (e.g., a gas or liquid, such as a lubricant) health and/or other industrial fluid health may have significant structural and manufacturing differences as compared to known sensor probes, and may have a significant improvement in sensor performance such as sensor sensitivity and sensor selectivity as compared to the known sensor probes. One structural difference in the design of the sensor probe assemblies described herein may be in the design of electrodes that does not require a sensor substrate. Since the electrodes may not require a sensor substrate, the electrodes may be considered free-standing. These free-standing electrodes may have a larger area that is in contact with the oil or fluid when compared to the electrodes of the same size of previous sensor probes that were deposited or otherwise mounted on substrates. Further, because the free-standing electrodes may not need to be physically coupled to the sensor substrate, the entirety of the free-standing electrode may be in contact with the oil or other industrial fluid being measured. The larger area can include a material that is sensitive to the presence of impurities in a fluid under examination. Examples of such materials may include metal oxide semiconductor materials, such as tin oxide ($SnO_2$), inorganic sorbing materials such as porous alumina, porous silicon, or polymeric sorbing materials such as poly[4,5-difluoro-2,2-bis(trifluoromethyl)-1,3-dioxole-co-tetrafluoroethylene] (Teflon AF) or poly[4,4'-oxydiphenylene-pyromellitimide] (Kapton), or another sensing material. These free-standing electrodes with or without sensing material may be a part of a resonant circuit of the sensor probe. Another structural difference in the design of the sensor probe assembly as compared to the known sensors may be that the electrodes have openings for an improved flow path of the measured oil or fluid across the electrodes. Another structural difference in the design of the sensor probe assembly as compared to the known sensors may be that the free-standing electrodes simultaneously serve as an inductor of the resonant sensor.

The sensor probe assembly can be manufactured using additive manufacturing (e.g., three-dimensional printing) and electrical discharge machining to produce the free-standing electrodes. The resonant components of a circuit of the sensor probe assembly also can be produced using additive manufacturing and electrical discharge machining. Electrical discharge machining may also be known as spark machining, spark eroding, burning, die sinking, wire burning, or wire erosion. This type of machining may create a desired shape using electrical discharges, such as sparks.

Figure 2:
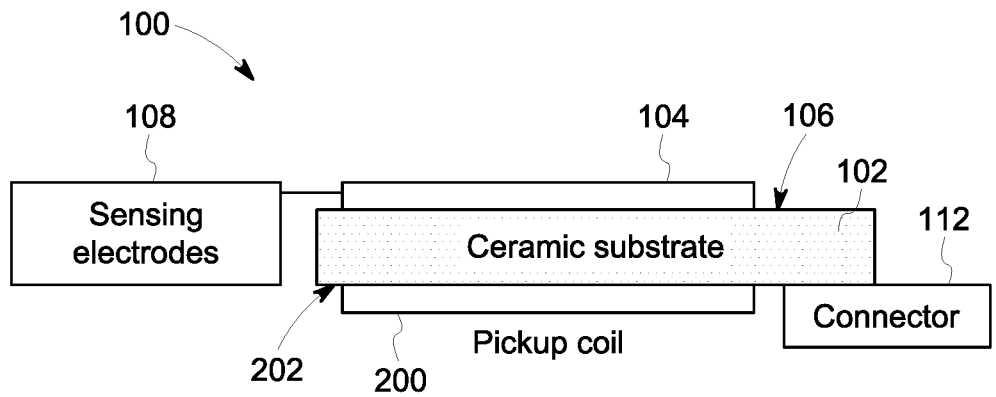
FIG. 2 illustrates a side view of the sensor probe assembly shown in FIG. 1.

FIG. 1 illustrates a top view of one embodiment of a sensor probe assembly 100. FIG. 2 illustrates a side view of the sensor probe assembly shown in FIG. 1. The sensor probe assembly can be included in a measurement system that measures the presence and/or amounts of one or more impurities or other compounds in a fluid of interest, such as oil or another lubricant. The sensor probe assembly may include a substrate 102 formed from a non-conductive material, such as one or more ceramic materials. The substrate can have a planar shape as shown in FIG. 2. A conductive inductor coil 104 may be mounted on one side 106 of the substrate and may be conductively coupled with one or more free-standing conductive electrodes 108. As shown in FIGS. 1 and 2, the electrodes may not be mounted on the substrate in that the electrodes may not be directly coupled with, may not directly engage, and may not abut any part or surface of the substrate. Moreover, the electrodes may not be above or below a footprint of the substrate, which may be defined by the surface area of the side of the substrate that extends upward and downward in the view of FIG. 2. A conductive pickup coil 200 may be coupled with the substrate on a side 202 of the substrate that may be opposite of the side to which the inductor coil is mounted. The inductor coil may be conductively coupled with one or more electronic connectors 112.

In operation, the sensor probe assembly may examine a fluid sample in contact with the electrodes for detection of one or more analytes of interest. The sensor probe assembly may detect characteristics or properties of the fluid via a resonant or non-resonant impedance spectral response of the material on the electrodes (not shown). One or more of the inductor-capacitor-resistor resonant circuits (LCR resonators) that may be at least partially formed by the electrodes and the inductor coil may measure the resonant impedance spectral response of a fluid under inspection. A non-resonant impedance spectral response may be measured when the circuit does not contain an inductor. The resonant or non-resonant impedance spectrum of the electrodes 108 in proximity to a fluid sample may vary based on sample composition and/or components. The measured resonant or non-resonant impedance values Z' (which may be the real part of resonant or non-resonant impedance, Zre) and Z" (which may be the imaginary part of resonant or non-resonant impedance, Zim) may reflect the response of the electrodes to the fluid. Optionally, an electrical field may be applied to a sensing material or film of the sensor probe assembly via the electrodes. The distance between the electrodes, may define the magnitude of the electric field. The electrodes may be in direct contact with the measured fluid. Alternatively, the electrodes may be in direct contact with the sensing material. For example, the sensing element may be a combination of a sensing region and associated circuits and/or the sensing region may be coated with the sensing material. The sensing material may be semiconductor material or metal oxide semiconductor material. The impedance values measured by the electrodes and/or coil can be inductively communicated through or across the substrate to the pickup coil, and can then be conducted to the connector to another system (e.g., data acquisition circuitry).

Data from the sensor probe assembly may be acquired via the data acquisition circuitry which may be connected with the assembly via the connector. The data acquisition circuitry can be connected with a controller or computer workstation where additional processing and analysis of the sensor data may be performed. The data can be indicative of the health of the fluid, the presence of contaminants within the fluid, and/or the age of the fluid.

Figure 3:
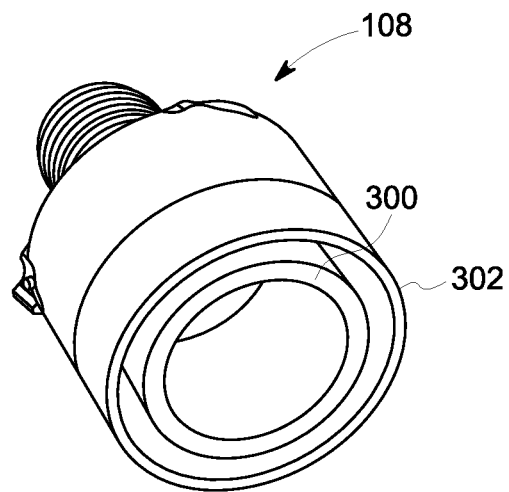
FIG. 3 illustrates a perspective view of an alternative embodiment of electrodes of the sensor probe assembly shown in FIGS. 1 and 2.
Figure 4:
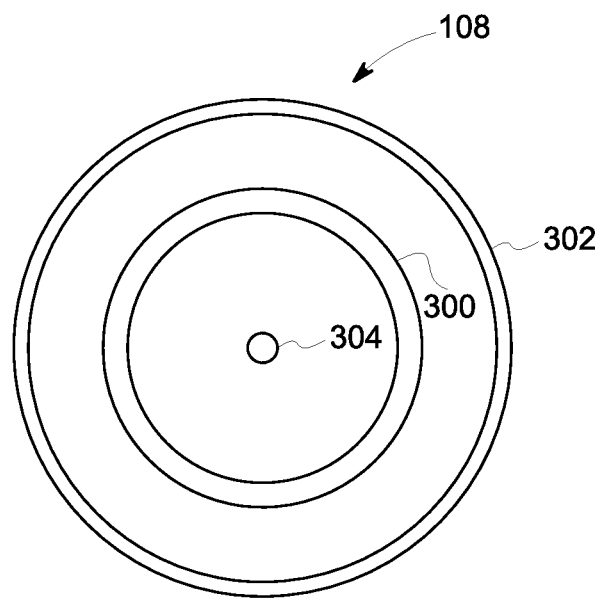
FIG. 4 illustrates an end view of the electrodes shown in FIG. 3.

FIG. 3 illustrates a perspective view of an alternative embodiment of the electrodes of the sensor probe assembly shown in FIGS. 1 and 2. FIG. 4 illustrates an end view of the electrodes shown in FIG. 3. In the illustrated embodiment, the electrodes may be arranged as coaxial tubes or circles 300, 302 that extend around and share a common center axis 304. The electrodes may be shaped as opposing plates that receive the fluid between the plates in FIGS. 1 and 2, but are tubes or circles in FIGS. 3 and 4. The electrode tubes or circles can be separated from each other by a radial gap so that the electrode tubes or circles may not be conductively coupled with each other off of or outside of the substrate. The electrode tubes or circles can be placed into the fluid under examination so that at least some of the fluid enters into the gap between the electrode tubes or circles. Although not shown in FIGS. 3 and 4, the electrodes can have sensing material (e.g., a metal oxide semiconductor) deposited thereon that may respond to the presence of one or more impurities of interest and an electric field generated by the electrodes.

Figure 5:
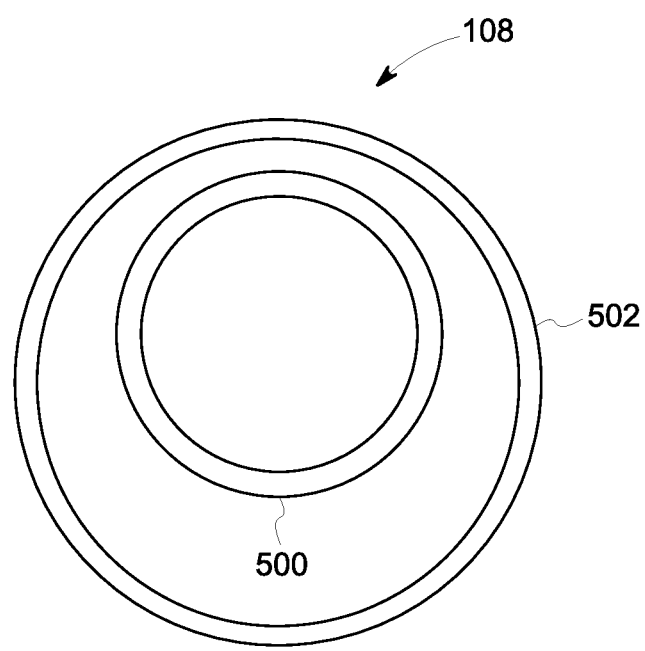
FIG. 5 illustrates an end view of an alternative embodiment of the electrodes of the sensor probe assembly shown in FIGS. 1 and 2.

FIG. 5 illustrates an end view of an alternative embodiment of the electrodes of the sensor probe assembly shown in FIGS. 1 and 2. In the illustrated embodiment, the electrodes may be arranged as non-coaxial tubes or circles 500, 502. The tube or circle 502 can extend around the tube or circle 500 without the tubes or circles having the same center axis. The electrode tubes or circles can be separated from each other by a gap so that the electrode tubes or circles are not conductively coupled with each other off of or outside of the substrate. The electrode tubes or circles can be placed into the fluid under examination so that at least some of the fluid enters into the gap between the electrode tubes or circles. Although not shown in FIG. 5, the electrodes can have sensing material (e.g., a metal oxide semiconductor) deposited thereon that responds to the presence of one or more impurities of interest and an electric field generated by the electrodes.

Figure 6:
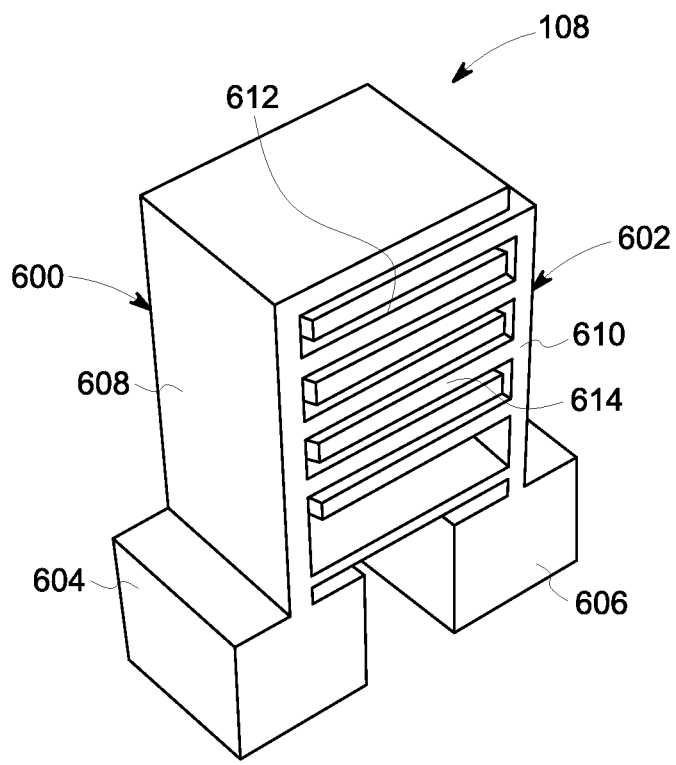
FIG. 6 illustrates a perspective view of another alternative embodiment of the electrodes of the sensor probe assembly shown in FIGS. 1 and 2.
Figure 7:
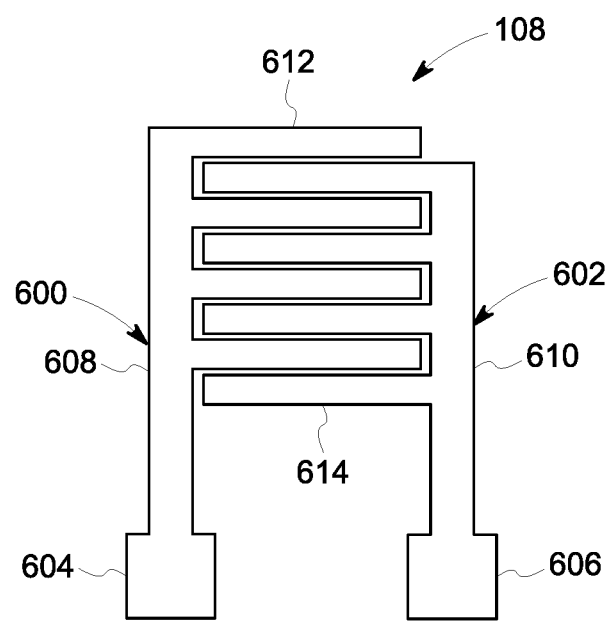
FIG. 7 illustrates a side view of embodiment of the electrodes shown in FIG. 6.
Figure 8:
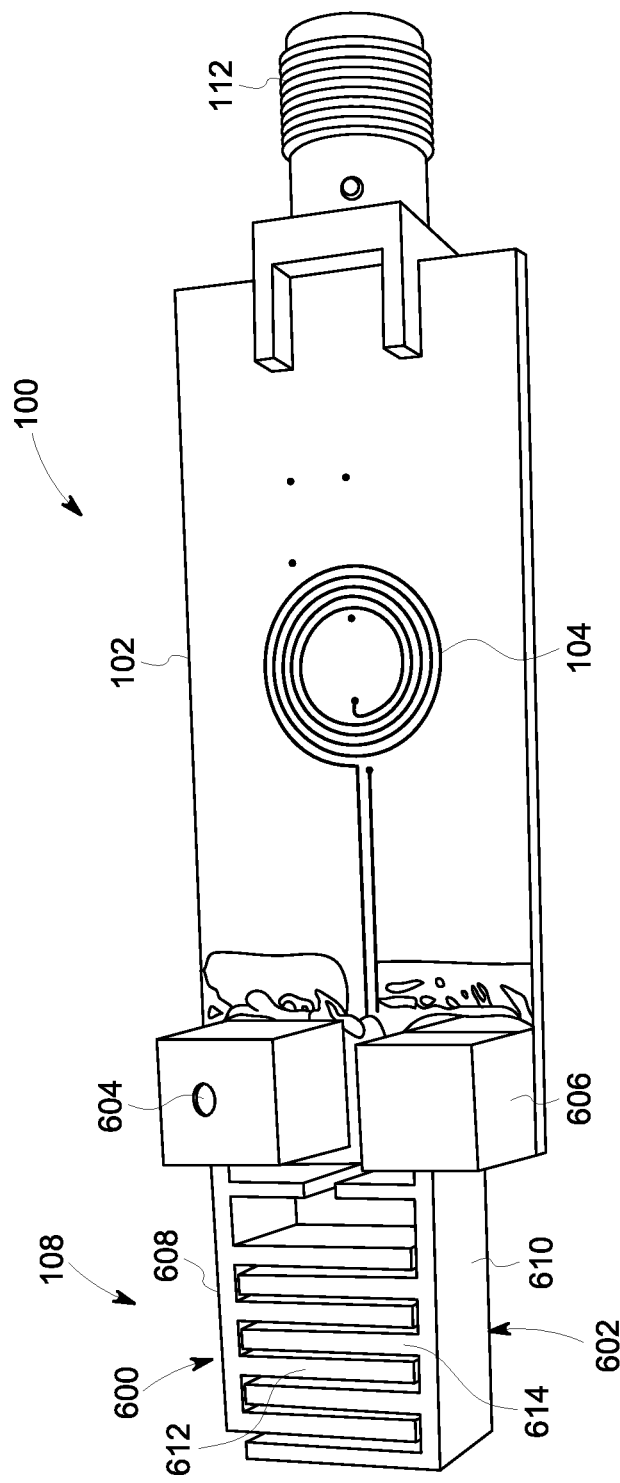
FIG. 8 illustrates the sensor probe assembly shown in FIG. 1 with the embodiment of the electrodes shown in FIGS. 6 and 7.

FIG. 6 illustrates a perspective view of another alternative embodiment of the electrodes of the sensor probe assembly shown in FIGS. 1 and 2. FIG. 7 illustrates a side view of embodiment of the electrodes shown in FIG. 6. FIG. 8 illustrates the sensor probe assembly shown in FIG. 1 with the embodiment of the electrodes shown in FIGS. 6 and 7. In the illustrated embodiment, the electrodes are arranged as interdigital electrodes 600, 602. The interdigital electrodes extend from different connecting ends 604, 606 that are separately coupled with the inductor coil shown in FIG. 1. The connecting ends are part of elongated connecting bars 608, 610 of the electrodes. The connecting bars are oriented parallel to each other. Although not shown in FIGS. 6 and 7, the electrodes can have sensing material (e.g., a metal oxide semiconductor, porous alumina oxide, porous silicon, polymer, zeolite, metal organic framework, or another material) deposited thereon that responds to the presence of one or more impurities of interest and an electric field generated by the electrodes.

The electrodes may include several elongated fingers 612, 614 that may be coupled with a different one of the connecting bars and that may extend toward, but may not be coupled with, the other connecting bar. For example, the fingers may be coupled with the connecting bar and extend toward, but may not be coupled with and may not engage, the other connecting bar. Similarly, the fingers may be coupled with the connecting bar and may extend toward, but may not be coupled with and may not engage, the other connecting bar.

The electrode fingers may be oriented parallel to each other such that the electrode fingers may be spaced apart from the electrode fingers in directions that may be perpendicular to the directions in which the fingers are elongated and in directions that may be parallel to the directions in which the connecting bars may be elongated. The electrode fingers can be placed into the fluid under examination so that at least some of the fluid may enter into the gaps between the electrode fingers.

Figure 9:
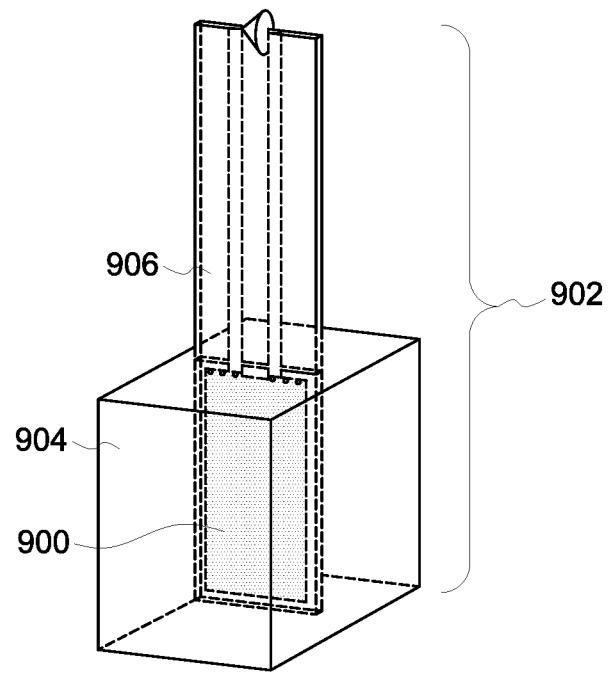
FIG. 9 illustrates partial submersion of electrodes of a known resonant sensor probe assembly into a fluid under examination.
Figure 10:
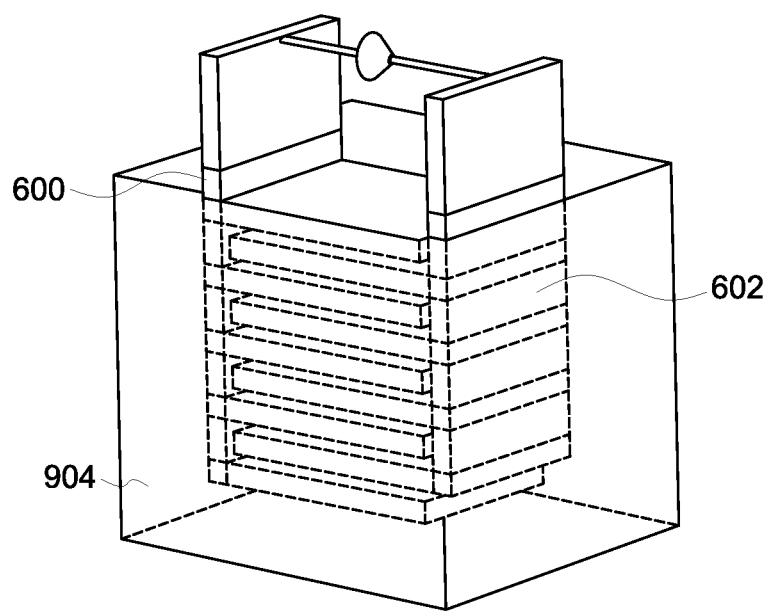
FIG. 10 illustrates partial submersion of the electrodes of the sensor probe assembly shown in FIGS. 6 through 8 into the fluid under examination.

Comparisons of sensitivities was done of a known resonant sensor probe assembly that use electrodes deposited on a substrate and one embodiment of the sensor probe assembly having interdigital free-standing electrodes. FIG. 9 illustrates submersion of electrodes 900 of a known resonant sensor probe assembly 902 into a fluid under examination 904 and FIG. 10 illustrates submersion of the electrodes of the sensor probe assembly shown in FIGS. 6 through 8 into the fluid under examination. The known probe assembly shown in FIG. 9 includes the electrodes being mounted or disposed upon a substrate 906. In contrast, the electrodes of the probe assembly shown in FIG. 10 are free-standing and are not mounted to any substrate.

As shown in the perspective view of the electrodes shown in FIGS. 6 and 10, the electrodes may be larger in three orthogonal directions (e.g., the x-, y-, and z-axes of the Cartesian coordinate system) than the electrodes that may be mounted on the substrate. The electrodes may have a more planar shape as these electrodes may be deposited onto the substrate in a thin layer. The electrodes may be larger in three dimensions than the electrodes.

Figure 11:
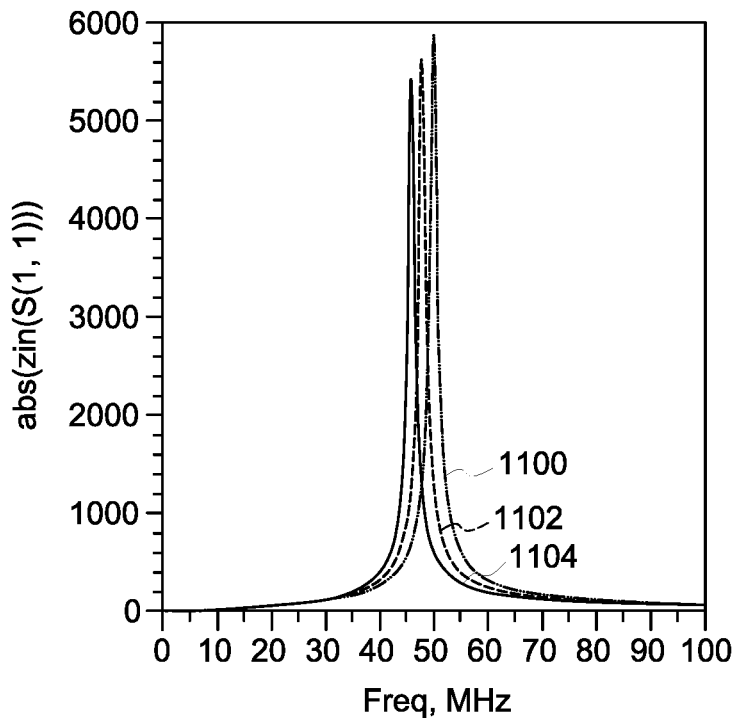
FIG. 11 illustrates resonant spectral responses of the sensor probe assembly with the free-standing electrodes in contact with oil having dielectric constants of 2.1, 2.3, and 2.5, respectively, according to one example.
Figure 12:
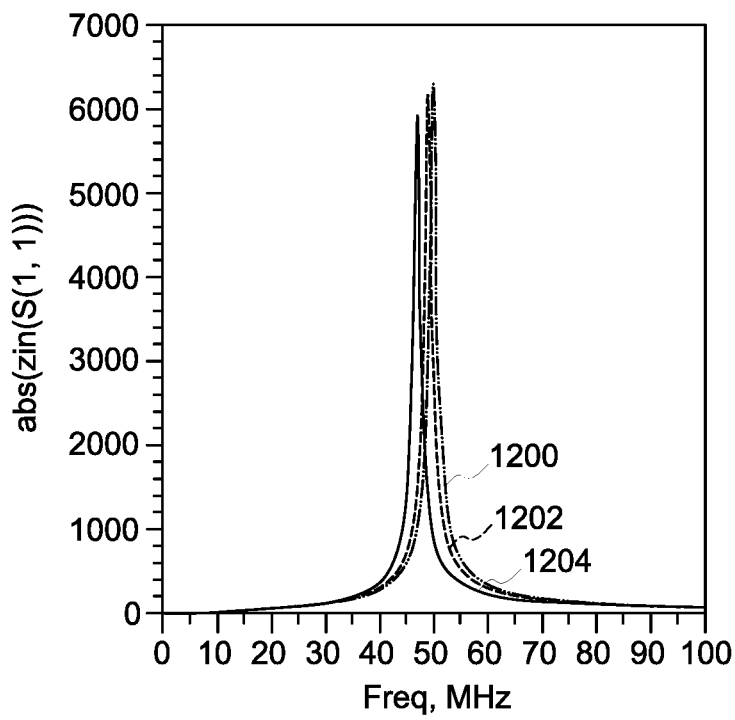
FIG. 12 illustrates resonant spectral responses of the sensor probe assembly with the non-free-standing electrodes deposited onto the substrate having a dielectric constant of one according to a first example.
Figure 13:
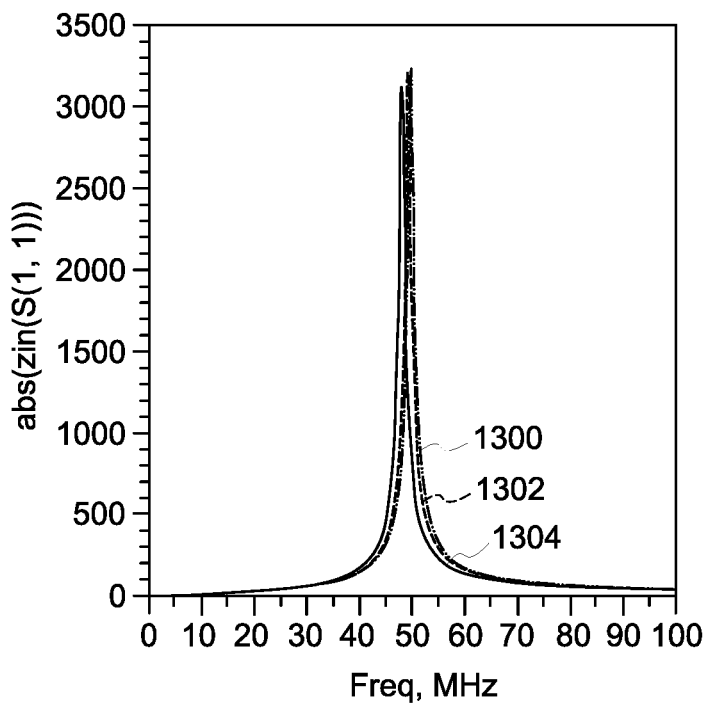
FIG. 13 illustrates resonant spectral responses of the sensor probe assembly with the non-free-standing electrodes deposited onto the substrate having a dielectric constant of 4.5 (e.g., FR4) according to a first example.
Figure 14:
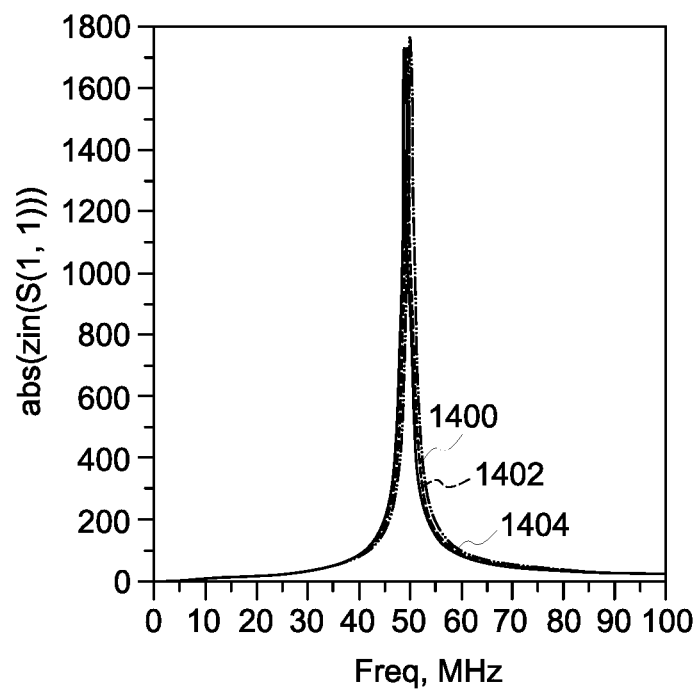
FIG. 14 illustrates resonant spectral responses of the sensor probe assembly with the non-free-standing electrodes deposited onto the substrate having a dielectric constant of 9.1 (e.g., alumina) according to a first example.

Three-dimensional electromagnetic modeling was used to determine the effects of the changes of the dielectric properties of the fluid surrounding sensing regions of the probe assemblies 902, 100 that include the electrodes 900, 600, 602 on the spectral responses of the two different types of the resonant sensor probe assemblies. FIG. 11 illustrates resonant spectral responses 1100, 1102, 1104 of the sensor probe assembly with the free-standing electrodes in contact with oil having dielectric constants of 2.1, 2.3, and 2.5, respectively, according to one example. FIG. 12 illustrates resonant spectral responses 1200, 1202, 1204 of the sensor probe assembly with the electrodes deposited onto the substrate having a dielectric constant of one according to a first example. FIG. 13 illustrates resonant spectral responses 1300, 1302, 1304 of the sensor probe assembly with the electrodes deposited onto the substrate having a dielectric constant of 4.5 (e.g., FR4) according to a first example. FIG. 14 illustrates resonant spectral responses 1400, 1402, 1404 of the sensor probe assembly with the electrodes deposited onto the substrate having a dielectric constant of 9.1 (e.g., alumina) according to a first example. The spectral responses shown in FIGS. 11 through 14 are shown alongside horizontal axes representative of frequencies and vertical axes representative of magnitudes of the resonant responses of the sensor probe assemblies to the oil.

Figure 15:
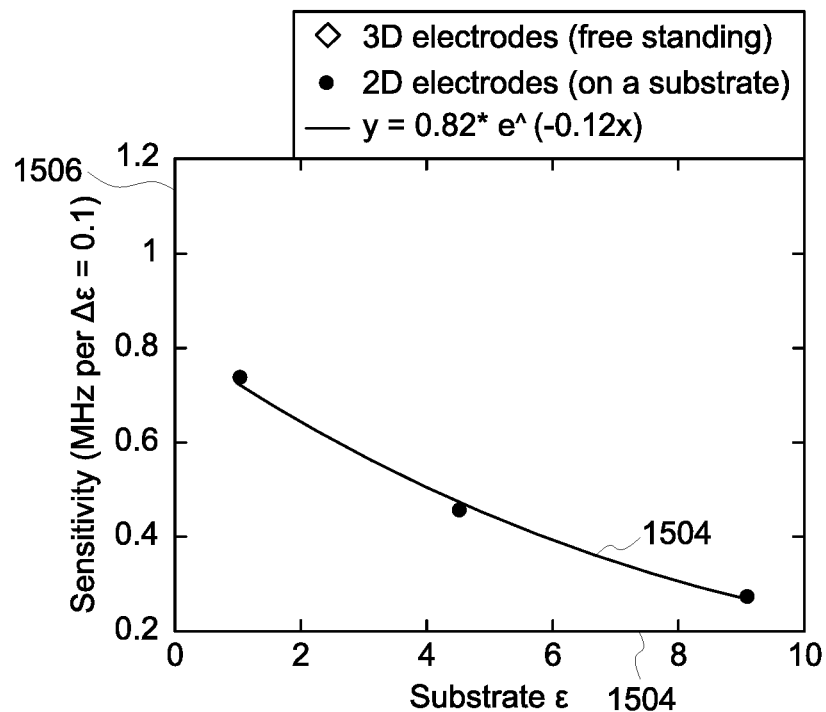
FIG. 15 illustrates a comparison of sensitivities of the sensor probe assemblies associated with the examples of FIGS. 11 through 14 according to one example.

FIG. 15 illustrates a comparison of sensitivities 1500, 1502 of the sensor probe assemblies associated with the examples of FIGS. 11 through 14 according to one example. The sensitivities may be shown alongside a horizontal axis 1504 representative of the dielectric constants of the surfaces on which the electrodes of the sensor probe assemblies are mounted and a vertical axis 1506 representative of how sensitive the spectral response of the corresponding sensor probe assemblies are to one or more components in the oil. The sensitivity represents the sensitivity of the probe assembly having the free-standing electrodes while the sensitivities represent the sensitivities of the probe assemblies having the substrate-mounted electrodes on the substrates with different dielectric constants.

As shown by a comparison of the spectral responses shown in FIGS. 11 through 14, the spectral responses of the sensor probe assembly with the free-standing electrodes may demonstrate larger spectral shifts than the spectral responses of the probe assemblies with the electrodes mounted on substrates. For example, the peaks of the spectral responses of the sensor probe assembly with the free-standing electrodes may be farther apart from each other (along the horizontal axis) than the peaks of the spectral responses of the sensor probe assembly with the substrate-mounted electrodes. This may indicate that the sensor probe assembly with the free-standing electrodes may be more sensitive to, and therefore more accurate in quantifying, the health and/or contents of the oil than the sensor probe assemblies with the substrate-mounted electrodes. For example, the spectral responses may indicate that the sensitivity of resonant sensor probe assemblies may decrease with increases in the dielectric constant of the electrode substrate. Additionally, the sensitivities in FIG. 15 may show that the sensitivity of the resonant sensor probe assembly with the free-standing electrodes may be significantly higher as compared to that of the sensor probe assembly with electrodes deposited onto a substrate.

When the electrodes are fabricated using additive manufacturing methods, auxiliary sensors may be embedded into the structure of the electrodes. For example, an auxiliary temperature sensor may be built together with the electrodes using 3D printing. The temperature sensor may be used for temperature compensation of the measured variables, for example water content in oil and/or oil aging such as total base number (TBN) or total acid number (TAN). The fabrication method of the electrodes may provide control of the fluid-electrode interface contact angle using electrodes with different morphology, surface finishing and materials with the aim of achieving wetting for a wide range of operating conditions and oils that feature different viscosities and compositions.

When electrodes are fabricated using additive manufacturing methods, the electrodes may be fabricated using more than one material to provide more than one functionality for the sensor. Multi-material 3D printing of electrodes may be done where one or more printed materials are magnetic for detection of metal particles while other printed materials are for detection of other properties such as water content and/or TBN, TAN of the fluid media.

In operation, the electrode structure may be protected with a shield. The shield may be designed to have several functions such as to protect electrodes from mechanical damage, to control flow through the sensing element to allow the sensing electrodes to be fully wetted by the measured fluid, and to control air bubble contact with sensing electrodes, where the openings of the shield may be designed to trap and prevent bubbles to reach the sensing electrodes.

In one embodiment, a resonant sensor probe assembly may include a substrate formed from one or more dielectric materials and free-standing electrodes coupled with the substrate. The free-standing electrodes may be placed into a fluid under examination, may generate an electric field between the free-standing electrodes, and may measure an impedance response of the sensor to the fluid between the electrodes.

Optionally, the free-standing electrodes may not be directly mounted on the substrate.

Optionally, the free-standing electrodes may not be disposed within a footprint of the substrate.

Optionally, the free-standing electrodes may be placed into the fluid and may measure the impedance response of the sensor to the fluid without the substrate being placed into the fluid.

Optionally, the free-standing electrodes may include opposing planar plates positioned to receive at least some of the fluid between the plates.

Optionally, the free-standing electrodes may include an inner tube electrode disposed within and spaced apart from an outer tube electrode.

Optionally, the inner and outer tube electrodes may be concentric tubes.

Optionally, the free-standing electrodes may include opposing supporting bars with elongated, interdigital electrode fingers.

Figure 16:
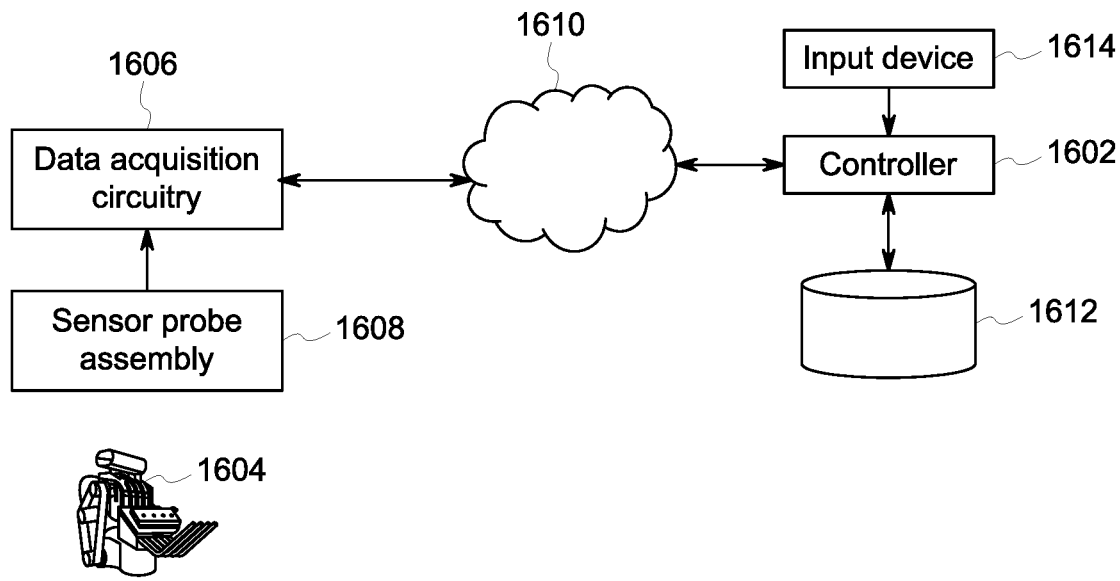
FIG. 16 illustrates one embodiment of a maintenance system.

One example of use of one or more of the sensor probe assemblies described herein (including the assemblies with the free-standing electrodes or the assemblies with the electrodes mounted to substrates) may be to measure and quantify the health of engine lubricant, such as oil. FIG. 16 illustrates one embodiment of a maintenance system 1600. The maintenance system may include a controller 1602 that obtains data from plural different and/or remotely located components and uses the data to create and/or update a model (e.g., digital twin) of equipment 1604. The controller optionally can use the model to determine when the equipment (e.g., an engine of a stationary or mobile power-generating machine) needs to have a lubricant (e.g., oil) in the equipment changed or otherwise replaced. The controller may represent hardware circuitry that includes and/or is coupled with one or more processors (e.g., one or more microprocessors, field-programmable gate arrays, integrated circuits, or the like) that perform the operations described herein.

The controller obtains measurements of contaminants and other contents of the lubricant from data acquisition circuitry 1606 that receives these measurements from one or more sensor probe assemblies 1608. The sensor probe assemblies may represent one or more of the sensor probe assemblies described herein. The data acquisition circuitry may represent one or more computing hardware systems, such as computers, input devices, or the like, that obtain the measurements of the lubricant as created by the sensor probe assemblies. Because the data acquisition circuitry and/or sensor probe assemblies may be remotely located from the controller (e.g., not in the same room, building, ZIP code, state, or the like), the data acquisition circuitry can communicate the measurements from the sensor probe assemblies to the controller via one or more computerized communication networks 1610, such as one or more public and/or private computer networks.

The controller may be communicatively coupled (e.g., by one or more wired and/or wireless connections) with one or more computer memory devices 1612, such as one or more servers, computer hard drives, optical drives, or the like. The memory devices can store measurements of the lubricant in the machine from the sensor probe assemblies, such as the presence of and/or concentrations of one or more contaminants in the oil of the machine (e.g., water). In one embodiment, the controller may obtain the measurements from the sensor probe assemblies via the data acquisition circuitry and may store the measurements in the memory device. Optionally, the data acquisition circuitry and/or sensor probe assemblies can send the measurements to the memory device without the measurements first being sent to or otherwise provided to the controller.

The controller can examine the measurements provided by the sensor probe assemblies and may use the measurements to predict, self-correct (e.g., using a digital twin of the equipment), and forecast oil change intervals for the equipment. The digital twin of the equipment may be a model of the equipment that may be updated with actual measured characteristics and operational data of the equipment. The digital twin can be used by the controller to determine an oil change interval for the equipment, which may be a prediction of when the oil of the equipment should be changed based on previous operational data and/or based on hypothetical, planned, or predicted upcoming usage of the equipment.

The oil change interval may be a time period between changes of the oil in an engine or a remaining time until an oil change is to occur. The time period may be measured as days, weeks, or months of a calendar; hours and/or minutes of a clock; duty cycles of the engine; or the like. The oil change interval may be predicted by the controller based on a current operational data (e.g., duty cycle) of the engine, as well as oil sample data obtained from one or more of the sensor probe assemblies described herein. This data can include information on which components or impurities are in the oil, as well as the concentration(s) of the impurities. In addition to operational data and oil sample data, fuel sulfur content and an oil top-up date can be obtained as inputs. The fuel sulfur content may be a measurement of how much sulfur is in the fuel supplied to the equipment, which can vary widely across different geographical locations. The oil top-up date may be the date of the last time that oil was added to the equipment or a time period since the last time that oil was added to the engine. Optionally, one or more equipment characteristics of the equipment may be considered, such as whether the engine is a two- or four-stroke engine. As another example, the type of fuel (e.g., gas versus diesel versus a fuel used in hybrid vehicles) can be received as inputs. These inputs can be provided to the controller by one or more input devices (and optionally stored in the memory device), or can be provided to and stored in the memory device from the input device(s) without first being sent to the controller.

In operation, the controller may obtain information related to the equipment from the memory device. This information may include operational data, lubricant sample data, and/or lubricant change data. The operational data can include information indicative of usage of the equipment, such as measurements of impurities in oil of the equipment, date of or time since the last oil change, operational cycles of the equipment, locations where the equipment operated, types of fuel used by the equipment, duration of use of the equipment, temperatures at which the equipment operated, ambient temperatures in which the equipment operated, geometrical details or measurements of the equipment and/or chamber in the equipment that holds the lubricant, power rating of the equipment, lube system parameters of the equipment (e.g., lubricant flow rate, lubricant film temperature, combustion characteristics of the equipment, etc.), and the like.

In one embodiment, the operational data obtained by the controller may include a lubricant top-off date and/or an impurity content of fuel used by the equipment. The top-off date can be the date of or time since lubricant (e.g., oil) was last added to the equipment. The impurity content of the fuel can be the amount of one or more impurities in the fuel consumed by the equipment, such as the sulfur content of fuel supplied to the equipment. Optionally, the operational data obtained by the controller may include a base oil composition, such as a grade of the lubricant (e.g., different generations of lubricant oils, such as generation 6 or 7).

The lubricant sample data may include measurements of the lubricant in the equipment obtained by the sensor probe assembly or assemblies. These measurements can include identification of and/or concentrations of one or more impurities in the lubricant, such as water or non-hydrocarbon components. The lubricant change data can include information on when the lubricant was last changed or replaced, as opposed to when lubricant was last added to the equipment. In one embodiment, the measurements obtained from the sensor and/or other systems may be converted from a reference scale (of the sensor or other origin of the measurements) to an absolute scale before providing the measurements to the digital twin. For example, calibration factors used for converting infrared measured soot data may be used. These conversion factors can vary from values of 5 to 60.

Optionally, the measurement of the amount of impurities in the lubricant can include a measurement of one or more additives to the lubricant. For example, base additives can be added to oil to extend the life of the oil. The amount of one or more additives also can be measured and used to determine when a lubricant change is needed. For example, if an impurity measurement trends upward (e.g., soot) and/or an additive measurement trends downward (e.g., a base additive), then a lubricant change may be needed sooner than if the impurity measurement trends downward or remains the same and/or the additive measurement does not decrease.

The controller can perform an analysis of the obtained information to determine a remaining useful life (RUL) of the lubricant in the equipment based on the information. The controller can examine the operational data, lubricant sample data, and/or lubricant change data to determine how much longer the lubricant can be used without being changed or otherwise replaced at a time that is a designated period of time ahead of a scheduled maintenance of the equipment. For example, the equipment (or a larger powered system that includes the equipment, such as a vehicle) can be scheduled for maintenance or an oil change every three months or three to five thousand miles. At a designated date (e.g., fourteen days ahead of the scheduled oil change or five hundred miles before the next oil change), the controller can automatically obtain the operational data, lubricant sample data, and/or lubricant change data from the memory device and determine the remaining useful life of the lubricant based on this information. Depending on how much longer the remaining useful life is, the controller may direct that the oil change not occur at the next scheduled maintenance, that the next scheduled maintenance be delayed, or that the next scheduled maintenance be performed sooner than the previously scheduled date.

Optionally, the controller can perform the analysis of the operational data, lubricant sample data, and/or lubricant change data to create and/or update a model (e.g., a digital twin) of the equipment. This model can be used to determine a remaining useful life of the equipment and/or other systems of the equipment (e.g., the components that hold and/or direct the flow of lubricant in the equipment). In one embodiment, the digital twin can be used to predict how much longer the equipment can continue operating with the current lubricant given hypothetical or planned future operating conditions of the equipment. For example, a designated number of upcoming operational cycles of the equipment, one or more designated locations where the equipment may operate, one or more designated types of fuel that may be used by the equipment, a designated upcoming total duration of use of the equipment, designated temperatures at which the equipment may operate, designated ambient temperatures in which the equipment may operate, and the like, can be input into the controller (e.g., by the input device(s)). Based on the current state or condition of the lubricant (based on the operational data, lubricant sample data, and/or lubricant change data, as described herein), different hypothetical or planned future operating conditions may result in the controller determining that the lubricant needs to be changed sooner (e.g., than a scheduled maintenance), later (than the scheduled maintenance), that the equipment cannot safely operate under the designated conditions, or the like. For example, if the operational data, lubricant sample data, and/or lubricant change data indicate a poor state of health of the lubricant, then more upcoming operational cycles, poorer quality fuel (e.g., more impurities), longer upcoming durations of use, hotter operating temperatures, hotter ambient temperatures, and the like, will result in the controller determining that the equipment may not safely operate under the designated upcoming operating conditions without an oil change when compared to fewer upcoming operational cycles, higher quality fuel, shorter upcoming durations of use, cooler operating temperatures, cooler ambient temperatures, and the like.

As the equipment operates under the planned or other operational conditions, the operating conditions under which the equipment actually operated can be reported to the controller and/or stored in the memory device. This information can be used to update the digital twin of the equipment. For example, the total number of operational cycles since a lubricant change, the different types of fuel, the total duration of use since a lubricant change, the operating temperatures and/or ambient temperatures, and the like, can be tracked over time. As the total number of operational cycles since a lubricant change increases, poorer quality fuels are used, the total duration of use since a lubricant change increases, the operating temperatures increase, and/or ambient temperatures increase, the shorter of a time span that the equipment can operate without an oil change.

Once a lubricant change occurs, however, the controller can re-set one or more aspects of the digital twin of the equipment. For example, the occurrence of a lubricant change can be input to the controller via the input device(s), and the controller can adjust the digital twin such that data values indicative of previous operating cycles, temperatures, and the like, can be re-set to zero or otherwise changed to indicate that new lubricant is being used in the equipment.

In addition to the operational data, the controller may also use the sample data to determine whether a change of the lubricant may be needed, when a change in the lubricant may be needed, and/or whether the equipment can safely operate under hypothetical or planned upcoming operating conditions without a lubricant change. The sample data can be provided by the sensor probe assemblies and the controller can shorten the time span before the next lubricant change and/or determine that the equipment may not be able to safely operate without a lubricant change for sample data indicating larger amounts of impurities in the lubricant when compared with sample data indicating smaller or no amounts of impurities in the lubricant.

In one embodiment, the controller may also consider the amount of sulfur in the fuel consumed by the equipment in determining the remaining useful life of the lubricant in the equipment. For example, one of the inputs that may be considered by the controller in determining how much longer an engine can continue operating before an oil change is needed may be the amount (e.g., concentration or absolute amount) of sulfur in the fuel supplied to the engine. The controller can shorten the amount of time or reduce the number of duty cycles that the equipment can continue operating before a lubricant change is needed for greater amounts of sulfur in the fuel and can lengthen the amount of time or increase the number of duty cycles that the equipment can continue operating before the lubricant change is needed for lesser amounts of sulfur in the fuel.

The controller optionally may also consider the time or number of duty cycles since a lubricant top-off of the equipment occurred in determining the remaining useful life of the lubricant in the equipment. For example, one of the inputs that may be considered by the controller in determining how much longer an engine can continue operating before an oil change is needed can be when the last time oil was added to the engine. The controller can shorten the amount of time or reduce the number of duty cycles that the equipment can continue operating before a lubricant change is needed for longer periods of time since lubricant was last added to the equipment and can lengthen the amount of time or increase the number of duty cycles that the equipment can continue operating before the lubricant change is needed for shorter time periods since lubricant was last added to the equipment.

Figure 57:
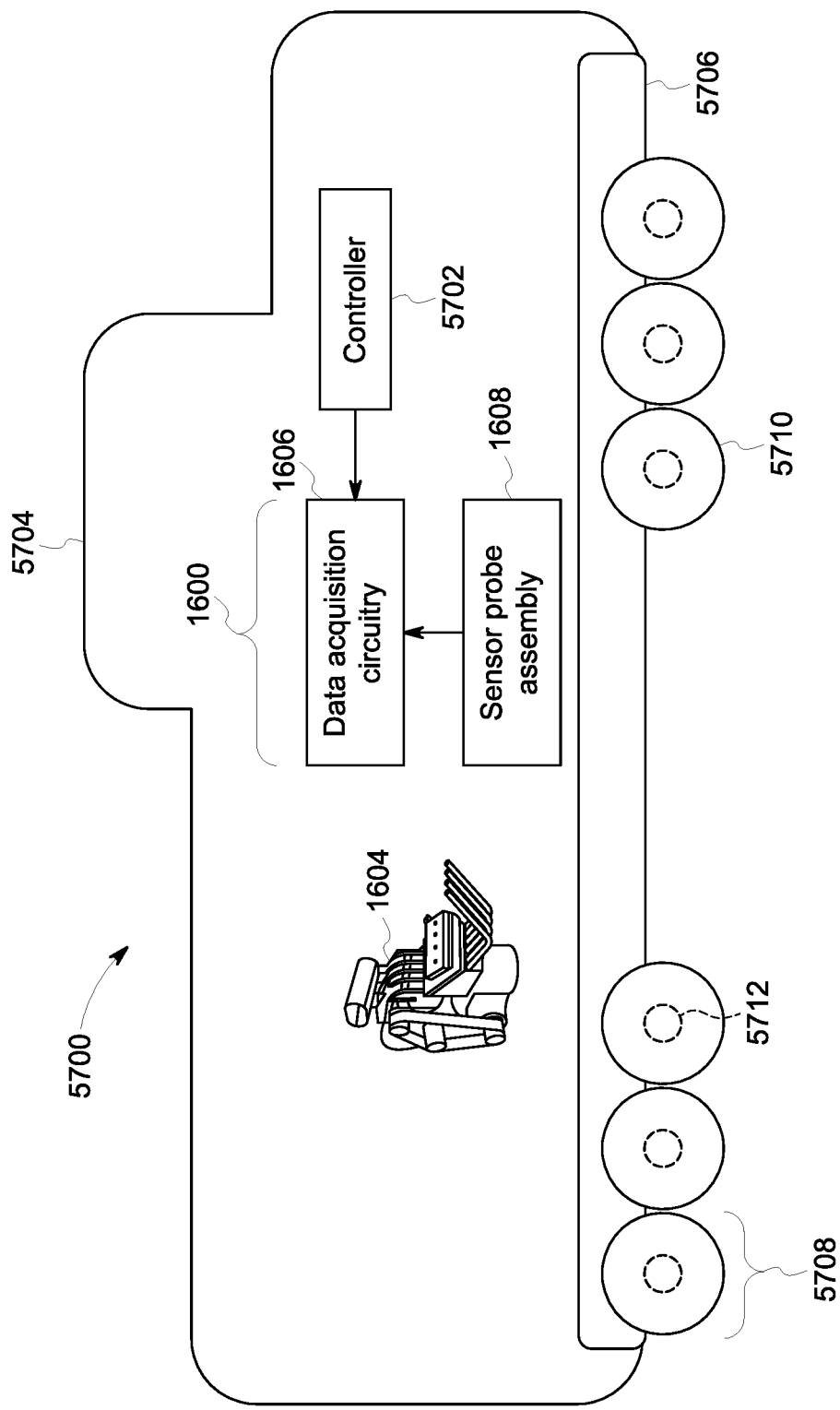
FIG. 57 illustrates another embodiment of the maintenance system used in connection with a powered system.

FIG. 57 illustrates another embodiment of the maintenance system used in connection with a powered system 5700. The powered system may represent a vehicle 5704, such as a locomotive, that may include a vehicle controller 5702 and the equipment described above. The vehicle controller can represent hardware circuitry that includes and/or is connected with one or more processors (e.g., one or more microprocessors, field-programmable gate arrays, integrated circuits, or the like) that may control operation of the rail vehicle. For example, the equipment can represent an engine under control of the vehicle controller to propel the rail vehicle along one or more tracks. The rail vehicle includes a platform 5706, which also can be referred to as a vehicle chassis or body, that supports the maintenance system, the equipment, and other components. The platform is coupled with multiple wheel-axle sets 5708 that each includes two or more wheels 5710 coupled with an axle 5712. The equipment can operate to rotate the axles and wheels to propel the rail vehicle. Optionally, the rail vehicle represents another type of vehicle, such as an automobile, a truck, an aircraft (manned or unmanned), marine vessel, mining vehicle, or the like.

The vehicle controller can be in communication with the data acquisition circuitry (or the controller, not shown) to determine when the equipment may need to have a lubricant (e.g., oil) in the equipment changed or otherwise replaced. The equipment may include a reservoir that holds the lubricant. The equipment optionally can represent another reservoir that holds lubricant. The equipment can be directly or indirectly coupled to the platform.

The controller may obtain measurements of contaminants and other contents of the lubricant from data acquisition circuitry that may receive these measurements from one or more sensor probe assemblies. The controller can store measurements of the lubricant from the sensor probe assemblies, such as the presence of and/or concentrations of one or more contaminants in the oil of the equipment (e.g., water). In one embodiment, the controller may obtain the measurements from the sensor probe assemblies via the data acquisition circuitry and may store the measurements in a memory device, such as the memory device shown in FIG. 16.

The controller can examine the measurements provided by the sensor probe assemblies and may use the measurements to predict, self-correct, and forecast oil change intervals for the equipment. The oil change interval can be predicted by the controller based on a current operational data (e.g., duty cycle) of the equipment, as well as oil sample data obtained from one or more of the sensor probe assemblies described herein. This data can include information on which components or impurities are in the oil, as well as the concentration(s) of the impurities. In addition to operational data and oil sample data, fuel sulfur content and an oil top-up date can be obtained as inputs. The fuel sulfur content may be a measurement of how much sulfur is in the fuel supplied to the equipment, which can vary widely across different geographical locations. The oil top-up date may be the date of the last time that oil was added to the equipment or a time period since the last time that oil was added to the engine. Optionally, one or more equipment characteristics of the equipment may be considered, such as whether the engine is a two- or four-stroke engine. As another example, the type of fuel (e.g., gas versus diesel versus a fuel used in hybrid vehicles) can be received as inputs.

The controller can obtain information related to the equipment such as operational data, lubricant sample data, and/or lubricant change data. The operational data can include information indicative of usage of the equipment, such as measurements of impurities in oil of the equipment, date of or time since the last oil change, operational cycles of the equipment, locations where the equipment operated, types of fuel used by the equipment, duration of use of the equipment, temperatures at which the equipment operated, ambient temperatures in which the equipment operated, geometrical details or measurements of the equipment and/or chamber in the equipment that holds the lubricant, power rating of the equipment 1604, lube system parameters of the equipment (e.g., lubricant flow rate, lubricant film temperature, combustion characteristics of the equipment, etc.), and the like.

In one embodiment, the operational data obtained by the controller may include a lubricant top-off date and/or an impurity content of fuel used by the equipment. The top-off date can be the date of or time since lubricant (e.g., oil) was last added to the equipment. The impurity content of the fuel can be the amount of one or more impurities in the fuel consumed by the equipment, such as the sulfur content of fuel supplied to the equipment. Optionally, the operational data obtained by the controller may include a base oil composition, such as a grade of the lubricant.

The lubricant sample data may include measurements of the lubricant in the equipment obtained by the sensor probe assembly or assemblies. These measurements can include identification of and/or concentrations of one or more impurities in the lubricant, such as water or non-hydrocarbon components. The lubricant change data can include information on when the lubricant was last changed or replaced, as opposed to when lubricant was last added to the equipment.

Optionally, the measurement of the amount of impurities in the lubricant can include a measurement of one or more additives to the lubricant. For example, base additives can be added to oil to extend the life of the oil. The amount of one or more additives also can be measured and used to determine when a lubricant change is needed. For example, if an impurity measurement trends upward (e.g., soot) and/or an additive measurement trends downward (e.g., a base additive), then a lubricant change may be needed sooner than if the impurity measurement trends downward or remains the same and/or the additive measurement does not decrease.

The controller can perform an analysis of the obtained information to determine a remaining useful life (RUL) of the lubricant in the equipment based on the information. The controller can examine the operational data, lubricant sample data, and/or lubricant change data to determine how much longer the lubricant can be used without being changed or otherwise replaced at a time that is a designated period of time ahead of a scheduled maintenance of the equipment. For example, the equipment and/or the rail vehicle can be scheduled for maintenance or an oil change every three months or three to five thousand miles. At a designated date (e.g., fourteen days ahead of the scheduled oil change or five hundred miles before the next oil change), the controller can automatically obtain the operational data, lubricant sample data, and/or lubricant change data from the memory device and determine the remaining useful life of the lubricant based on this information. Depending on how much longer the remaining useful life is, the controller may direct that the oil change not occur at the next scheduled maintenance, that the next scheduled maintenance be delayed, or that the next scheduled maintenance be performed sooner than the previously scheduled date. Optionally, the controller can perform the analysis of the operational data, lubricant sample data, and/or lubricant change data to create and/or update a model (e.g., a digital twin) of the equipment, as described above.

Figure 17:
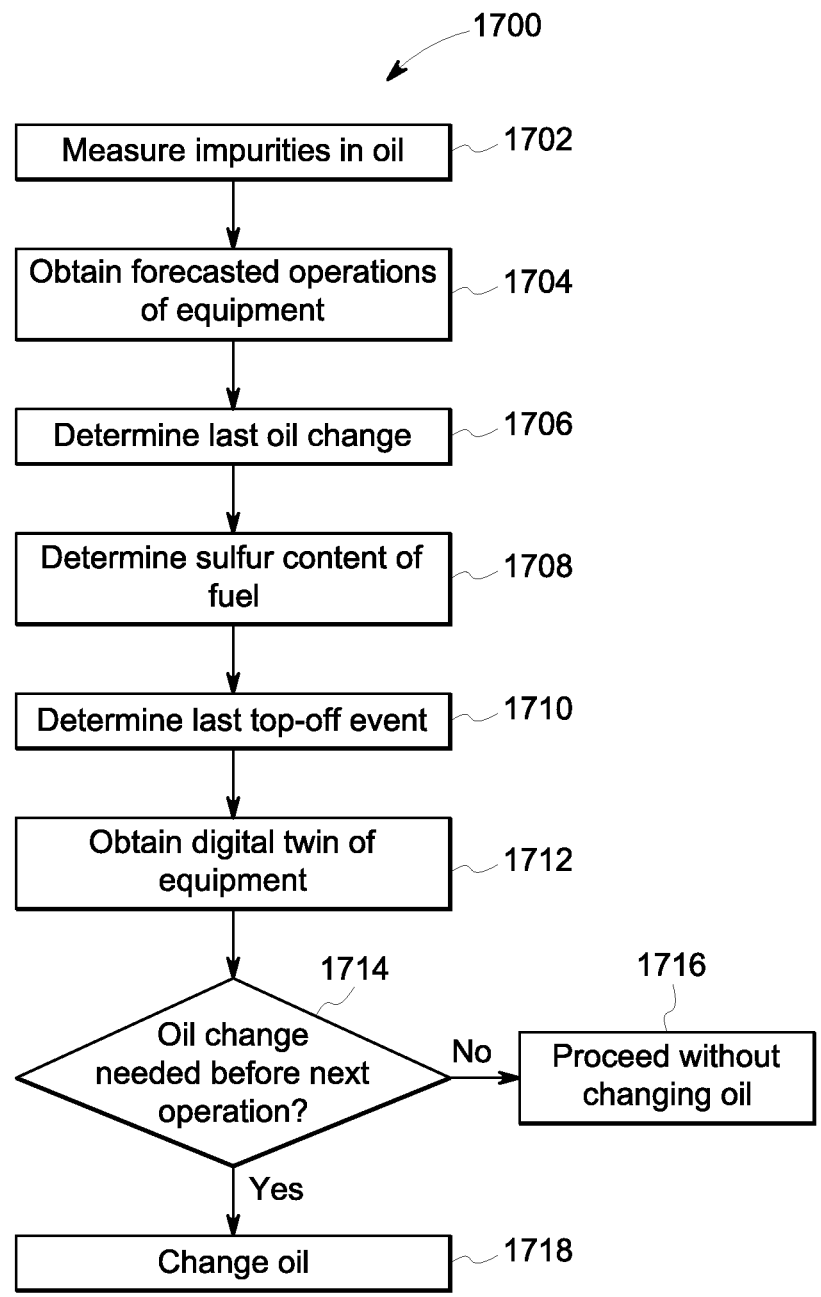
FIG. 17 illustrates a flowchart of one embodiment of a method for determining a maintenance event for equipment.

FIG. 17 illustrates a flowchart of one embodiment of a method 1700 for determining a maintenance event for equipment. The method can be used to determine when a lubricant change for the equipment may be needed based on a variety of input data, which can include the sulfur content of fuel supplied to the equipment and/or the last time that lubricant was added to the equipment. The flowchart of the method can represent operations performed by the controller.

At 1702, the amount of one or more impurities in oil in an engine may be determined. The impurity amount(s) can be measured by one or more of the sensor probe assemblies described herein. Alternatively, another type of sensor can be used. Optionally, the method may not include 1702. At 1704, forecasted operational conditions of the engine are obtained. For example, the ambient temperatures, engine speeds, engine temperatures, durations of operation, and the like, can be determined from operator inputs and/or from a scheduled or planned operation or mission of the engine. Optionally, the method may not include 1704. At 1706, the last time the oil of the engine was changed may be determined. The date and/or time of this event can be stored in the memory device, and the time and/or number of duty cycles since the last time the oil was removed from the engine and then replenished is determined. Optionally, the method may not include 1706.

At 1708, the sulfur content of the fuel that is or will be supplied to the engine may be determined. Different geographic areas may have different amounts of fuel impurities (e.g., sulfur) in the fuel that is available in those areas. Greater amounts of sulfur in fuel that is supplied to the equipment can result in the equipment operating at hotter temperatures, which can cause faster deterioration of the lubricant in the equipment. One embodiment of the inventive subject matter described herein may take the amount of sulfur in fuel used to power the equipment into consideration when determining whether the existing lubricant in the equipment may need to be changed or whether the equipment can continue operating with the existing lubricant. The amount of sulfur in the fuel can be input by an operator of the system, can be obtained from one or more remotely located memory devices (e.g., servers) via the network(s), or the like.

At 1710, a determination may be made as to when lubricant was last added to the equipment. At various times, one or more operators may add lubricant to the equipment, such as when the operator(s) discover that the volume of lubricant in the equipment or a reservoir of the equipment is below a designated lower limit. Some volume of the lubricant can be added to the equipment and/or the reservoir of the equipment at a top-off event. The top-off event may differ from the changing of the lubricant in that lubricant is added to, but not predominantly removed from, the equipment during a top-off event. Lubricant may be predominantly removed (e.g., at least 90% by volume and/or weight) from the equipment and/or an associated reservoir, and then replaced during a changing of the lubricant. The time or date since the last top-off event can be input by an operator of the system, can be obtained from one or more remotely located memory devices (e.g., servers) via the network(s), or the like.

At 1712, a digital twin of the equipment may be obtained. The digital twin of the equipment can be created from the data and information obtained and/or determined at 1702, 1704, 1706, 1708, and/or 1710, and/or an existing digital twin of the equipment can be modified or updated based on some or all of this information. The digital twin can serve as an electronic representation of the equipment, including some or all of the prior usage (duration of use, temperatures, sulfur contents of fuel, date/time of last top-off event, etc.).

At 1714, a decision may be made by the controller as to whether a change of the lubricant is needed. This decision can be based on the controller examining the digital twin of the equipment (which electronically represents usage and/or wear and tear of the equipment, deterioration or deteriorating conditions of the lubricant, etc.), determining forecasted operating conditions (e.g., planned, hypothetical, and/or predicted conditions in which the equipment will operate), the sulfur content of fuel previously supplied to the equipment and/or planned to be provided to the equipment, and/or the time since the last top-off event. If the prior usage of the equipment and lubricant (as represented by the digital twin) indicates a longer time and/or more harsh operating conditions for the equipment (than a shorter operating time and/or less harsh operating conditions), then the controller may determine that an oil change is needed; if the previous sulfur content of the fuel used by the equipment is higher, then the controller may decide that an oil change is needed (when compared with lower sulfur contents); if it has been a longer period of time since the last top-off event, then the controller may determine that an oil change is needed (when compared with shorter periods of time since the last top-off event; and/or if the impurities measured in the oil by the sensor probe assemblies indicate greater amounts of impurities, then the controller may recommend changing the oil sooner (than if fewer amounts of impurities were measured). The controller can determine which combinations of these conditions indicate that an oil change is needed before operation of the equipment can continue, which combinations of conditions indicate that an oil change can be delayed, etc., based on empirically derived or determined combinations of conditions of other equipment and when oil changes for that other equipment occurred.

If the controller determines that a change in the lubricant is needed, then flow of the method can proceed toward 1718. At 1718, the lubricant of the equipment may be changed. For example, the controller can prevent continued operation of the equipment by communicating one or more control signals to the equipment to shut down or prevent continued operation of the equipment. As another example, the controller can send a warning signal to an operator that an oil change is needed. The controller can change or modify planned operational settings of the equipment to allow the equipment to continue operating without the oil change. For example, the equipment may be scheduled to propel a vehicle along a mountainous route in harsh conditions (e.g., elevated temperatures) carrying a heavy load before the next oil change. The controller can prevent this from occurring by either automatically directing the oil be changed or by changing the scheduled operational settings of the equipment.

If the controller determines (at 1714) that a change in the lubricant may not be needed, then flow of the method can proceed toward 1716. For example, the controller can determine that the equipment can continue operating (e.g., with the forecasted operating conditions) before an oil change is needed. As another example, the controller can determine that an oil change is needed, but that the previous and/or planned operating conditions of the equipment and/or lubricant allow for the equipment to continue operating longer without needed a change in lubricant. This can allow for maintenance of the equipment to be delayed without significant risk of damage to the equipment.

Determining when or whether to change lubricant of the equipment as described herein may provide for a condition-based performance of maintenance without significant changes in current operation of the equipment. The useful life of lubricant can be extended beyond a designated oil-change schedule due to usage of the equipment in conditions that do not cause the lubricant to deteriorate as quickly, due to recent top-offs of the lubricant, due to low levels of impurities in the lubricant, etc. Additionally, the frequency at which the lubricant is sampled can be decreased in situations where usage of the equipment is in conditions that may not cause the lubricant to deteriorate as quickly, where the lubricant has been recently added, where there are low levels of impurities in the lubricant, etc. This can reduce the sampling cost involved in maintaining the equipment. Additionally, the controller can determine when data outliers (e.g., measurements of abnormally elevated levels of impurities in oil) are may be false positive detections of impurities, versus when significant and real issues exist, due to examination of the digital twin and previous usage of the equipment. For example, if the equipment has been used in less harsh conditions, lubricant has recently been added to the equipment, other measurements of impurities were low or within acceptable limits, etc., then an abnormally high measurement of impurities in the lubricant can be identified by the controller as a data outlier, and not an actual problem with the lubricant.

In one embodiment, a method may include monitoring previous operational conditions of an engine that operates using fuel and a lubricant, identifying one or more of an impurity content of the fuel supplied to the engine or an elapsed time since a previous addition of additional lubricant to the lubricant in the engine, and determining whether a change of the lubricant may be required prior to continued operation of the engine based on the previous operational conditions and the one or more of the impurity content of the fuel or the elapsed time since the previous addition of the additional lubricant to the lubricant in the engine.

Optionally, the method may include identifying the impurity content of the fuel and the impurity content may be an amount of sulfur in the fuel.

Optionally, the method may include both identifying the impurity content of the fuel and the elapsed time since the previous addition of the additional lubricant. Determining whether the change of the lubricant may be required can be based on the previous operational conditions, the impurity content of the fuel, and the elapsed time since the previous addition of the additional lubricant.

Optionally, the previous operational conditions may include one or more of an elapsed operating time of the engine, an operating temperature of the engine, or an ambient temperature in which the engine operated.

Optionally, the method also can include creating or updating a digital twin of the engine based on the previous operational conditions of the engine, and forecasting upcoming operational conditions of the engine. Determining whether the change of the lubricant may be required prior to the continued operation of the engine may be based on the previous operational conditions, the one or more of the impurity content of the fuel or the elapsed time since the previous addition of the additional lubricant to the lubricant in the engine, the digital twin of the engine, and the upcoming operational conditions of the engine that are forecasted.

Optionally, the method may also include automatically changing the lubricant in the engine based on determining that the change in the lubricant may be required. For example, one or more of the controllers described herein can generate and communicate control signals to a scheduling system that schedules the change or addition of lubricant to the engine.

Optionally, determining whether the change of the lubricant may be required may involve delaying the change of the lubricant beyond a previously scheduled maintenance of the engine that involves changing the lubricant.

Aging of chemical gas sensor systems such as the sensor probe assemblies described herein can pose a significant limitation in broad industrial application of the assemblies where long term stability of installed sensors may be needed. To address this challenging problem, different approaches have been implemented. In particular, sensors may be periodically recalibrated by removing the sensors from a measurement system, by bringing a carrier gas to the sensor without removing the sensors from the measurement system, and/or by simultaneously re-charging and calibrating the sensors on a regular basis (e.g., daily). Sensor aging may be defined here as any detectable change in sensor sensitivity or sensor selectivity or sensor offset or sensor drift or sensor response time or sensor recovery time upon normal operation conditions of the sensor over time or upon exposure of the sensor to any undesired conditions. Nonlimiting examples of the undesired conditions may include poisoning, mechanical degradation, and any other undesired conditions.

These and other known calibration methods may have significant limitations. For example, the methods can require calibrations with an analyte gas that may occur more frequently than the maintenance cycle of the system itself (e.g., a transformer). As another example, the methods can require a calibration gas to be presented to the sensor.

One or more embodiments of the inventive subject matter described herein may provide systems and methods that may correct for the aging of one or more sensor probe assemblies without removal of the sensor probe assemblies from a measurement system and without the need for user interaction or recalibration with analyte. The systems and methods may use the condition of the sensor probe assembly when the assembly is not responding to a gas or fluid of interest, but may quantitatively affected by aging of the sensor probe assembly. For example, when a sensor probe assembly is in the OFF state (i.e., not powered), this sensor condition or sensor state may be quantitatively affected by the aging of the sensor probe assembly and can be detected by resistance and/or impedance spectroscopy readouts of the assembly at a specific range of frequencies. When the same sensor probe assembly is in the ON state (i.e., powered), the drift in the sensor response due to aging may be correlated with the OFF state of the sensor probe assembly.

The response of the sensor probe assembly when in the OFF state (also referred to as the OFF sensor response) can be used to correct for drift in the response of the sensor probe assembly in the ON state (also referred to as the ON sensor response) due to aging. This technique of sensor correction may be applied to one or more embodiments of the sensor probe assemblies having metal oxide semiconductor elements on the electrodes. The metal oxide semiconductor sensors can detect numerous gases by the selection of the base semiconductor material and the doping of the material. Impedance measurements of metal oxide semiconductor sensors may be used to allow more selective sensor responses. When the sensor is in OFF state (not powered), the sensor output may be measured and then utilized to correct for aging effects when the sensor is in the ON state.

This correction can reduce or eliminate the need for frequent sensor calibration using an analyte gas. Instead, when the sensor is aging, the aging condition of the sensor may be quantified using the sensor response in the OFF state. The aging condition measured in the OFF state may then used to correct for effect of aging when the sensor is in the ON state and responding to the analyte gas, or gases of interest, and to known interferences. This aging condition of the sensor can be detected by resistance and/or impedance spectroscopy readouts at a specific range of frequencies.

Figure 18:
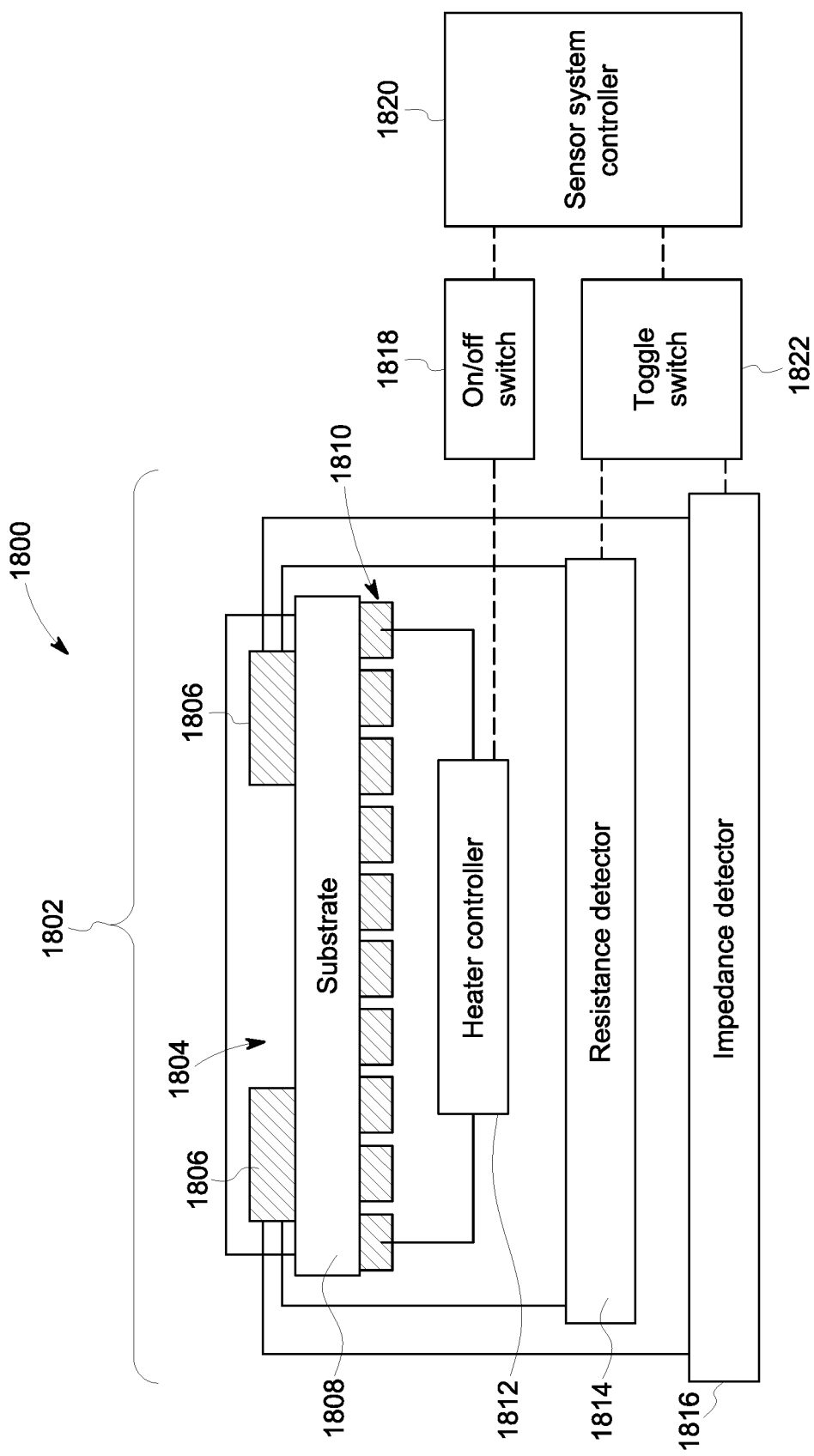
FIG. 18 illustrates one embodiment of a measurement system that corrects for aging in a sensor probe assembly.

FIG. 18 illustrates one embodiment of a measurement system 1800 that corrects for aging in a sensor probe assembly 1802. The sensor probe assembly can represent one or more of the sensor probe assemblies described herein. Optionally, the sensor probe assembly can be another type of sensor probe assembly that measures concentrations of one or more analytes of interest in a fluid under examination using impedance spectral responses of a semiconductor material to the analytes and an electric field generated by electrodes. The fluid under examination can be gas.

The sensor probe assembly may include sensing material 1804 on and/or in contact with conductive electrodes 1806 that may generate an electric field between the electrodes. The sensing material can be a metal oxide semiconductor material, such as SnO2. The electrodes are shown as being deposited on a dielectric substrate 1808 (e.g., the substrate 102, 906), but alternatively may be the free-standing electrodes with the sensing material deposed thereon, as described above. One or more heating elements 1810 are formed from conductive bars, plates, or other resistive bodies that receive electric current to heat the substrate, the sensing material, and/or the electrodes.

A heater controller 1812 may represent hardware circuitry that may be conductively coupled with and conduct electric current to or through the heating elements to generate heat. A resistance detector 1814 may represent hardware circuitry that may be conductively coupled with the electrodes to measure electric resistance between the electrodes (e.g., through the sensing material, which can have a resistance and/or impedance that varies based on the presence and/or amount of impurities or analytes of interest in the fluid under examination). The resistance detector may perform measurements of resistance of the sensing material while the sensor probe assembly is in the ON state (e.g., power is being supplied to the heating elements from the heater controller).

The system may also include additional sensor components such as an impedance detector 1816, which may represent hardware circuitry that may be conductively coupled with the electrodes and that may measure the impedance of the sensing material between the electrodes while the sensor probe assembly is in the ON state and/or the OFF state. The ON state of the sensor may be when a nominal required power may be supplied to the heating elements from the heater controller to achieve a desired response of the sensor to the analyte of interest. Such desired sensor response may be achieved when the sensing material operates at needed temperature in the range from about 100 degrees Celsius to about 800 degrees Celsius and more particularly in the range from about 200 degrees Celsius to about 500 degrees Celsius. The OFF state of the sensor may be when a nominal required power is not supplied to the heating elements from the heater controller so the sensor may not have a detectable response to the analyte of interest. Two examples of "no nominal required power" may include (1) zero applied power when the heating elements have zero power from the heater controller and allows the sensing material to be at ambient temperature or (2) minimal applied power when the heating elements have minimal power from the heater controller that may not produce a desired response of the sensor to the analyte of interest but may allow the sensing material to be slightly above ambient temperature. For example, if ambient temperature is below zero degrees Celsius, the sensing material can be slightly above zero degrees Celsius (for example at 5-20 degrees Celsius) to avoid freezing of condensed water from ambient air onto the sensing material. A first switch 1818 ("ON/OFF switch" in FIG. 18) may operate under the control of a sensor system controller 1820 to switch between activating the heater controller (to supply current to the heating elements) and deactivating the heater controller (to stop supplying current to the heating elements). A second switch 1822 ("Toggle switch" in FIG. 18) may be controlled by the controller to alternate between activating the resistance detector or sensor (to measure the resistance in the sensing material) or activating the impedance detector or sensor (to measure the impedance in the sensing material). The controller may represent hardware circuitry that may include and/or may be connected with one or more processors to control whether the resistance detector or impedance detector is activated, and whether the heater controller may be activated using the switches. The controller can operate based off on input received from an operator and/or may automatically control the switches (e.g., based on a clock and/or schedule).

One example of a transfer function for predicting a gas concentration from a response of the sensing material of the sensor probe assembly described herein may be:

$$[\text{gas}] = A*[\text{sensor response}]^B$$

where [gas] may be the predicted gas concentration (or concentration of an analyte of interest in a fluid such as a gas, [sensor response] may be the measured response of the sensor probe assembly, and A and B may be coefficients of the transfer function. These coefficients of the transfer function may be used for temperature correction and other factors, such as correction for humidity and other gases. The values of the coefficients can be set based on known concentrations of the analyte of interest in a gas sample during calibration of the sensor probe assembly.

Inventors of the inventive subject matter described herein have discovered that the values of the coefficients A and B of this transfer function may be dependent on the aging status of the sensor probe assembly. To get the dependence of these coefficients on sensor aging, but not on the possible analyte gas concentration, the response of the sensor probe assembly can be measured when the sensor probe assembly is unpowered. Stated differently, when the sensor probe assembly is OFF, the sensor probe assembly may not respond to the gas of interest, and measurements of the response of the assembly may be indicative of or represent changes to the values of A and/or B due to aging.

The controller can direct the sensor probe assembly to operate in an impedance mode where the impedance of the sensing material may be measured. The switch may be actuated to activate the impedance detector and to measure the [sensor response] as $Z_{ON}$ (which may be impedance of the sensor probe assembly at a designated frequency) while the sensor probe assembly is ON. The coefficients A and B can be related to the sensor probe assembly in the ON state and OFF state as follows:

$$[gas]=A_{ON,OFF} * Z_{ON}^{B_{ON,OFF}}$$

where the changes in coefficients $A_{ON,OFF}$ and $B_{ON,OFF}$ may be due to the response of the sensor probe assembly to an analyte of interest (e.g., H2) while the sensor probe assembly is in the ON state as correlated to sensor aging (as determined from measurements obtained while the sensor probe assembly is in the OFF state).

Figure 19:
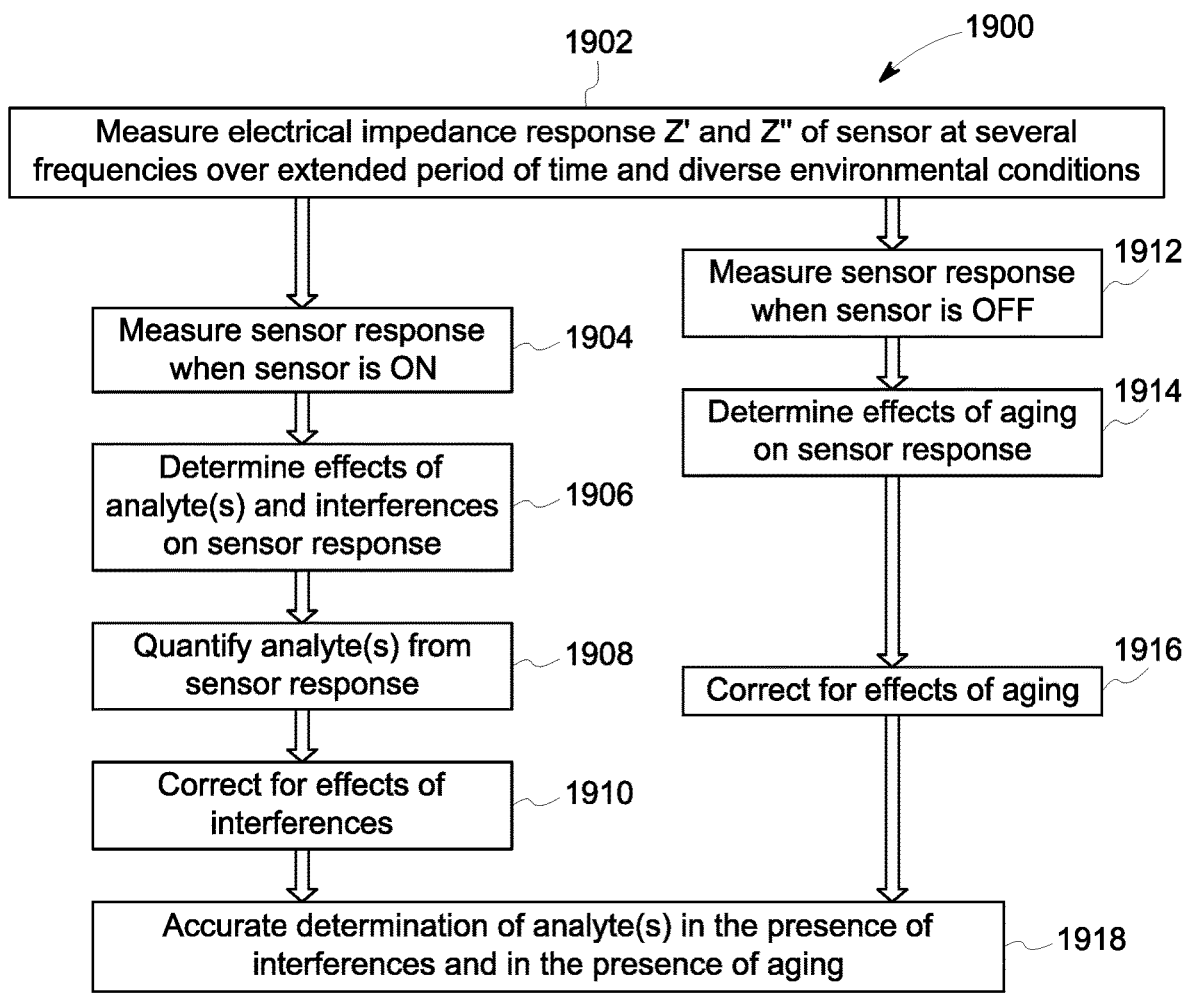
FIG. 19 illustrates a flowchart of one embodiment of a method for correcting measurements of a sensor probe assembly for aging.

FIG. 19 illustrates a flowchart of one embodiment of a method 1900 for correcting measurements of a sensor probe assembly for aging. The method can be performed by the system and/or the controller of the system to correct measurements obtained by one or more of the sensor probe assemblies described herein.

At 1902 and 1904, real (Z') and imaginary (Z") parts of the electrical impedance response of the sensing material of the sensor probe assembly may be measured at several different frequencies while the sensor is in the ON state over an extended period of time and/or under diverse environmental conditions (e.g., exposure to different fluids of interest, different ambient temperatures, etc.). These responses of the sensor probe assembly can be measured by the controller based on output from the impedance detector. At 1906, the intrinsic impedance of the sensor probe assembly can be measured while the sensor probe assembly is powered, and the values of the sensor impedance at certain designated frequencies can be used for determination of effects of interferences on the sensor probe assembly and for accurate quantitation of analytes. At 1908, the analyte(s) in the fluid under examination can be identified based on the sensor response, such as by identifying peaks in one or more impedance spectra of the sensor probe assembly that are associated with the analyte(s) of interest. At 1910, the effects of interferences can be corrected for, such as the impact of aging on the sensor probe assembly, as described in connection with 1912, 1914, 1916. At 1918, the accuracy of quantitation of analytes may be achieved from the correction of sensor response based on the effects of the interferences (e.g., aging of the sensor probe assembly).

The method also may include, at 1902 and 1912, measuring the intrinsic impedance of the sensor probe assembly while the sensor probe assembly is OFF (not powered). These measurements can be performed at designated frequencies that may allow the use of conventional measurement systems with detection of 1 GOhm, 100 MOhm, 10 MOhm, or 1 MOhm. At 1914, the values of the sensor impedance at one or more designated frequencies while the sensor probe assembly is in the OFF state may be determined. These frequencies can be empirically determined from the same or other similar sensor probe assemblies. These values may indicate the effects of aging on the sensor probe assembly.

At 1916, the values determined at 1914 may be used for correction of the instabilities of the sensor response due to sensor aging. Also, the values of the sensor impedance at certain frequencies may be used for correction of the instabilities of the sensor response to an analyte gas of interest when the sensor is powered. For example, these values may be subtracted or otherwise removed from the values determined at 1904 and/or 1908.

Figure 20:
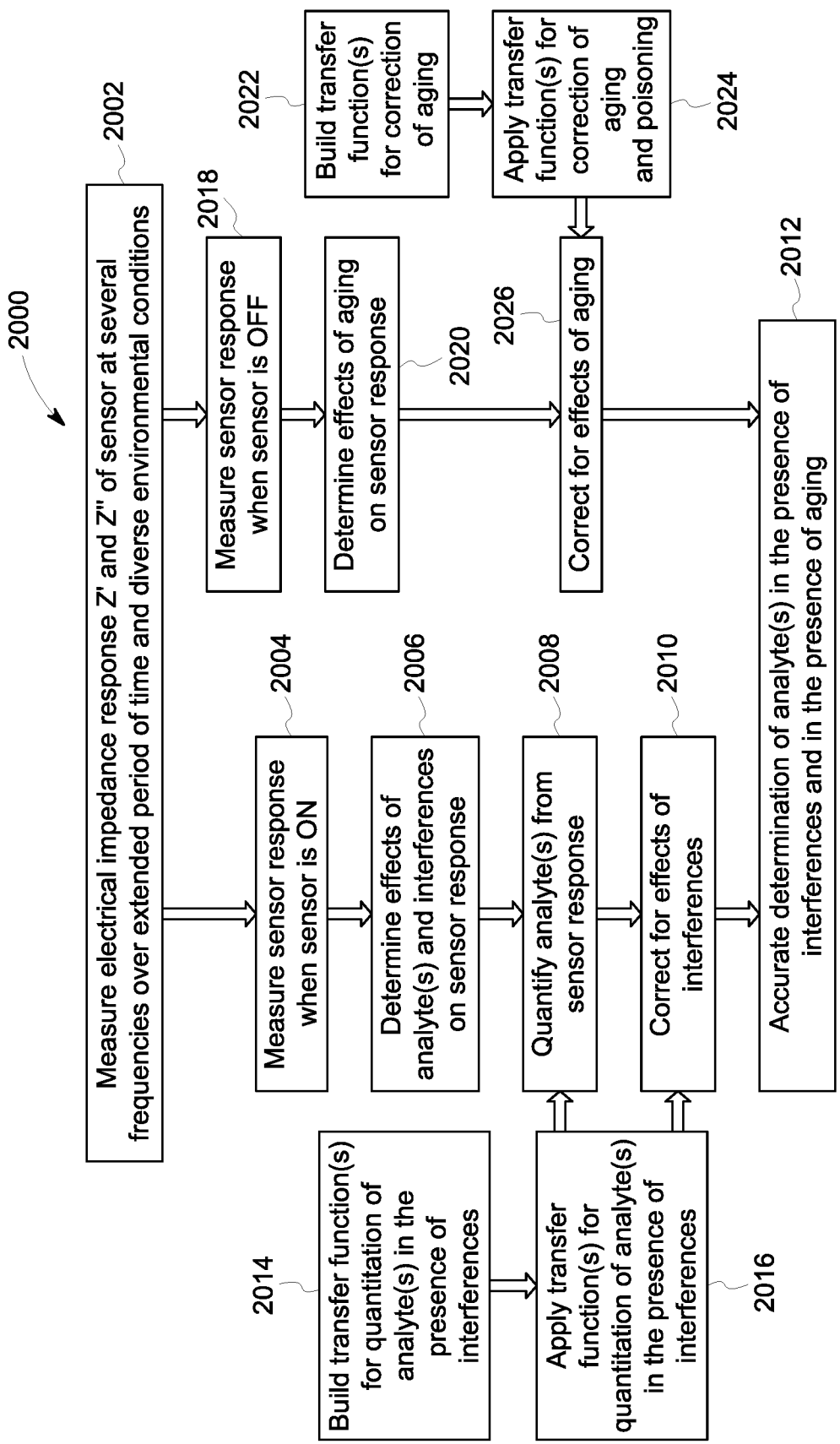
FIG. 20 illustrates another flowchart of one embodiment of a method for correcting measurements of a sensor probe assembly for aging.

FIG. 20 illustrates another flowchart of one embodiment of a method 2000 for correcting measurements of a sensor probe assembly for aging. The method can be performed by the system and/or the controller of the system to correct measurements obtained by one or more of the sensor probe assemblies described herein. At 2002 and 2004, the real part (Z') and imaginary part (Z") of the electrical impedance response of the sensor probe assembly may be measured at several designated frequencies while the sensor probe assembly is in the ON state over extended period of time and while exposed to diverse environmental conditions.

At 2006, the values of the sensor impedance at designated frequencies may be used to determine the effects of interferences and analytes on the sensor probe assembly. For example, the presence of some impurities in a fluid under examination can impact the real part (Z') and/or the imaginary part (Z") of the electrical impedance response of the sensor probe assembly, which also can be impacted by one or more analytes of interest in the fluid. At 2008, the analyte(s) in the fluid under examination can be identified based on the sensor response, such as by identifying peaks in one or more impedance spectra of the sensor probe assembly that are associated with the analyte(s) of interest.

At 2010, the accuracy of quantitation of analytes may be achieved from the correction of sensor response based on the effects of the interferences. For example, the impact of sensor aging on the sensor response measured at 2004 can be removed from the measured sensor response. The analytes of interest in the fluid under examination can then be identified at 2012.

In one embodiment, one or more transfer functions may be built or otherwise created for quantitation of one or more analytes of interest in the presence of interferences, such as impurities or manufacturing errors, at 2014. These transfer functions can be built during sensor fabrication and calibration. These transfer functions may be applied to quantify one or more analytes in the presence of interferences. For example, at 2008 and/or 2010, one or more of the transfer functions (determined at 2014) can be applied to the sensor response to eliminate or reduce the impact of the sensor response on the interferences.

The method 2000 may also include, at 2002 and 2018, measuring the intrinsic impedance of the sensor probe assembly while the sensor probe assembly is OFF (not powered). These measurements can be performed at designated frequencies that allow the use of conventional measurement systems with detection of 1 GOhm, 100 MOhm, 10 MOhm, or 1 MOhm. At 2020, the values of the sensor impedance at one or more designated frequencies while the sensor probe assembly is in the OFF state are determined. These frequencies can be empirically determined from the same or other similar sensor probe assemblies. These values may indicate the effects of aging on the sensor probe assembly.

One or more transfer functions may be built or otherwise created for quantitation of the impact of sensor aging at 2022. These transfer functions can be created based on the sensor responses measured when the sensor probe assembly is OFF, as described above. These transfer functions may be applied to quantify one or more analytes in the presence of interferences. For example, at 2024, one or more of the transfer functions (determined at 2022) can be applied to the sensor response to eliminate or reduce the impact of the sensor response due to aging (at 2026).

Figure 21:
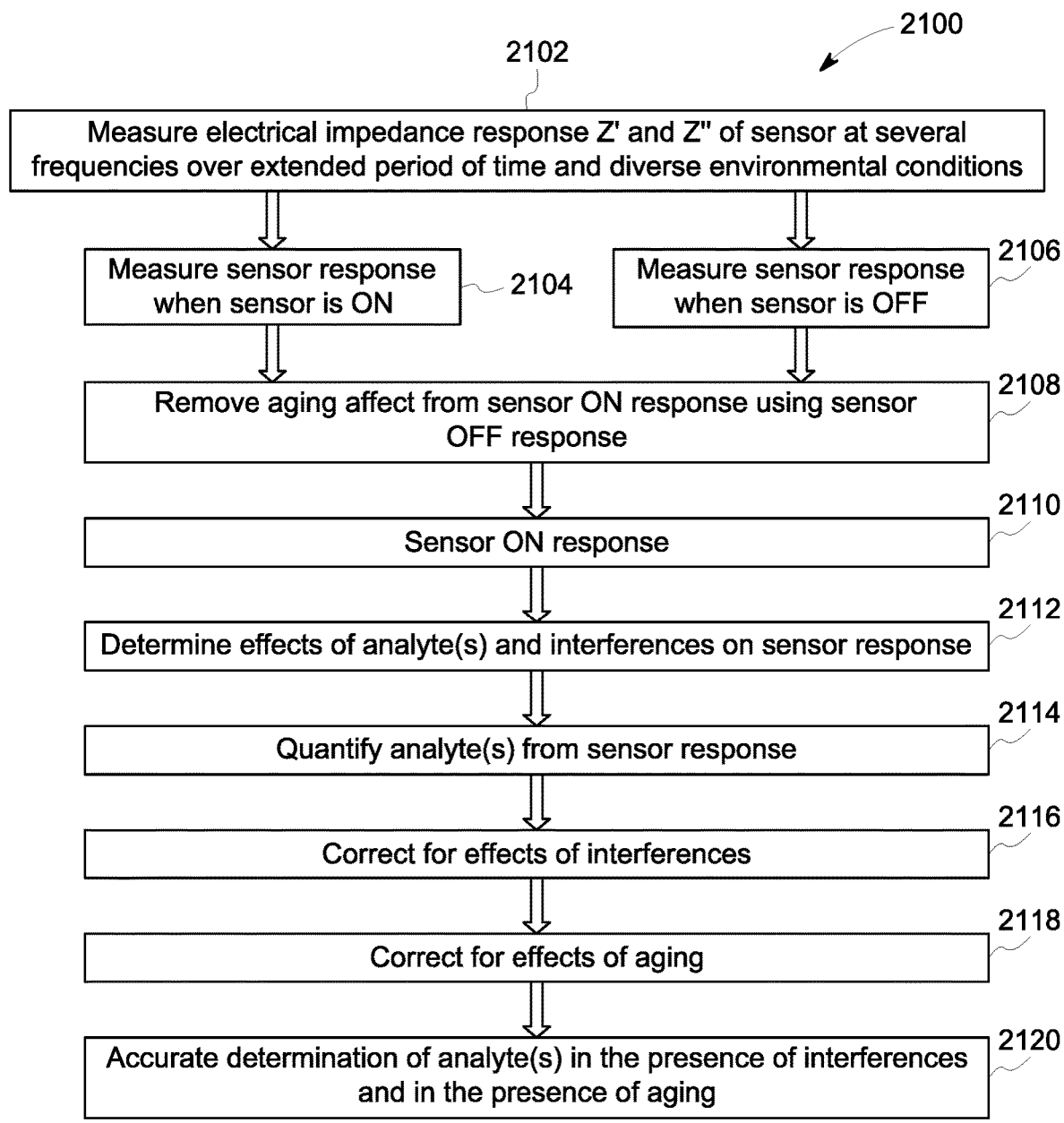
FIG. 21 illustrates a flowchart of one embodiment of a method for correcting measurements of a sensor probe assembly for aging.

FIG. 21 illustrates a flowchart of one embodiment of a method 2100 for correcting measurements of a sensor probe assembly for aging. The method 2100 can be performed by the system and/or the controller of the system to correct measurements obtained by one or more of the sensor probe assemblies described herein.

At 2102, real (Z') and imaginary (Z") parts of the electrical impedance response of the sensing material of the sensor probe assembly may be measured at several different frequencies over an extended period of time and/or under diverse environmental conditions (e.g., exposure to different fluids of interest, different ambient temperatures, etc.). These responses can be measured while the sensor probe assembly is ON (at 2104) and while the sensor probe assembly is OFF (at 2106).

The effects of the sensor responses due to aging of the sensor probe assembly may be removed from the sensor responses measured while the sensor probe assembly is ON at 2108. For example, the real (Z') and imaginary (Z") parts of the electrical impedance response of the sensing material of the sensor probe assembly may be measured while the sensor probe assembly is OFF (at 2106). The real (Z') part of the impedance response measured while the sensor probe assembly is OFF can be subtracted or otherwise removed from the real (Z') part of the impedance response measured while the sensor probe assembly is ON. The imaginary (Z") part of the impedance response measured while the sensor probe assembly is OFF can be subtracted or otherwise removed from the imaginary (Z") part of the impedance response measured while the sensor probe assembly is ON.

After removing the effects of sensor aging (or at least determining the impact of aging so that the impact can later be removed), the real (Z') and imaginary (Z") parts of the electrical impedance response of the sensing material of the sensor probe assembly can be measured for a fluid under examination at 2110. At 2112, the intrinsic impedance of the sensor probe assembly can be measured while the sensor probe assembly is powered, and the values of the sensor impedance at certain designated frequencies can be used for determination of effects of interferences on the sensor probe assembly and for accurate quantitation of analytes. At 2114, one or more analytes of interest in the fluid under examination may be quantified or identified using the sensor response measured at 2110. At 2116, the effect of these interferences can be corrected for, such as by removing the effect of the interferences from the sensor response determined at 2112.

At 2118, the effects of the sensor responses due to aging of the sensor probe assembly optionally may be removed from the sensor responses measured while the sensor probe assembly is ON (at 2110). For example, the real (Z') and imaginary (Z") parts of the electrical impedance response of the sensing material of the sensor probe assembly may be measured while the sensor probe assembly is OFF. The real (Z') part of the impedance response measured while the sensor probe assembly is OFF can be subtracted or otherwise removed from the real (Z') part of the impedance response measured while the sensor probe assembly is ON. The imaginary (Z") part of the impedance response measured while the sensor probe assembly is OFF can be subtracted or otherwise removed from the imaginary (Z") part of the impedance response measured while the sensor probe assembly is ON.

At 2120, one or more analytes of interest may be identified in the fluid under examination with the effects of interferences and the effects of sensor aging removed or reduced from the sensor response. As described herein, different analytes of interest can be associated with different peaks in the real (Z') and/or imaginary (Z") parts of the impedance responses of the sensor probe assembly. After removing the effects of interferences and sensor aging from the sensor response to the fluid under examination, the sensor response may more accurately reflect the presence and/or amount of the analyte(s) of interest in the fluid under examination.

Figure 22:
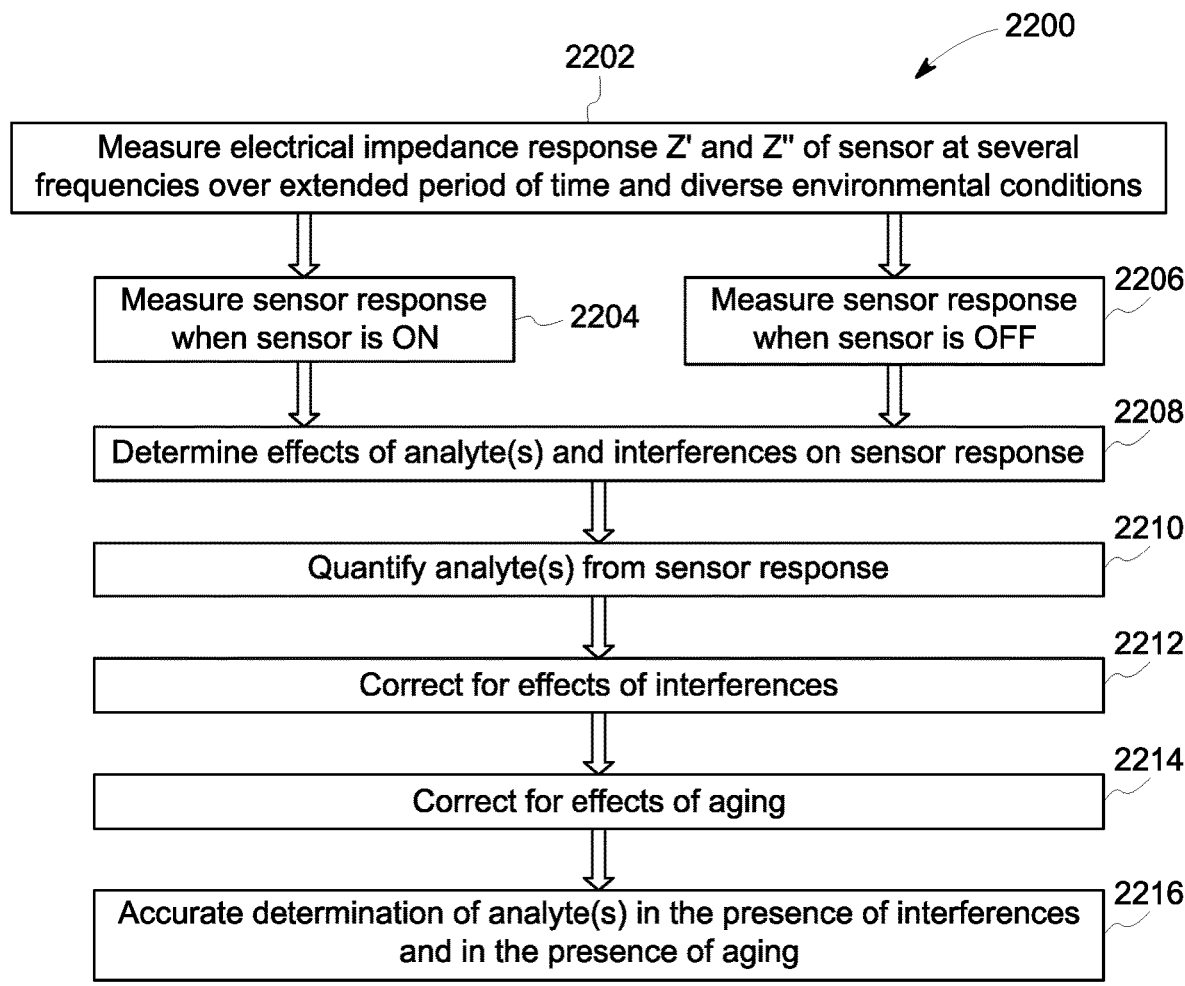
FIG. 22 illustrates a flowchart of one embodiment of a method for correcting measurements of a sensor probe assembly for aging.

FIG. 22 illustrates a flowchart of one embodiment of a method 2200 for correcting measurements of a sensor probe assembly for aging. The method 2200 can be performed by the system and/or the controller of the system to correct measurements obtained by one or more of the sensor probe assemblies described herein.

At 2202, real (Z') and imaginary (Z") parts of the electrical impedance response of the sensing material of the sensor probe assembly may be measured at several different frequencies over an extended period of time and/or under diverse environmental conditions (e.g., exposure to different fluids of interest, different ambient temperatures, etc.). These responses can be measured while the sensor probe assembly is ON (at 2204) and while the sensor probe assembly is OFF (at 2206).

At 2208, the intrinsic impedance of the sensor probe assembly can be measured while the sensor probe assembly is powered, and the values of the sensor impedance at certain designated frequencies can be used for determination of effects of interferences on the sensor probe assembly and for accurate quantitation of analytes. At 2210, one or more analytes of interest in the fluid under examination may be quantified or identified using the measured sensor responses.

At 2212, the effect of these interferences can be corrected for, such as by removing the effect of the interferences from the sensor response that was determined. At 2214, the effects of the sensor responses due to aging of the sensor probe assembly optionally may be removed from the sensor responses measured while the sensor probe assembly is ON. For example, the real (Z') and imaginary (Z") parts of the electrical impedance response of the sensing material of the sensor probe assembly may be measured while the sensor probe assembly is OFF. The real (Z') part of the impedance response measured while the sensor probe assembly is OFF can be subtracted or otherwise removed from the real (Z') part of the impedance response measured while the sensor probe assembly is ON. The imaginary (Z") part of the impedance response measured while the sensor probe assembly is OFF can be subtracted or otherwise removed from the imaginary (Z") part of the impedance response measured while the sensor probe assembly is ON.

At 2216, one or more analytes of interest may be identified in the fluid under examination with the effects of interferences and the effects of sensor aging removed or reduced from the sensor response. As described herein, different analytes of interest can be associated with different peaks in the real (Z') and/or imaginary (Z") parts of the impedance responses of the sensor probe assembly. After removing the effects of interferences and sensor aging from the sensor response to the fluid under examination, the sensor response may more accurately reflect the presence and/or amount of the analyte(s) of interest in the fluid under examination.

The sensor probe assemblies described herein can be used to quantify at least one analyte gas that is dissolved in insulating oil of an electrical transformer. The sensor probe assemblies can be used to quantify at least one analyte gas dissolved in insulating oil of an electrical transformer when the sensor probe assemblies are turned off for extended periods of time (e.g., time periods that are at least 10 times longer that the measurement time of the analyte gas dissolved in insulating oil of an electrical transformer). The sensor probe assembly can be used to quantify analytes of interest such as hydrogen, CO, or a hydrocarbon gas.

The measurement systems described herein can be used to measure a gas extracted from oil (e.g., transformer dissolved gas analysis). The measurement system can include a sensing element or material connected to an impedance detector or analyzer circuit, where the impedance detector or analyzer circuit may measure the response of the sensing element when exposed to a gas that has been extracted from oil and corrects for sensor aging. The sensing element can be connected to a resistance detector or measurement circuit (or equivalent), where the resistance circuit may measure the response of the sensing element when exposed to a gas that has been extracted from oil and corrects for sensor aging.

In one embodiment, the measurement system may operate with a sensing element (e.g., the sensing material) in a gas sample which has been extracted from transformer oil. The sensing element may be connected to an impedance analyzer and scanned as a function of frequency, where the impedance analyzer circuit may provide data output enabling improved sensor selectivity across multiple gases and improved sensor stability based on the correction of the sensor response performed when the sensor is in the OFF state. Aging of the sensor probe assembly can induce significant error in predicted gas concentrations, and when the use of sensor readings in a "sensor OFF" state corrects for sensor aging and when incorporation of the "sensor OFF" response into a transfer function reduces prediction error of gas concentrations.

A method also may be provided herein where sensor aging may induce significant error in predicted gas concentrations. The use of sensor readings in a "sensor OFF" state may correct for sensor aging and incorporation of the "sensor OFF" response into a transfer function reduces prediction error of gas concentrations. The sensor response in the OFF state can be quantified using a resistance measurement of the sensing material (i.e., instead of the impedance response), and the sensor response in the ON state can be quantified using the impedance response. Optionally, the sensor response in the OFF state can be quantified using a resistance measurement of the sensing material (i.e. instead of the impedance response), and the sensor response in the ON state is also quantified using the resistance response.

In one embodiment, the sensor response in the OFF state may be quantified using the resistance measurement (i.e. instead of the impedance response), and the sensor response in the ON state may be also quantified using the resistance response. Optionally, the sensor response in the OFF state is quantified using the resistance measurement (i.e. instead of the impedance response), and the sensor response in the ON state is also quantified using the resistance response.

The frequencies, or frequency ranges, used to measure the impedance response of the sensor probe assembly to quantify the sensor OFF and ON states may be different. The sensor response in the OFF state can be used to correct the sensor response in the ON state prior to applying transfer functions that quantify the analyte gas, or gases of interest. The sensor response in the OFF state can be used simultaneously with the sensor response in the ON state to quantify the analyte gas, or gases of interest. The sensitivity of the transfer functions to the sensor OFF or ON responses can be increased by preprocessing the sensor OFF or ON responses.

In one embodiment, recalibration, realignment or correction for sensor aging using sensor response in the resistance or impedance domain may be performed on a periodic basis, as opposed to being part of a standard measurement cycle. Sensor analysis can be performed on a cyclical basis (such as every 24 hours, weekly, monthly, etc.) and changes in measurement performance (drift, aging etc.) can be corrected based on a cyclic correction. The sensor resistance response in the sensor OFF state can be used as a diagnostic indicator for sensor performance. The information extracted from the resistive method will indicate whether the sensor performance may be within an acceptable range or whether the sensor performance may have drifted outside the acceptable range.

Several measurements were performed using a sensor probe assembly described herein with a SnO2 metal oxide semiconducting sensing material. The readout was performed using an impedance measurement over the relaxation region of the sensing material or classic resistance measurement. A SnO2 sensor probe assembly was aged by exposing the sensor probe assembly to D3 silicone vapor. Such aging reduces the magnitude of the response of the sensor probe assembly to analytes of interest. The sensor probe assembly was exposed to several concentrations of hydrogen gas before and after aging. Concentrations of H2 were 50, 100, 150, and 200 ppm. Exposure to silicone vapor was performed when the sensor probe assembly was in the OFF state to mimic the realistic conditions of the operation of the sensor. Exposures were performed for different durations of 15, 60, and 90 min by keeping the sensor probe assembly in the headspace above the silicone material.

Figure 23:
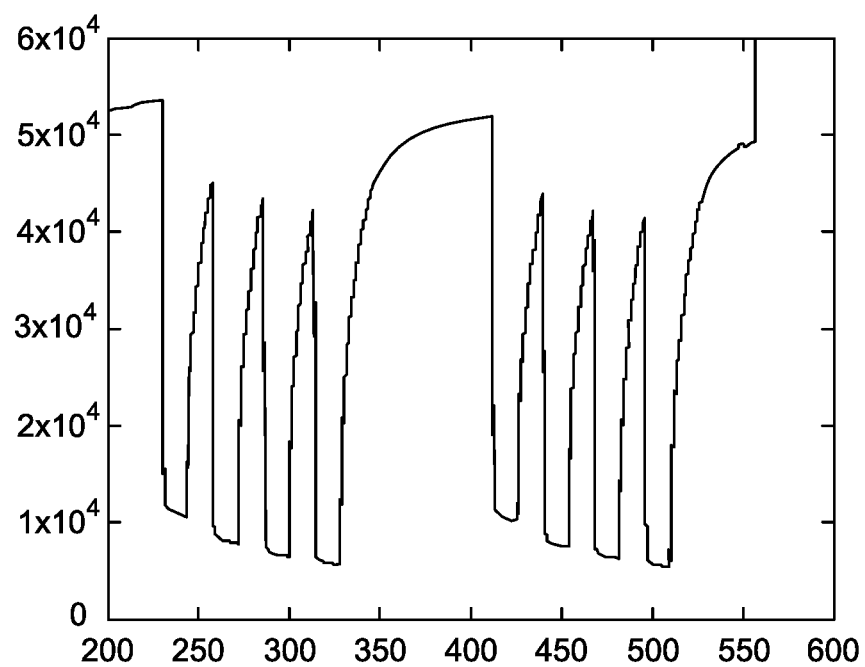
FIG. 23 illustrates response of a sensor probe assembly when the sensor probe assembly was tested during exposure to H2 before and after accelerated aging steps.
Figure 24:
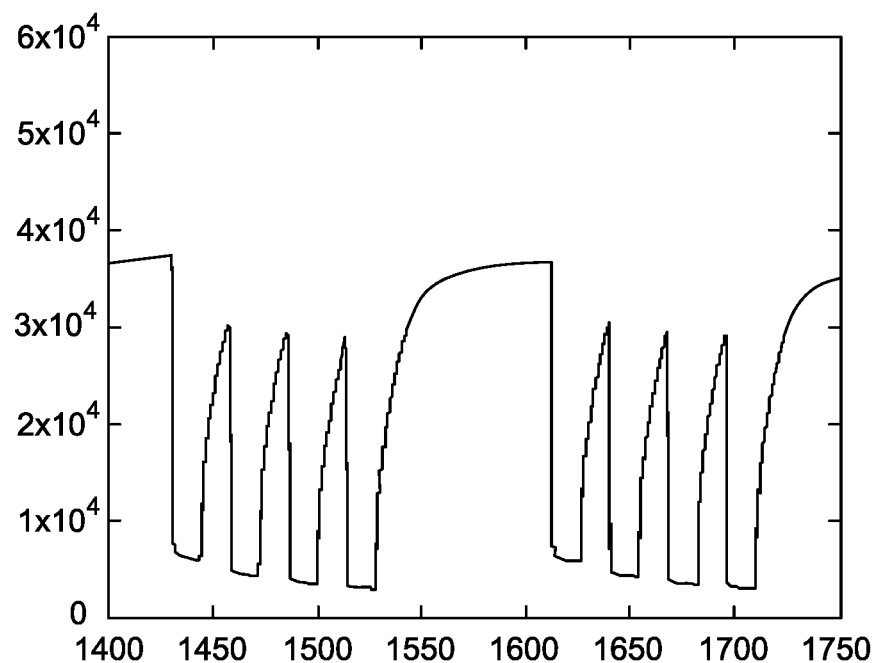
FIG. 24 illustrates additional response of a sensor probe assembly when the sensor probe assembly was tested during exposure to H2 before and after accelerated aging steps.
Figure 25:
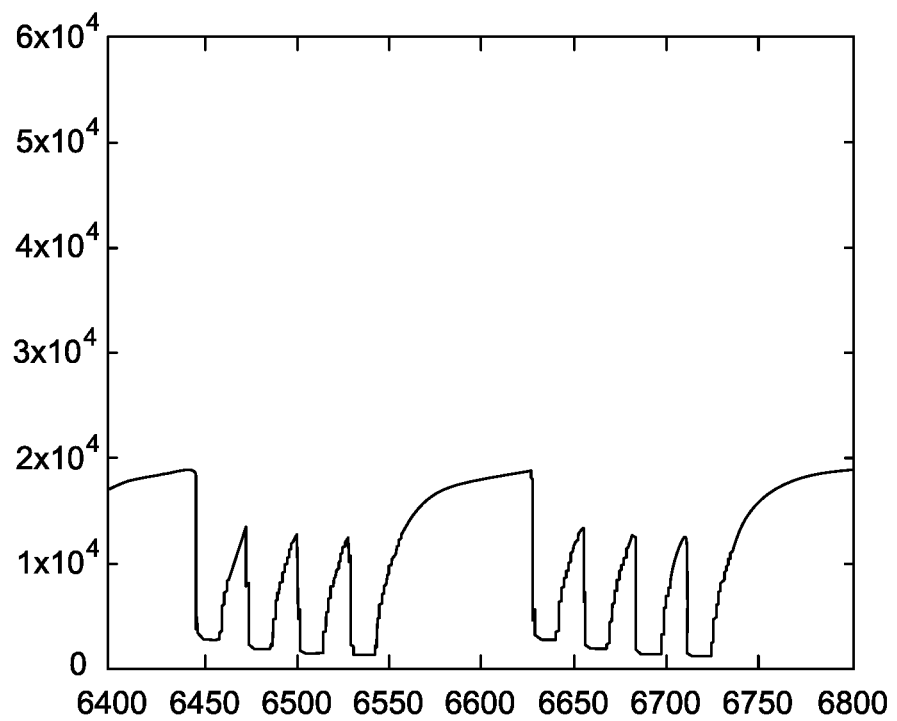
FIG. 25 illustrates additional response of a sensor probe assembly when the sensor probe assembly was tested during exposure to H2 before and after accelerated aging steps.
Figure 26:
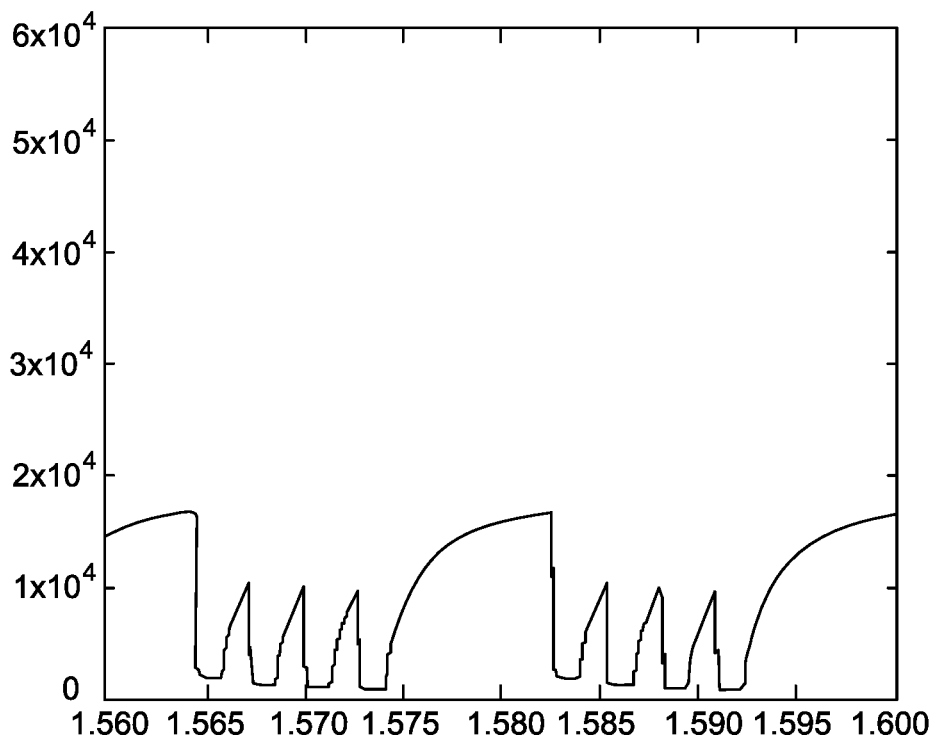
FIG. 26 illustrates additional response of a sensor probe assembly when the sensor probe assembly was tested during exposure to H2 before and after accelerated aging steps.

FIGS. 23 through 26 illustrate responses of the sensor probe assembly when the sensor probe assembly may be tested during exposure to H2 before and after the accelerated aging steps described above. Before aging, the sensor probe assembly had a response to 0-200 ppm of H2 that was significantly decreased after aging. FIG. 23 illustrates the sensor response with no aging of the sensor probe assembly, FIG. 24 illustrates the sensor response with aging of the sensor probe assembly for fifteen minutes in silicone vapor, FIG. 25 illustrates the sensor response with aging of the sensor probe assembly for sixty minutes in silicone vapor, and FIG. 26 illustrates the sensor response with aging of the sensor probe assembly for ninety minutes in silicone vapor. The concentrations of H2 were 50, 100, 150, and 200 ppm. The sensor response was collected by using an impedance analyzer at 1.5 kHz.

Figure 27:
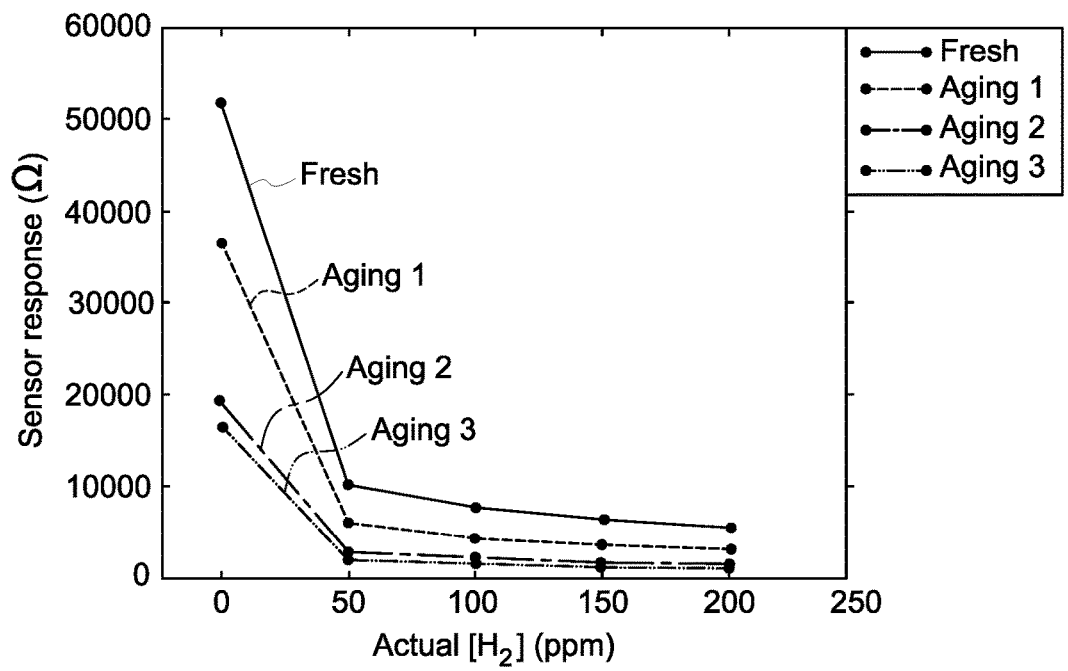
FIG. 27 depicts calibration curves of the response of the sensor probe assembly when the sensor probe assembly was tested H2 before and after the accelerated aging steps.

FIG. 27 depicts calibration curves of the response of the sensor probe assembly when the sensor probe assembly was tested H2 before and after the accelerated aging steps. The calibration curves may be significantly affected by the aging of the sensor probe assembly, as shown by the decreasing magnitudes of the sensor response with increased aging. The different calibration curves may be associated with aging of the sensor probe assembly by zero minutes (or no aging, referred to as "fresh" in FIG. 27), fifteen minutes ("aging 1" in FIG. 27), sixty minutes ("aging 2" in FIG. 27), or ninety minutes ("aging 3" in FIG. 27).

Figure 28:
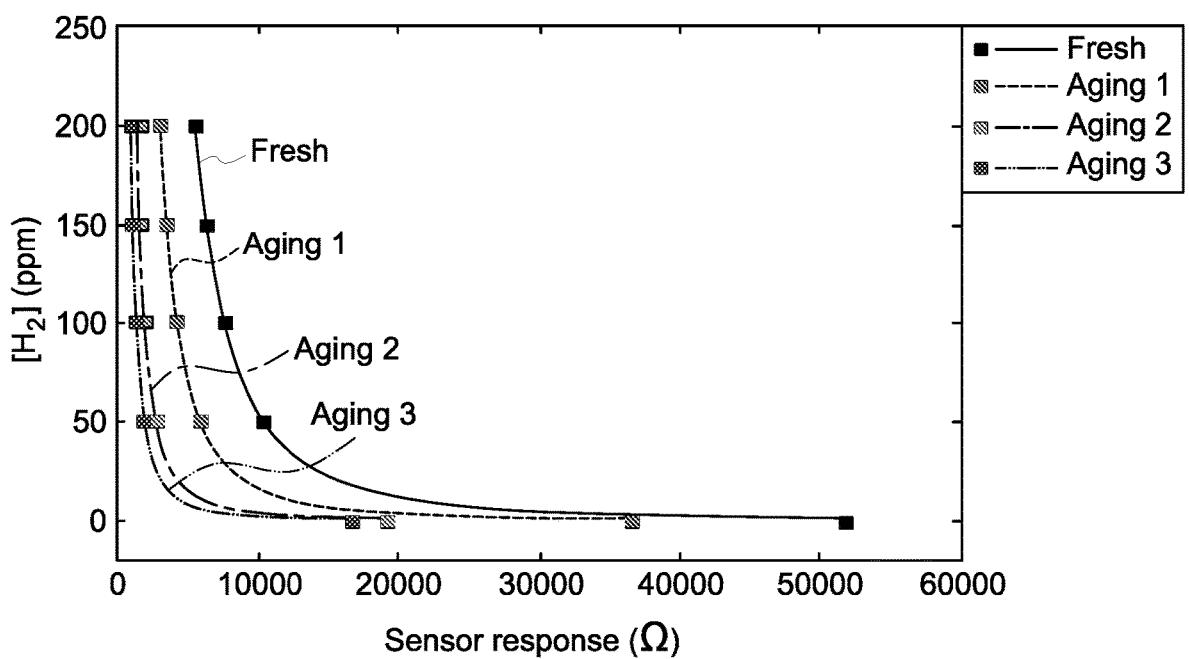
FIG. 28 illustrates responses of the sensor probe assembly to H2 at 1.5 kHz at various H2 concentrations.

FIG. 28 illustrates responses of the sensor probe assembly to H2 at 1.5 kHz at various H2 concentrations. The data shown in FIG. 28 may have been fit with power law fits as:

$$[H2, ppm] = A * Z_{ON}^B$$

The coefficients A and B of the fits are presented in Table 1 below. These coefficients may be related to the changes of the sensor response upon sensor aging.

TABLE 1

| Sensor condition | Coefficient A | Coefficient B |
| --- | --- | --- |
| fresh | 3.46e+10 | −2.20e+00 |
| After aging 1 | 6.22e+09 | −2.14e+00 |
| After aging 2 | 4.12e+08 | −2.00e+00 |
| After aging 3 | 1.53e+08 | −1.96e+00 |

Figure 29:
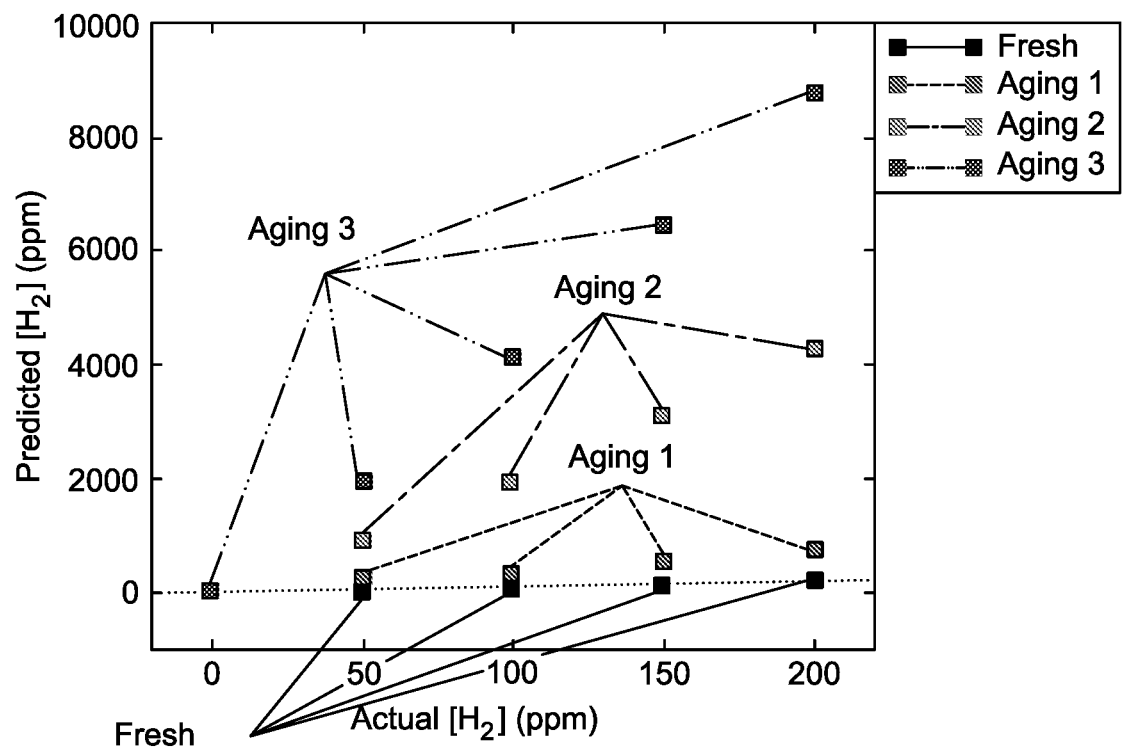
FIG. 29 depicts use of a transfer function developed for a fresh sensor probe assembly (with no aging)
Figure 30:
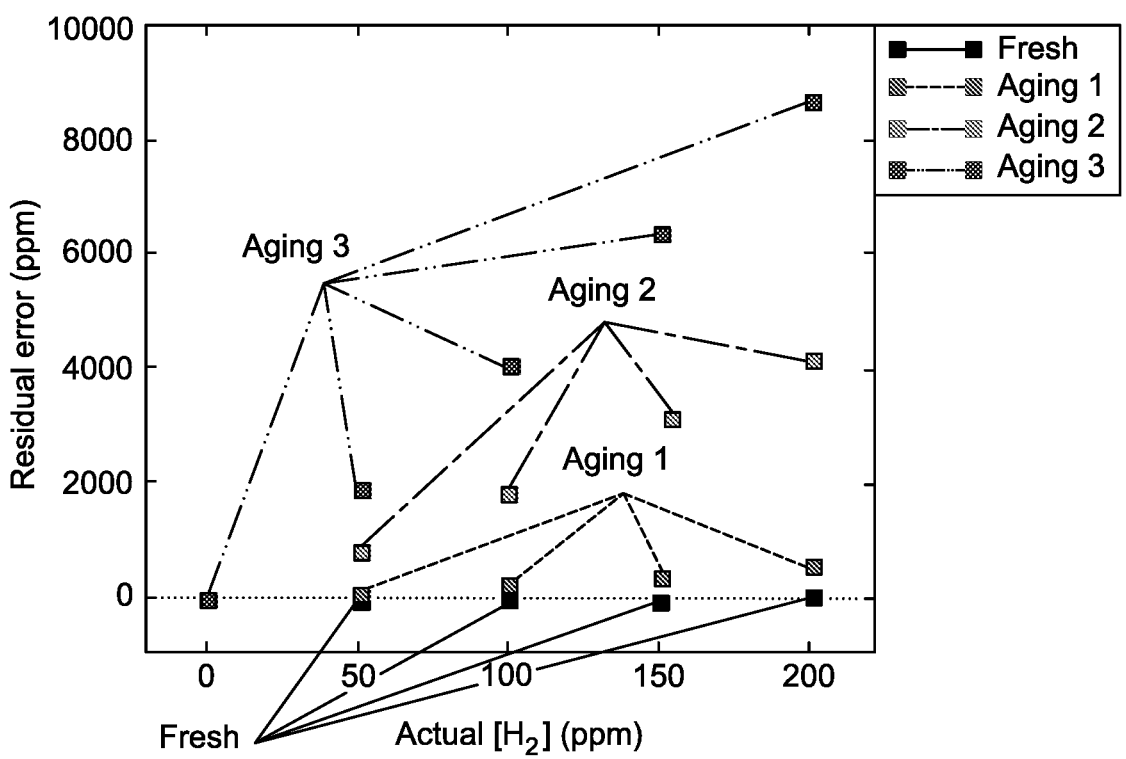
FIG. 30 also depicts use of a transfer function developed for a fresh sensor probe assembly (with no aging)

FIGS. 29 and 30 depict the use of a transfer function developed for a fresh sensor probe assembly (with no aging). FIG. 29 illustrates the correlation plot of the actual versus predicted analyte concentrations measured by the sensor probe assembly, and FIG. 30 illustrates the residual error plot for the sensor responses. This transfer function may be used for the response of the fresh sensor probe assembly and also may be applied the responses of aged sensor probe assemblies after different aging. The predicted concentrations of H2 may have significant errors shown in the correlation plot of the actual vs predicted H2 concentrations (FIG. 29) and as the residual error plot (FIG. 30).

Figure 31:
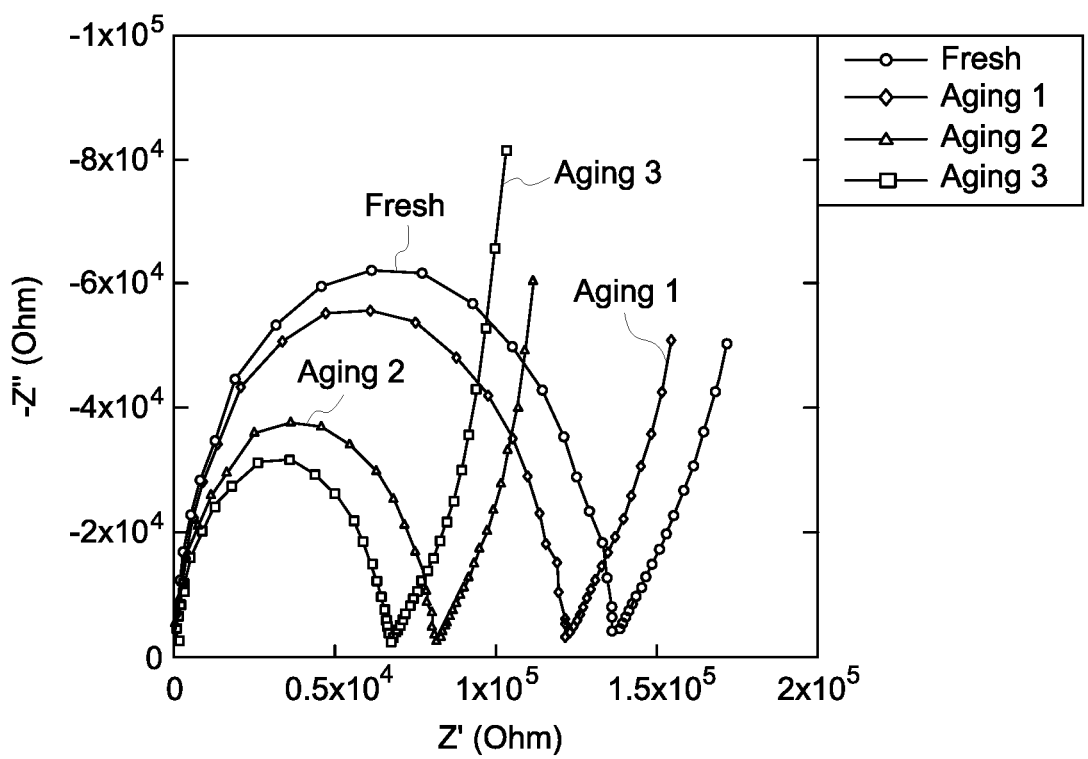
FIG. 31 illustrates a Nyquist plot of the response of the sensor probe assembly before and after three phases of aging.

FIG. 31 illustrates a Nyquist plot of the response of the sensor probe assembly before and after three phases of aging. This plot shows the sensor responses with no aging ("fresh"), with aging of fifteen minutes ("aging 1"), sixty minutes ("aging 2"), and ninety minutes ("aging 3"), as also shown in the other Figures. The aging correction of the sensor response may be completed by measuring the impedance response of the sensor probe assembly when the sensor probe assembly was OFF. The Nyquist plot demonstrates the monotonic change in the spectral properties of the sensor probe assembly while the assembly is OFF. These spectral properties may be utilized for the correction of the loss of sensor sensitivity to H2 upon aging.

Figure 32:
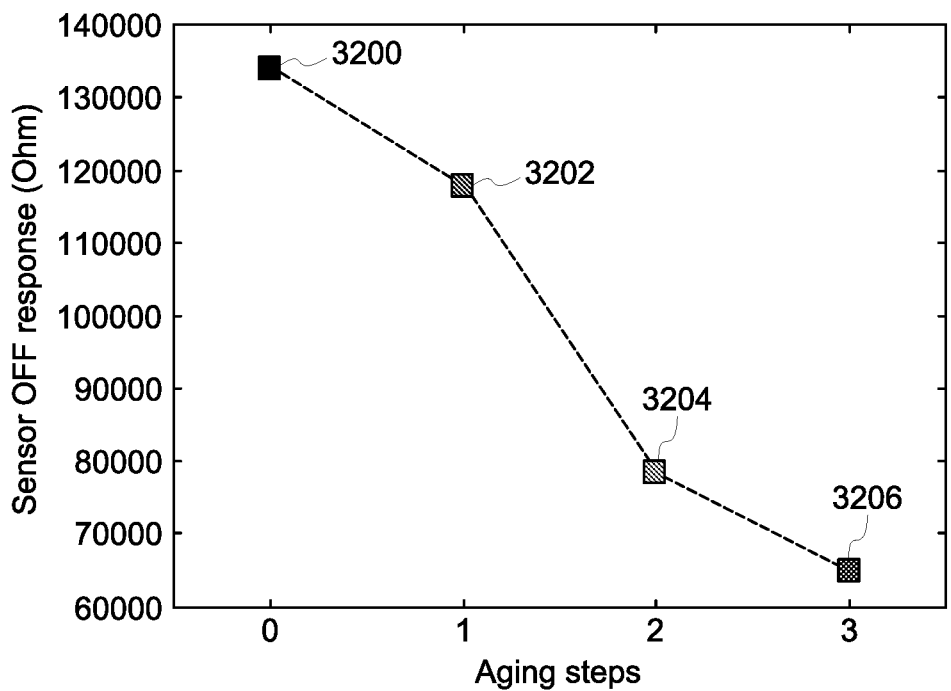
FIG. 32 illustrates the decrease of the sensor response at 100 kHz when the sensor probe assembly was OFF as a function of sensor aging.

Correction of the sensor response for aging effects may be performed by selecting a frequency of 100 kHz when the sensor probe assembly was OFF and using the sensor values at that frequency in a transfer function. FIG. 32 illustrates the decrease of the sensor response at 100 kHz when the sensor probe assembly was OFF as a function of sensor aging. Different data points 3200, 3202, 3204, 3206 represent different amounts of aging of the sensor probe assembly, with the data point 3200 representing no aging, the data point 3202 representing aging of fifteen minutes, the data point 3204 representing aging of sixty minutes, and the data point 3206 representing aging of ninety minutes.

These transfer functions for the performance of the sensor probe assembly in H2 responses may be further combined with the sensor signal when the sensor probe assembly was powered OFF. The transfer function that included the sensor OFF signal was given by:

$$[H2, ppm] = A_{ON,OFF} * Z_{ON}^{B_{ON,OFF}}$$

Figure 33:
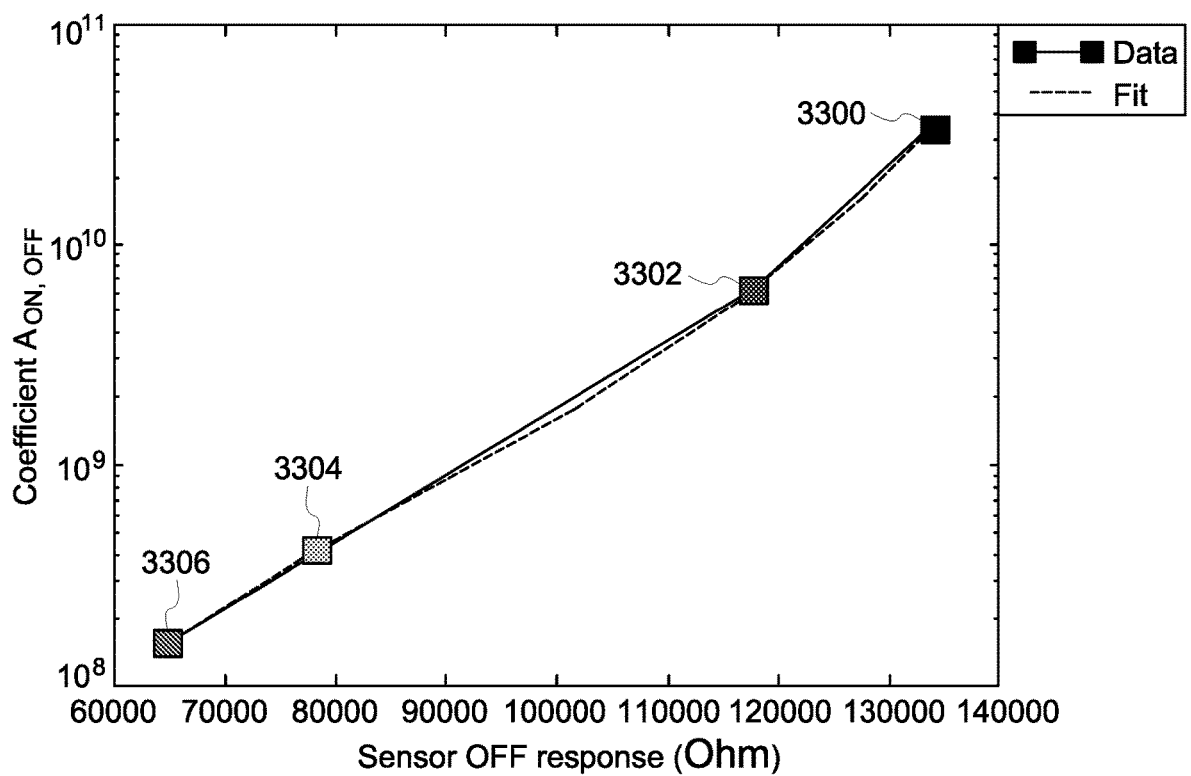
FIG. 33 illustrates the coefficients $A_{ON,OFF}$.
Figure 34:
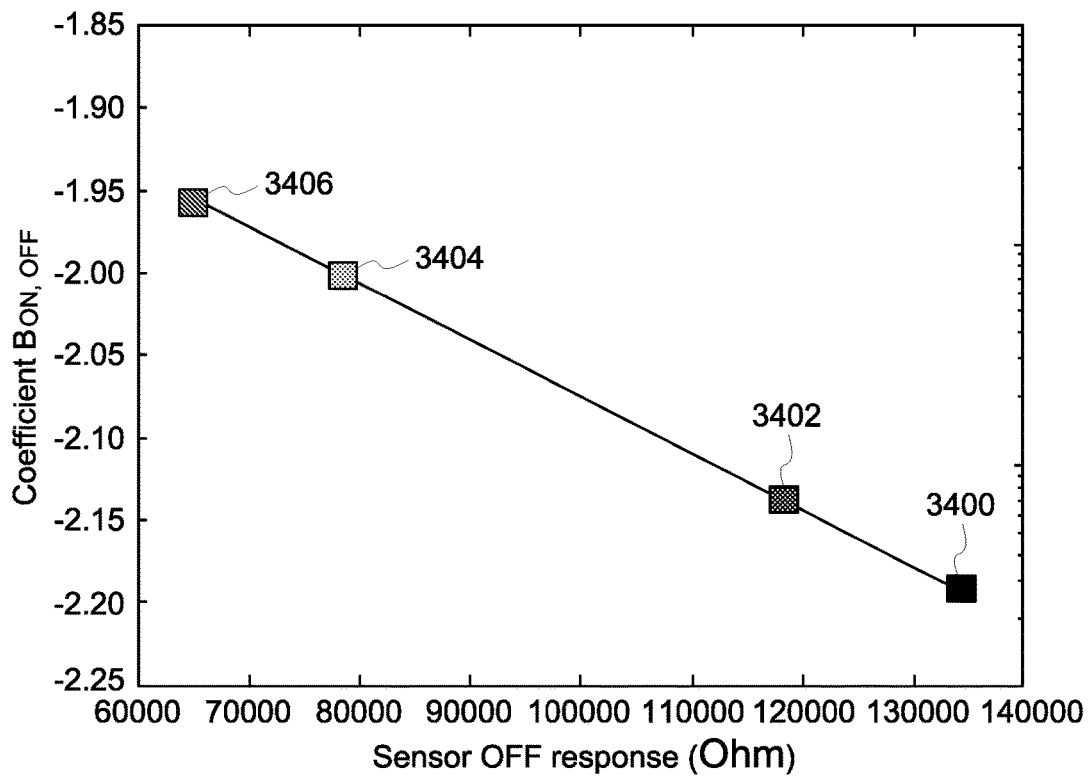
FIG. 34 illustrates the coefficients $B_{ON,OFF}$.

The coefficients $A_{ON, OFF}$ and $B_{ON, OFF}$ of the response to H2 (when the sensor probe assembly is in the ON state, as shown in FIG. 28) may be correlated to sensor aging (as determined from the sensor OFF state, as shown in FIG. 32). This correlation may be determined by plotting the values of coefficients A or B as a function of the sensor OFF response as depicted in FIGS. 33 and 34. FIGS. 33 and 34 may represent the correlation of power law coefficients $A_{ON, OFF}$ and $B_{ON, OFF}$ of the sensor response to H2 (when the sensor in the ON state) to sensor aging (as determined from the sensor OFF state). FIG. 33 illustrates the coefficients $A_{ON,OFF}$ and FIG. 34 illustrates the coefficients $B_{ON,OFF}$. Each of FIGS. 33 and 34 may include several data points 3300, 3302, 3304, 3306 (FIG. 33) and 3400, 3402, 3404, 3406 (FIG. 34) may represent different amounts of aging of the sensor probe assembly, with the data points 3300, 3400 representing no aging, the data points 3302, 3402 representing aging of fifteen minutes, the data points 3304, 3404 representing aging of sixty minutes, and the data points 3306, 3406 representing aging of ninety minutes. The coefficient $A_{ON, OFF}$ may be fit with an exponential function and the coefficient $B_{ON, OFF}$ may be fit with a linear function as a function of sensor aging using sensor OFF responses $Z_{OFF}$.

The fit coefficients included in the responses of the sensor OFF state may be defined as follows:

$$A_{ON,OFF} = e^{A_1 \cdot Z_{OFF} + A_2 \cdot Z_{OFF}^2 + A_3 \cdot OFF^3 + A_4}$$

$$B_{ON,OFF} = B_1 \cdot Z_{OFF} + B_2$$

where $A_1 = 3.30e-04$, $A_2 = -2.98e-09$, $A_3 = 1.11e-14$, $A_4 = 6.96e+00$, $B_1 = -3.43e-06$, and $B_2 = -1.74e+00$.

Figure 35:
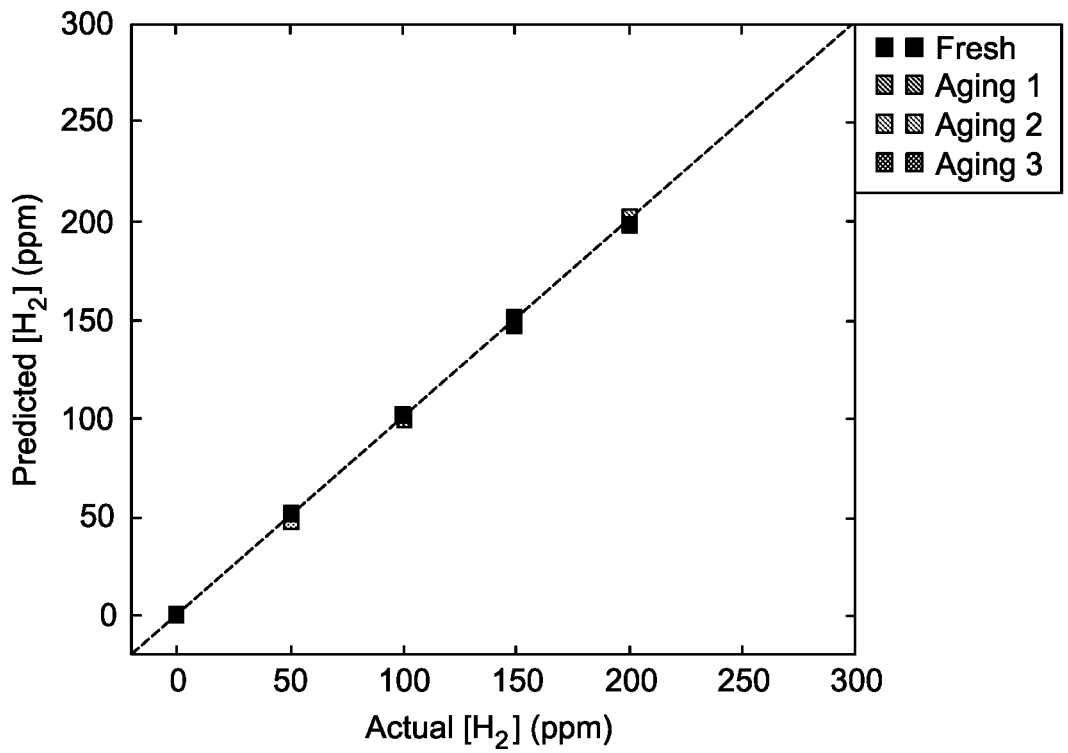
FIG. 35 depicts one example of a prediction ability of the sensor probe assembly upon aging when the new transfer function of the inventive subject matter described herein is applied.
Figure 36:
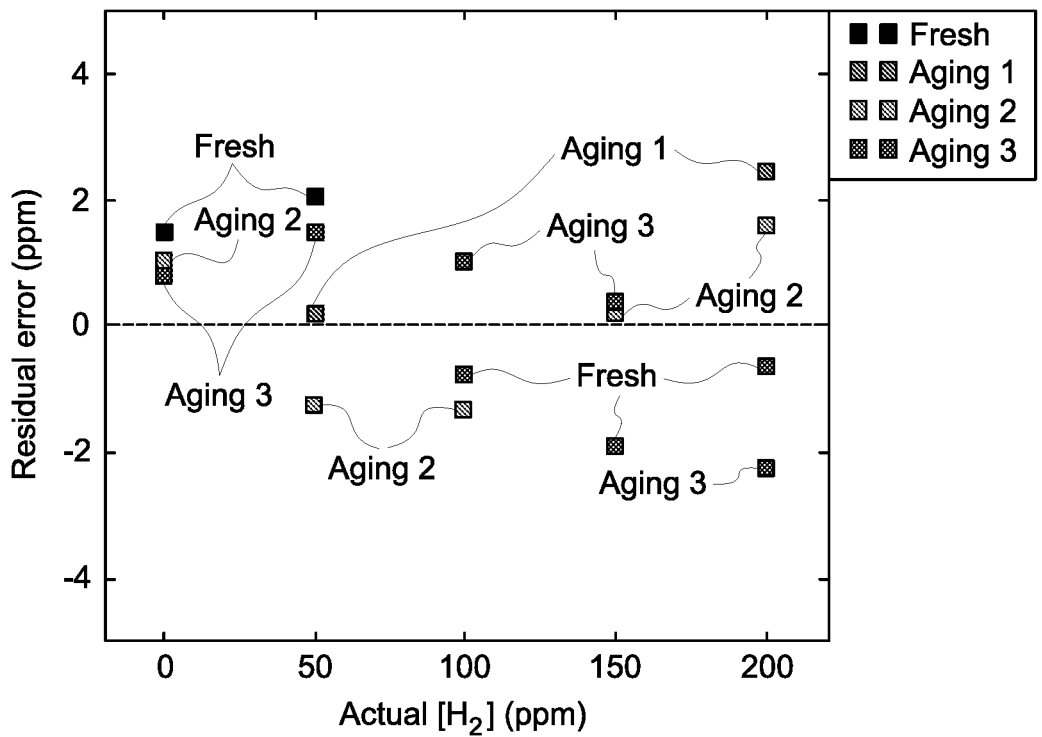
FIG. 36 depicts one example of a prediction ability of the sensor probe assembly upon aging when the new transfer function of the inventive subject matter described herein is applied.

FIGS. 35 and 36 depict one example of a prediction ability of the sensor probe assembly upon aging when the new transfer function of the inventive subject matter described herein may be applied. FIG. 35 is a correlation plot between the actual and predicted H2 concentrations for the sensor probe assembly before and after three steps of aging. FIG. 36 may be residual errors of predicted H2 concentrations for the sensor probe assembly before and after three steps of aging. The correlation plot between the actual and predicted H2 concentrations for the sensor probe assembly before and after three steps of aging may be presented in FIG. 35. The residual errors of predicted H2 concentrations for the sensor before and after three steps of aging may be presented in FIG. 36. These results illustrate that the developed concept for the correction of the sensor response upon aging significantly may improve sensor performance.

In another experiment, a SnO2 sensor probe assembly may be aged by exposing the sensor to oil. The sensor may be designed to respond to hydrogen gas. Thus, the sensor may be exposed to several concentrations of H2 gas before and after aging. Exposure to oil may be performed when the sensor was in the OFF state. The exposure may be performed by applying 10 microliters of oil onto the sensor when the sensor was OFF, waiting the oil to spread on the sensor surface and evaporating the oil by turning the sensor ON.

Figure 37:
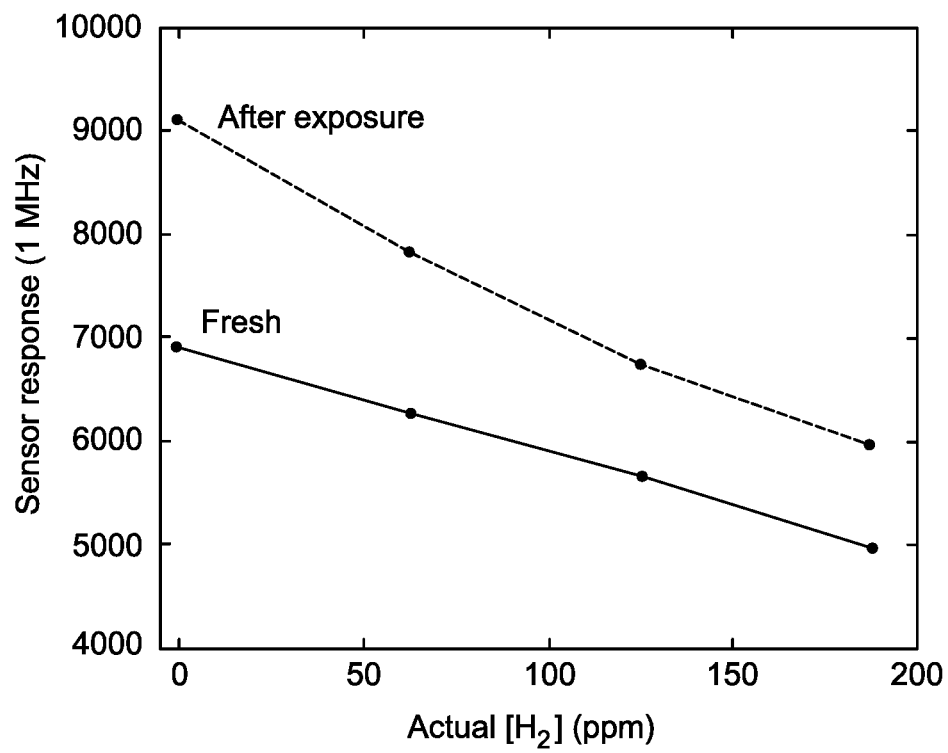
FIG. 37 illustrates the response of the sensor operated in an impedance mode (at 1 MHz, showing the measured imaginary part of the impedance) when the sensor was tested for the sensor response to hydrogen before and after the accelerated aging step.

FIG. 37 illustrates the response of the sensor operated in an impedance mode (at 1 MHz, showing the measured imaginary part of the impedance) when the sensor was tested for the sensor response to hydrogen before and after the accelerated aging step. Before aging, the sensor may have a response to H2 that may be significantly modified after aging.

Figure 38:
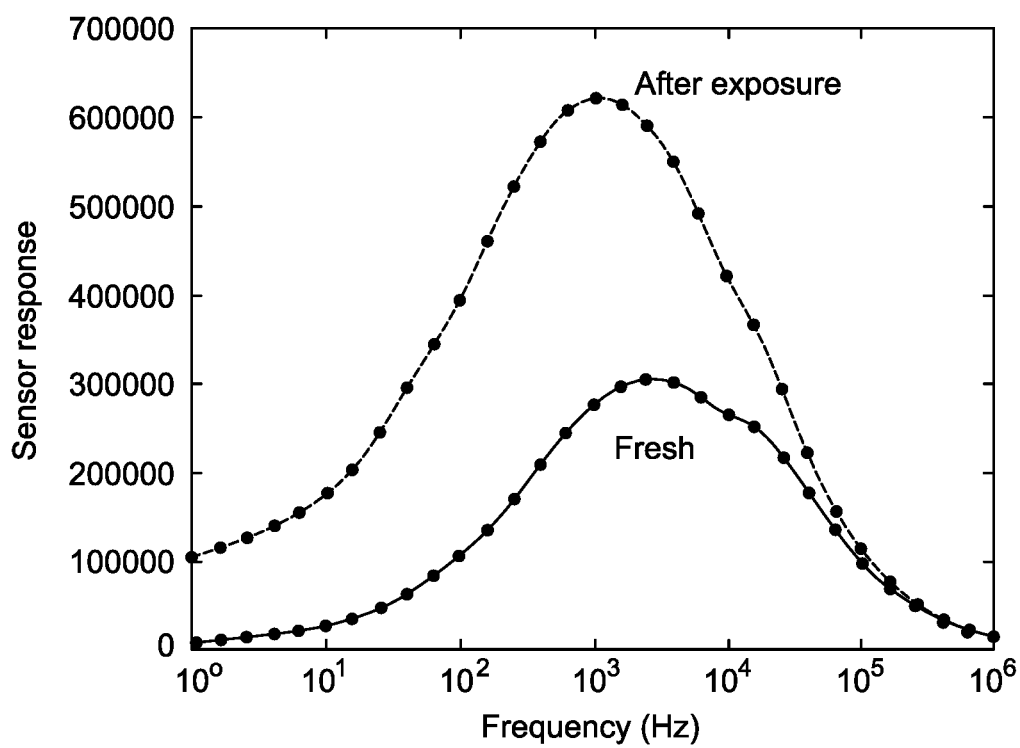
FIG. 38 illustrates the response of the sensor to the ambient environment when the sensor operated in the impedance mode over the range of frequencies from 1 Hz to 1 MHz (with the imaginary part of impedance being measured) when the sensor was tested in ambient air before and after the accelerated aging step.

FIG. 38 illustrates the response of the sensor to the ambient environment when the sensor operated in the impedance mode over the range of frequencies from 1 Hz to 1 MHz (with the imaginary part of impedance being measured) when the sensor may be tested in ambient air before and after the accelerated aging step. This response may illustrate the frequency range at about 100 to 10,000 Hz where the sensor may have the largest response before and after aging.

Figure 39:
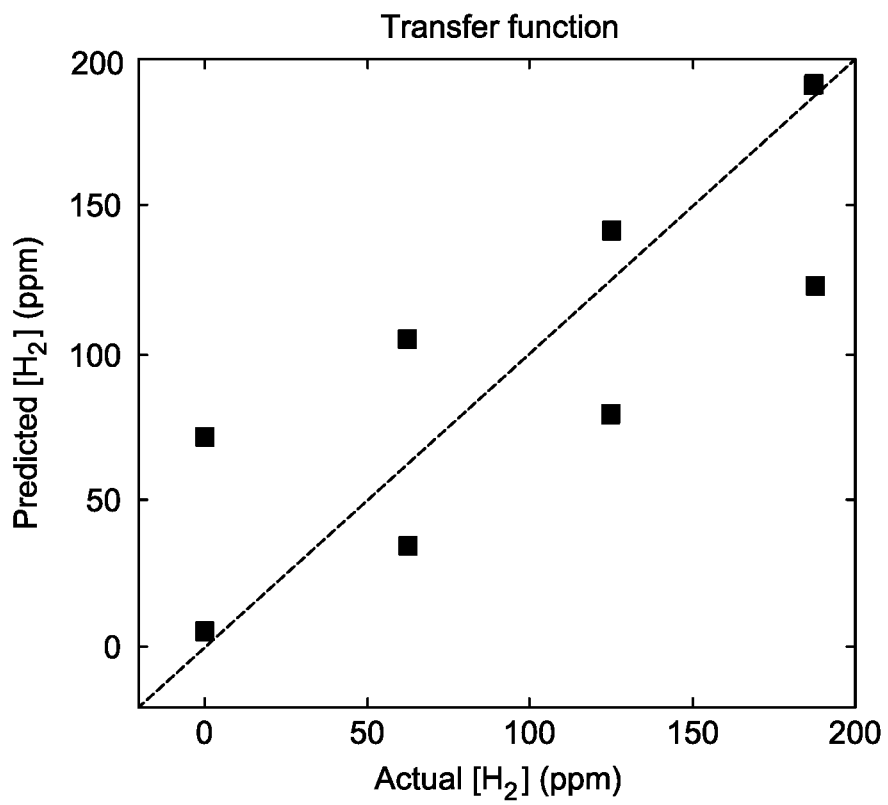
FIG. 39 depicts the response of the sensor to hydrogen when operated in the impedance mode before and after the accelerated aging step and without correction of sensor response when the sensor was in the OFF state.
Figure 40:
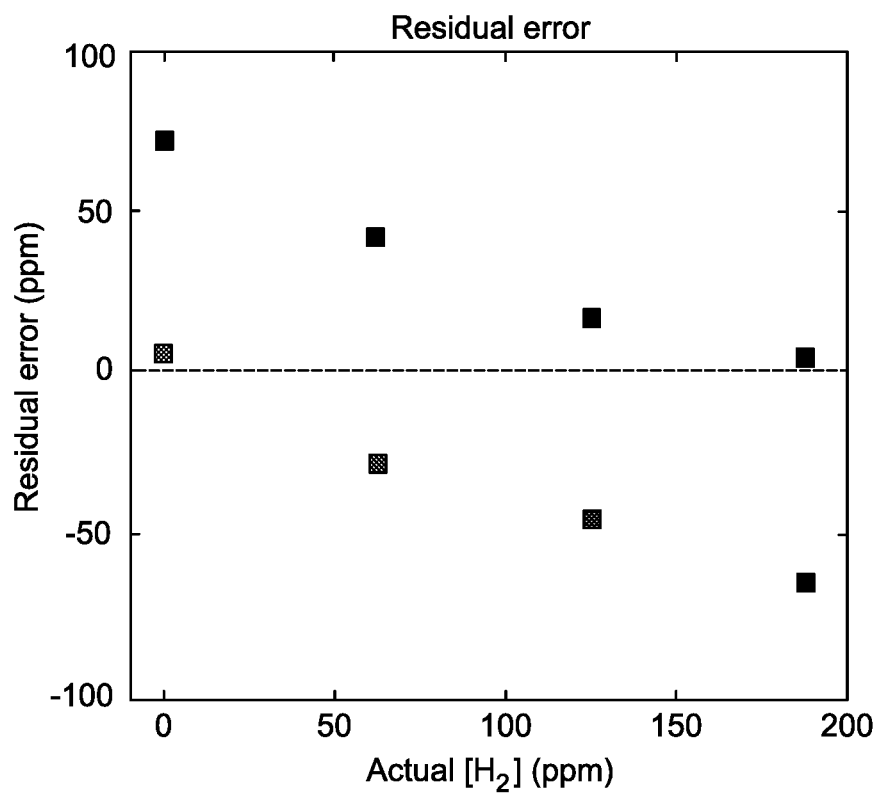
FIG. 40 depicts the response of the sensor to hydrogen when operated in the impedance mode before and after the accelerated aging step and without correction of sensor response when the sensor was in the OFF state.

FIGS. 39 and 40 depict the response of the sensor to hydrogen when operated in the impedance mode before and after the accelerated aging step and without correction of sensor response when the sensor was in the OFF state. FIG. 39 depicts the predicted vs actual concentrations of hydrogen gas before and after the accelerated aging step and without correction of sensor response showing a large spread in predicted values. FIG. 40 depicts the residual error of predictions of concentrations of hydrogen gas before and after the accelerated aging step and without correction of sensor response showing a large spread in residual error values.

Figure 41:
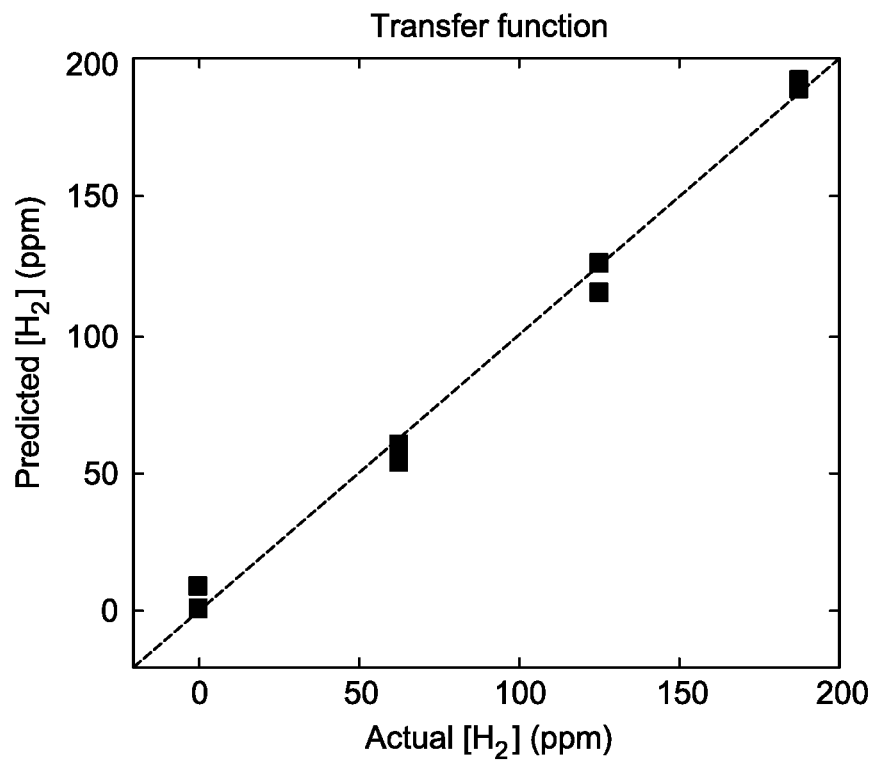
FIG. 41 illustrates predicted versus actual concentrations of hydrogen gas before and after the accelerated aging step and with correction of sensor response showing a relatively small spread in predicted values.
Figure 42:
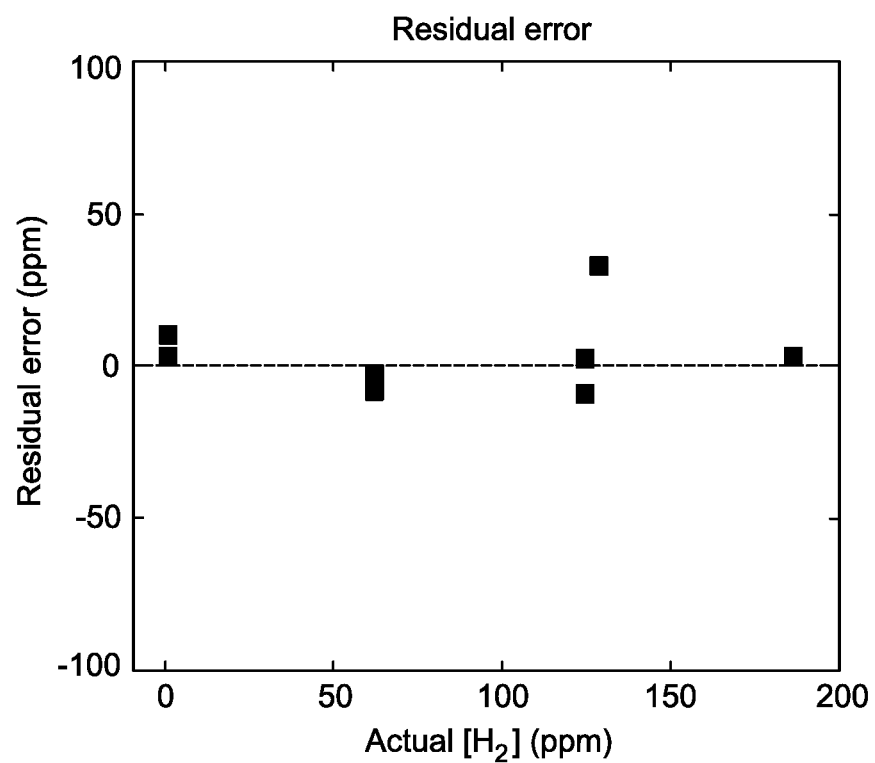
FIG. 42 illustrates residual error of predictions of concentrations of hydrogen before and after an accelerated aging step and with correction of sensor response showing a relatively small spread in residual error values.

FIGS. 41 and 42 illustrate a response of the sensor probe assembly to hydrogen when operated in impedance mode before and after the accelerated aging step with correction of sensor response when the sensor was in OFF state. FIG. 41 illustrates predicted versus actual concentrations of hydrogen gas before and after the accelerated aging step and with correction of sensor response showing a relatively small spread in predicted values. FIG. 42 illustrates residual error of predictions of concentrations of hydrogen before and after accelerated aging step and with correction of sensor response showing a relatively small spread in residual error values.

Figure 43:
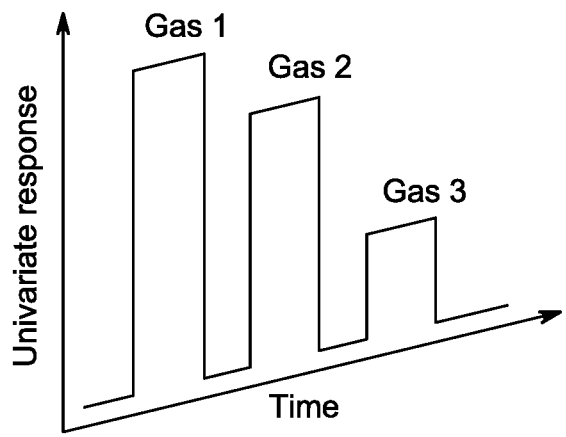
FIG. 43 illustrates a schematic of responses from a conventional sensor to diverse gases that produce only different response magnitudes.
Figure 44:
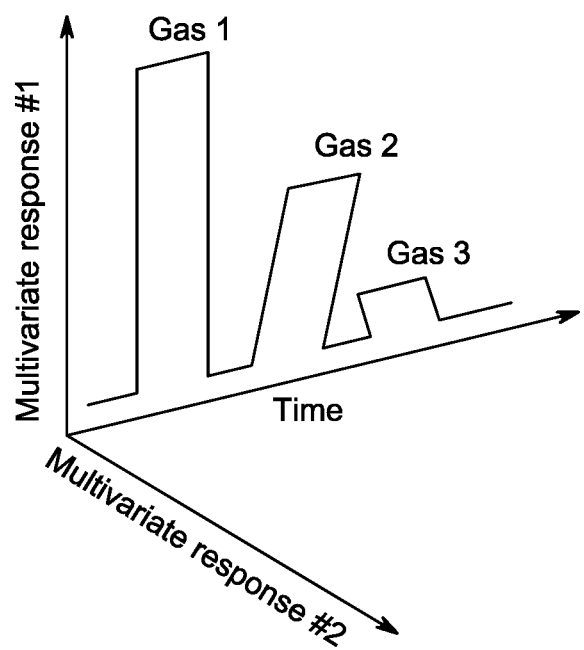
FIG. 44 depicts a schematic of discrimination of gases using a multivariable gas sensor, where the discrimination of gases is not completely orthogonal.
Figure 45:
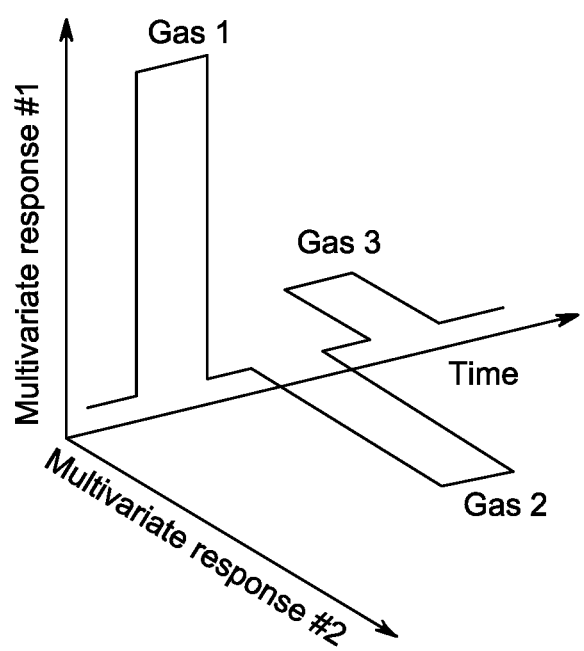
FIG. 45 depicts a schematic of approach of one embodiment of the inventive subject matter described herein for improved orthogonality of response of a multivariable sensor to gases of interest.

Expanding orthogonality of multivariable sensor response can be important in achieving reliable discrimination of different fluids and predicting concentrations of individual fluids in their mixtures. For example, conventional sensors may not discriminate different gases because of the nature of the single-output design principles of the conventional sensors. FIG. 43 illustrates a schematic of responses from a conventional single-output sensor to diverse gases where a conventional single-output sensor produces only different response magnitudes to diverse gases. Thus, when diverse gases are measured at their various concentrations using a conventional single-output sensor, same response magnitudes may be obtained without providing any information about was the particular gas that produced such response. Discrimination of gases can be achieved using multivariable sensors. FIG. 44 depicts a schematic of discrimination of gases using a multivariable gas sensor, where the discrimination of gases may not completely orthogonal, limiting analysis of multiple individual gases or gas mixtures. One or more embodiments of the inventive subject matter described herein may improve the orthogonality of responses of a multivariable sensor to gases of interest. FIG. 45 depicts a schematic of approach of the inventive subject matter described herein for improved orthogonality of response of a multivariable sensor to gases of interest.

Figure 46:
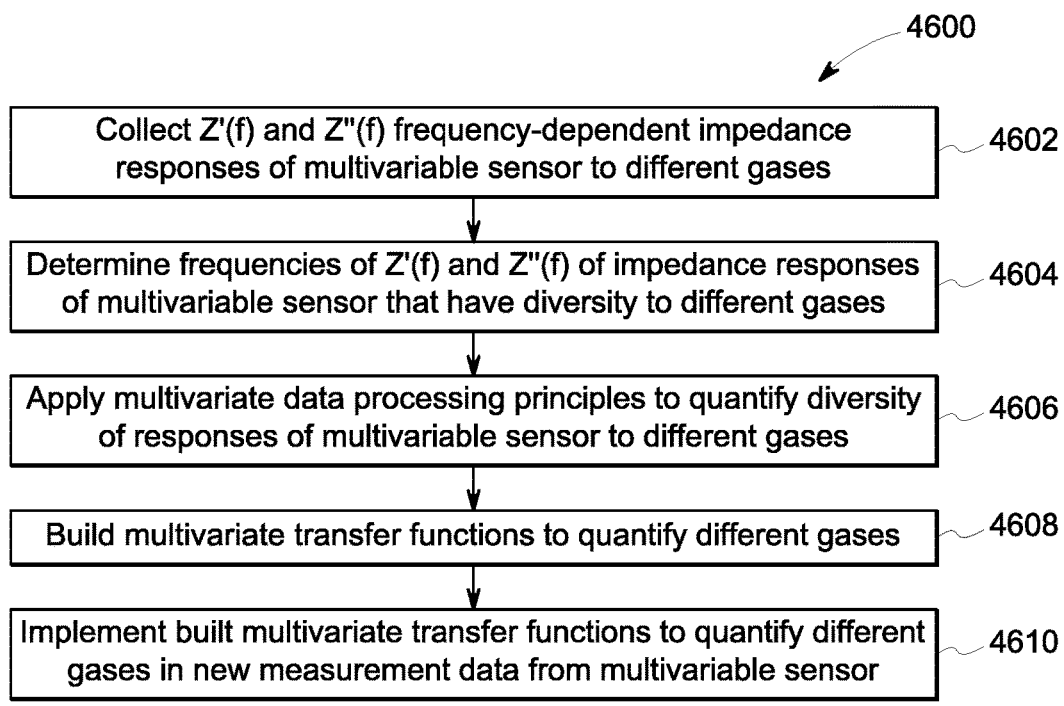
FIG. 46 illustrates one embodiment of a method for quantitation of different gases using a multivariable sensor.

In one embodiment, one embodiment of a method for quantitation of different gases using a multivariable sensor may be depicted in FIG. 46. The operations described in connection with this method can be performed partially or entirely by the data acquisition circuitry described herein. In this method, frequency-dependent impedance responses of a multivariable sensor $Z'(f)$ and $Z''(f)$ to different gases may be collected at 4602. Next, frequencies of $Z'(f)$ and $Z''(f)$ of impedance responses of a multivariable sensor may be determined that may have diversity to different gases at 4604. Next, multivariate data processing principles may be applied to quantify diversity of responses of a multivariable sensor to different gases at 4606. Next, multivariate transfer functions may be built to quantify different gases at 4608. Finally, these built multivariate transfer functions may be implemented to quantify different gases in new measurement data from this multivariable sensor at 4610.

For example, at any measured frequency f1, the multivariable sensor can have a response $Z'(f1)$ and $Z''(f1)$ to gas 1 as $Z'(gas1$ at $f1)$ and $Z''(gas1$ at $f1)$. Similarly, the multivariable sensor can have its response $Z'(f1)$ and $Z''(f1)$ to gas 2 as $Z'(gas2$ at $f1)$ and $Z''(gas2$ at $f1)$.

Response pattern of the multivariable sensor to gas 1 and gas 2 can be defined as the different ratios of responses of $Z'(f1)$ and $Z''(f1)$ such as:

$Z'(gas1$ at $f1)/Z'(gas2$ at $f1)$, or $Z'(gas1$ at $f1)/Z''(gas2$ at $f1)$, or $Z'(gas1$ at $f1)/Z''(gas2$ at $f1)$, or $Z''(gas1$ at $f1)/Z'(gas2$ at $f1)$.

Other ratios between responses are also possible, for example when the responses are combinations of more than two frequencies. If the response pattern of the multivariable sensor to gas 1 and gas 2 stays the same for all measured frequencies, this means that this multivariable sensor may not have a diversity in response to gas 1 and gas 2 and thus, gas 1 and gas 2 may not be discriminated with this multivariable sensor at these measurement conditions.

However, if the response pattern of the multivariable sensor to gas 1 and gas 2 is different for some or all measured frequencies, this may mean that this multivariable sensor may have diversity in response to gas 1 and gas 2 and these two gases can be discriminated with this multivariable sensor at these measurement conditions.

Nonlimiting examples of multivariate data processing principles may include methods to perform quantitation of gases. Nonlimiting examples of methods for performing analyte quantitation to determine the concentration of a particular analyte gas may include Principal Component Regression (PCR), Independent Component Regression (ICR), Nonlinear Regression Analysis (NRA), Discriminate Function Analysis (DFA), or Neural Network Analysis (NNA).

Figure 47:
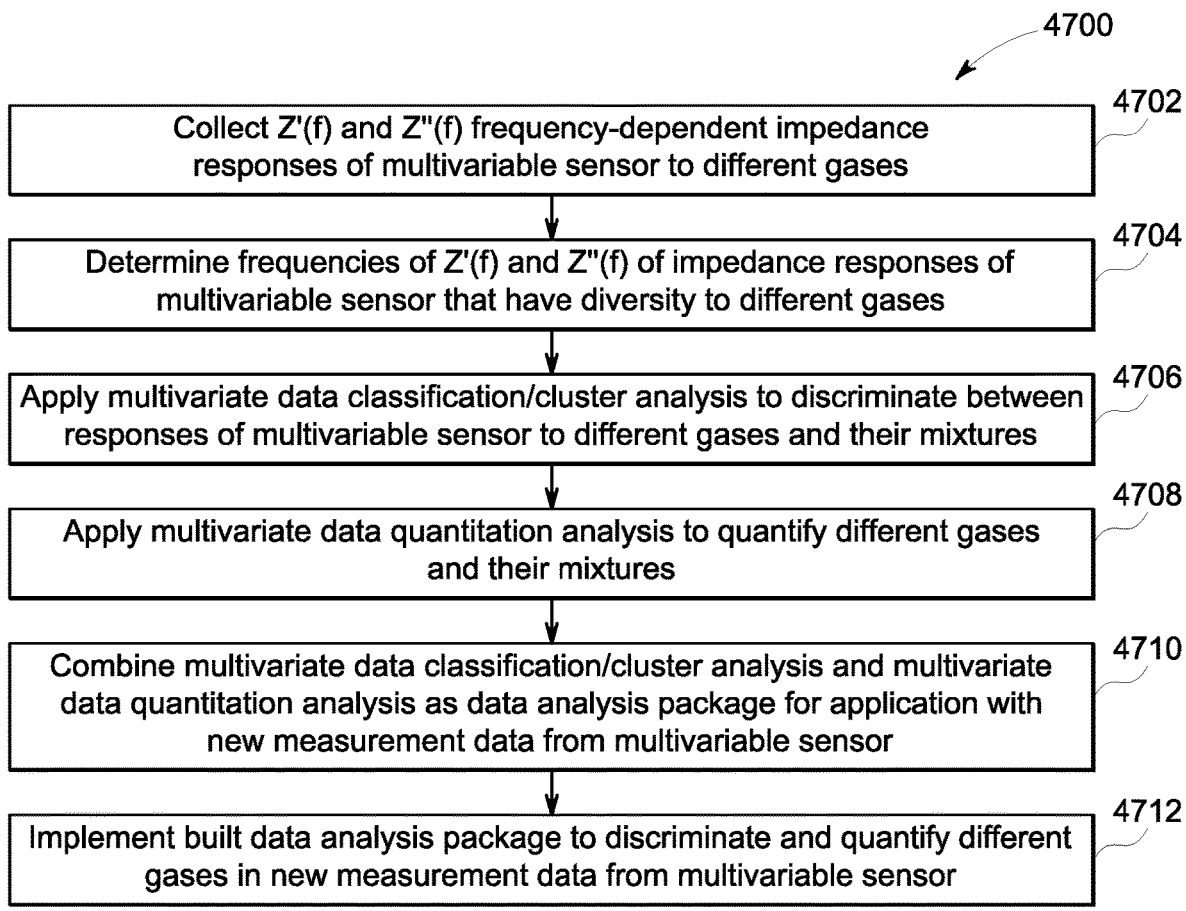
FIG. 47 illustrates one embodiment of a method for classification and quantitation of different gases using a multivariable sensor.

In one embodiment, a method for classification and quantitation of different gases using a multivariable sensor may be depicted in FIG. 47. The operations described in connection with this method can be performed partially or entirely by the data acquisition circuitry described herein. In this method, frequency-dependent impedance responses of a multivariable sensor $Z'(f)$ and $Z''(f)$ to different gases may be collected (at 4702). Next, frequencies of $Z'(f)$ and $Z''(f)$ of impedance responses of a multivariable sensor may be determined that may have diversity to different gases (at 4704). Next, multivariate data classification/cluster analysis may be applied to discriminate between responses of multivariable sensor to different gases and mixtures of the gases (at 4706). Next, multivariate data quantitation analysis may be applied to quantify different gases and mixtures of the gases (at 4708). Next, multivariate data classification/cluster analysis and multivariate data quantitation analysis may be combined to produce a data analysis package for application with new measurement data from the multivariable sensor (at 4710). Finally, the built data analysis package may be implemented to discriminate and quantify different gases in new measurement data from multivariable sensor (at 4712).

Nonlimiting examples of multivariate data processing principles may include methods to perform classification/cluster analysis and quantitation of gases. Classification/cluster analysis can be performed to correctly determine the type of the analyte gas. Quantitation can be performed to correctly determine the concentration of the analyte gas. Examples of classification/cluster analysis methods include, but are not limited, to Principal Component Analysis (PCA), Hierarchical Cluster Analysis (HCA), Independent Component Analysis (ICA), Linear Discriminant Analysis (LDA), and Support Vector Machines (SVM) algorithm. Nonlimiting examples of methods for performing analyte quantitation to determine the concentration of a particular analyte gas include Principal Component Regression (PCR) and Independent Component Regression (ICR). In certain aspects of the inventive subject matter described herein, a classification algorithm can be followed by quantitation algorithm.

Figure 48:
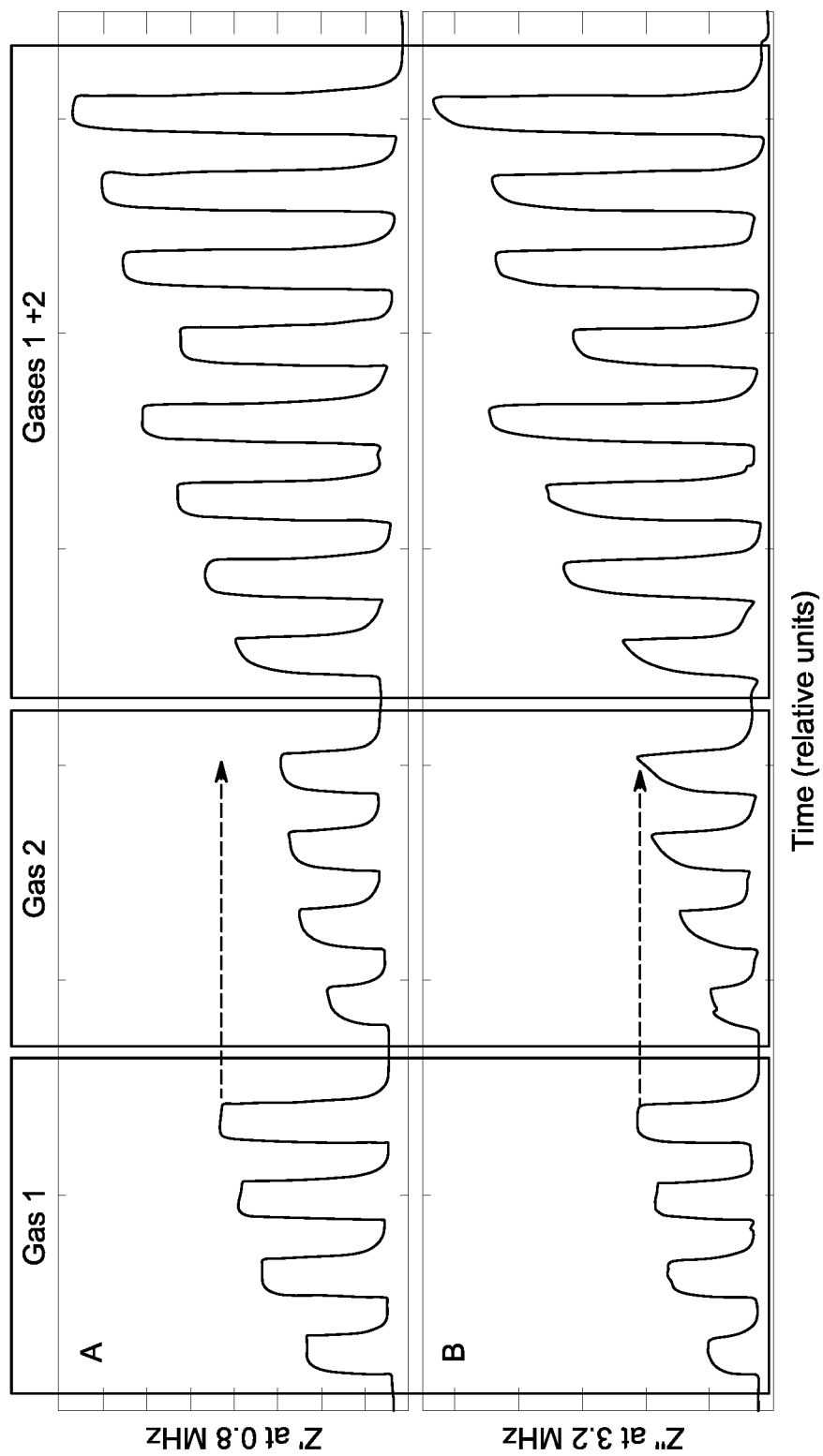
FIG. 48 illustrates an example of detection of acetylene C2H2 (gas 1) and water vapor (H2O, gas 2) and mixtures of these components using an impedance sensor according to one embodiment of the inventive subject matter described herein.

FIG. 48 illustrates an example of detection of acetylene C2H2 (gas 1) and water vapor (gas 2) and their mixtures (gas 1+2) diluted with air using an impedance sensor of this invention. The sensor may be utilized a semiconducting metal oxide as a sensing material such as tin dioxide SnO2. Using a computer-controlled gas dilution and mixing system, four concentrations of C2H2 (gas 1) may be generated such as 312.5 ppm (1), 625 ppm (2), 937.5 ppm (3), and 1250 ppm (4); four concentrations of H2O (water vapor, gas 2) may be generated such as $5.3 \times 10^3$ ppm (1), $1.1 \times 10^4$ ppm (2), $1.6 \times 10^4$ ppm (3), and $2.1 \times 10^4$ ppm (4); and eight mixtures of gas 1 and gas 2 may be generated such as:

312.5 ppm of C2H2 and $5.3 \times 10^3$ ppm of H2O (mixture 1),
312.5 ppm of C2H2 and $1.6 \times 10^4$ ppm of H2O (mixture 2),
625 ppm of C2H2 and $1.1 \times 10^4$ ppm of H2O (mixture 3),
625 ppm of C2H2 and $2.1 \times 10^4$ ppm of H2O (mixture 4),
937.5 ppm of C2H2 and $5.3 \times 10^3$ ppm of H2O (mixture 5),
937.5 ppm of C2H2 and $1.6 \times 10^4$ ppm of H2O (mixture 6),
1250 ppm of C2H2 and $1.1 \times 10^4$ ppm of H2O (mixture 7),
1250 ppm of C2H2 and $2.1 \times 10^4$ ppm of H2O (mixture 8).

Concentrations of gases may be presented to the sensor in sequence with a blank (clean air) between exposures to gases. Results depicted in FIG. 48 may illustrate detection of acetylene C2H2 and H2O and their mixtures. For example, Graph A may illustrate the sensor response Z' at 0.8 MHz and Graph B may illustrate the sensor response Z" response at 3.2 MHz. Each Graph A and Graph B may include a horizontal dotted arrow line. These lines may highlight the response magnitudes of the sensor to the highest tested C2H2 concentration and may compare these response magnitudes with the response magnitudes of the sensor to tested H2O concentrations. Graph A may demonstrate that at the illustrated frequency, Z' sensor response may have bigger magnitude to C2H2 as compared to H2O. However, as demonstrated in Graph B, at the illustrated frequency Z" sensor response may have the same magnitude to C2H2 and H2O. Thus, operation of the impedance sensor at different frequencies and detection at Z' and Z" may provide different response patterns to C2H2 and H2O and their mixtures where the relative response magnitudes to C2H2 and H2O may be varied depending on the detection frequency and Z' or Z" operation.

Figure 49:
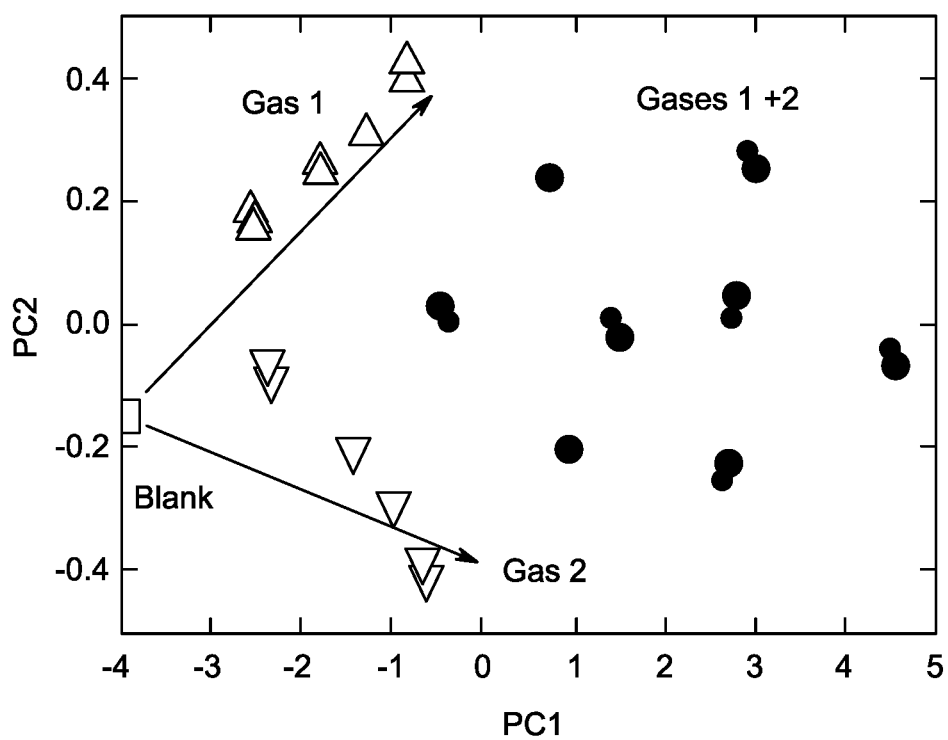
FIG. 49 depicts a scores plot of principal component 1 vs principal component 2 of a built principal component analysis model that discriminates between individual gases and mixtures of these gases based on Z' and Z" spectral features of a single multivariable sensor according to one embodiment of the inventive subject matter described herein.

Several frequencies may be used to build a multivariate model using principal components analysis (PCA) tool. PCA is a widely accepted unsupervised pattern recognition technique for classification of multivariate data. PCA may reduce a multidimensional data set for its easier interpretation. PCA may calculate orthogonal principal components (PCs) that may be oriented in the direction of the maximum variance within the data set. The first principal component may contain the highest degree of variance, and other PCs may follow in the order of decreasing variance. Thus, the PCA may concentrate the most significant characteristics (variance) of the data into a lower dimensional space. The distribution of data points in the PCA plot may allow the visualization of relations between the original impedance spectra. FIG. 49 illustrates a two-dimensional plot of a first principal component (PC1) versus a second principal component (PC2). This score plot of PCs may visualize the response pattern of the sensor to different gases and their mixtures based on their Z' and Z" spectral features. Such plot may illustrate that PCA response of a single impedance sensor based on a SnO2 sensing material starts from the response to a blank (clean air) and may be further directed into different directions that are dependent on the type of detected gas 1 and gas 2 and mixtures of gas 1 and gas 2.

Figure 50:
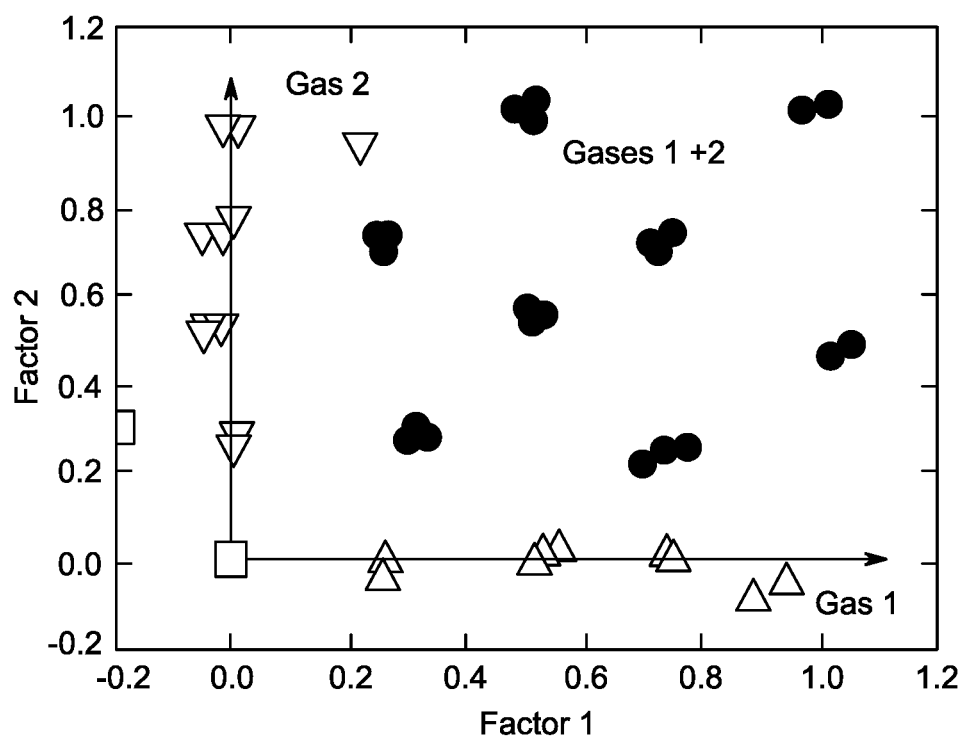
FIG. 50 depicts a plot of factor 1 vs factor 2 of the built model that produces orthogonal response to different individual gases 1 and 2 to discriminate mixtures of gases 1 and 2 with an improved linearity over principal component analysis (PCA)

FIG. 50 depicts a plot of factor 1 vs factor 2 of the built model. This plot may illustrate the ability to produce orthogonal response to different individual gases 1 and 2 to discriminate mixtures of gases 1 and 2 with an improved linearity over PCA.

Figure 51:
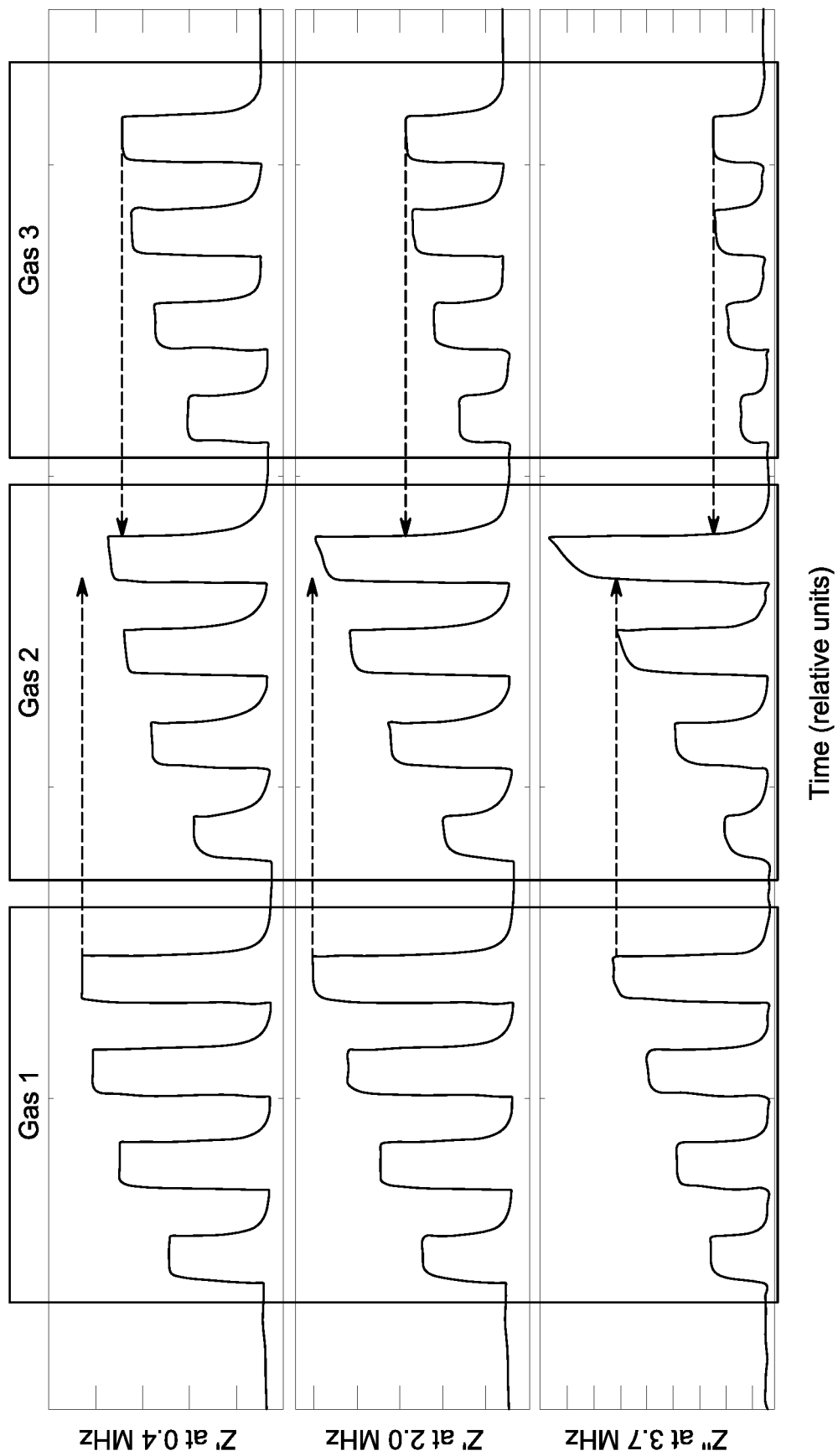
FIG. 51 illustrates an example detection of acetylene C2H2 as gas 1, hydrogen H2 as gas 2, and methane CH4 as gas 3 using one embodiment of an impedance sensor of the inventive subject matter described herein.

FIG. 51 illustrates an example of detection of three gases with a single multivariable sensor. The sensor may utilize a semiconducting metal oxide such as tin dioxide SnO2 as a sensing material. The example gases may be acetylene C2H2 as gas 1, hydrogen H2 as gas 2, and methane CH4 as gas 3. Using a computer-controlled gas dilution and mixing system, four concentrations of each gas may be generated.

Gas 1 may have concentrations 1042 ppm (1), 2083 ppm (2), 3125 ppm (3), and 4167 ppm (4). Gas 2 may have concentrations 4 ppm (1), 8 ppm (2), 13 ppm (3), and 17 ppm (4).

Gas 3 may have concentrations 2083 ppm (1), 4167 ppm (2), 6250 ppm (3), and 8333 ppm (4).

Gas concentrations may be presented to the sensor in sequence with a blank (clean air) between exposures to gases. Graph A illustrates the sensor response Z' at 0.4 MHz, Graph B illustrates the sensor response Z' at 2.0 MHz, and Graph C illustrates the sensor response Z" at 3.7 MHz. Each Graph A through C may include two horizontal dotted arrow lines. Left lines may go from gas 1 to gas 2 to highlight the response magnitude of the sensor to the highest tested concentration of gas 1 and may compare this response magnitude with the response magnitude of the sensor to tested concentrations of gas 2. Right lines may go from gas 3 to gas 2 to highlight the response magnitude of the sensor to the highest tested concentration of gas 3 and may compare this response magnitude with the response magnitude of the sensor to tested concentrations of gas 2.

Graph A may demonstrate that at the illustrated frequency, Z' sensor response to gas 1 may have approximately similar magnitude as compared to response magnitude to gas 2 and sensor response to gas 3 may have approximately similar magnitude as compared to response magnitude to gas 2. Graph B may demonstrate that at the illustrated frequency, Z' sensor response to gas 1 may have approximately similar magnitude as compared to response magnitude to gas 2 and sensor response to gas 3 may have smaller magnitude as compared to response magnitude to gas 2. Graph C may demonstrate that at the illustrated frequency, Z' sensor response to gas 1 may have smaller magnitude as compared to response magnitude to gas 2 and sensor response to gas 3 may have smaller magnitude as compared to response magnitude to gas 2. Thus, operation of the impedance sensor at different frequencies and detection at Z' and Z" may provide different response patterns to gas 1, gas 2, and gas 3 where the relative response magnitudes to gas 1, gas 2, and gas 3 may be varied depending on the detection frequency and Z' or Z" operation.

As shown in FIG. 51, the sensor responses to gas 1, gas 2, and gas 3 may have different relative magnitudes with respect to each other as illustrated at different frequencies and as measured as Z' or Z". To visualize this frequency dependence of sensor responses to gas 1, gas 2, and gas 3, correlation matrices may be created with rows and columns that may be frequencies of Z" responses of the sensor. These correlation matrices may be depicting difference of the sensor responses between pairs of gases such as gas 1 vs gas 2, gas 1 vs gas 3, and gas 2 vs gas 3. The frequencies may be from 100 Hz to about 10 MHz with the total number of 75 frequencies. The color maps may be visualizing regions of response difference of the sensor between pairs of gases such as gas 1 vs gas 2, gas 1 vs gas 3, and gas 2 vs gas 3. Regions without significant response difference may have values of about zero, while regions with significant response difference may have values from about 0.5 to about unity.

Figure 52:
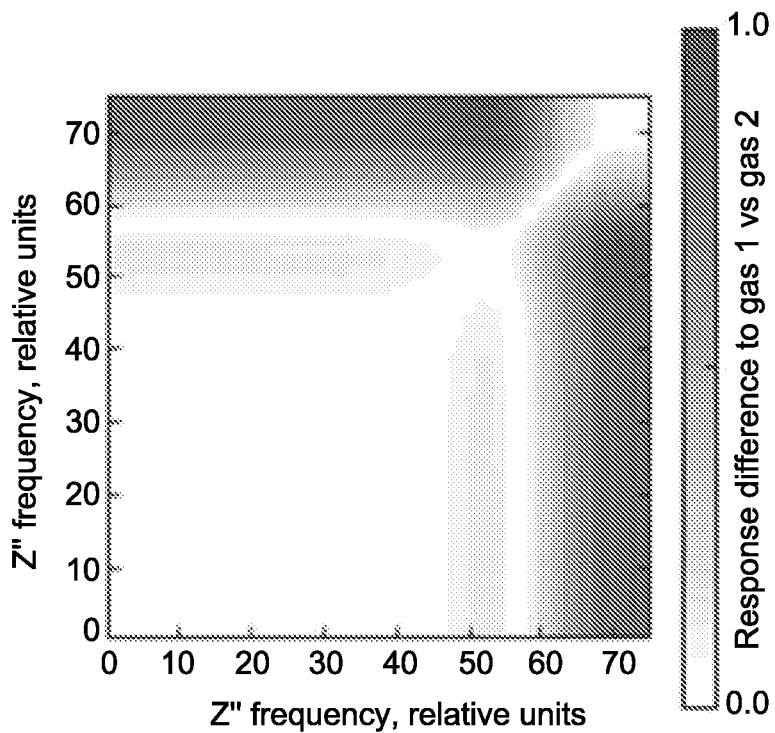
FIG. 52 illustrates a correlation matrix of the sensor response to gas 1 in relation to the sensor response to gas 2.

FIG. 52 illustrates a correlation matrix that depicts the diversity of the sensor response at different frequencies to gas 1 in relation to the sensor response at different frequencies to gas 2. The map may visualize regions of response difference for pairs of frequencies. The significant response difference of the sensor between gas 1 vs gas 2 may be observed when the region of frequencies starting from about frequency 65 to about frequency 75 may be paired with the region of frequencies starting from about frequency 1 to about frequency 60.

Figure 53:
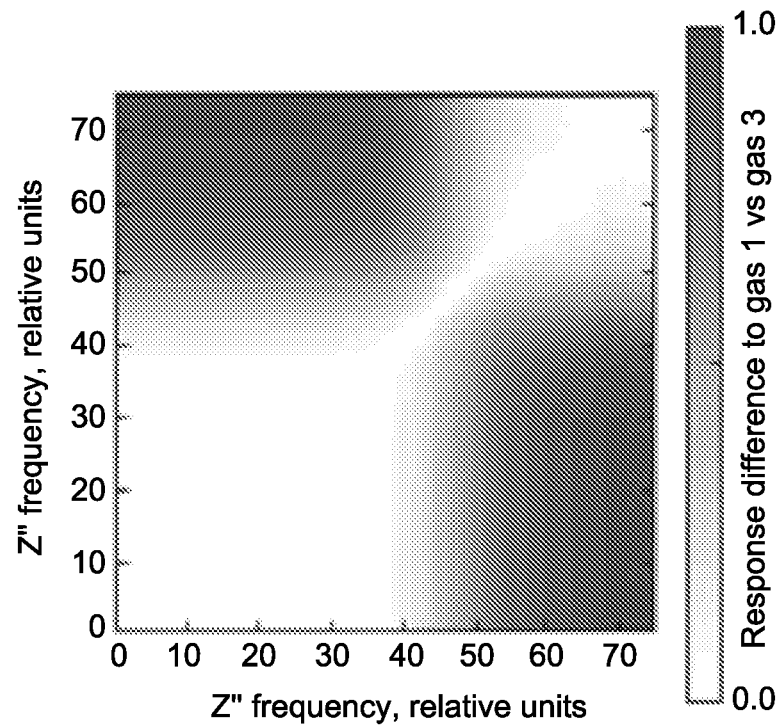
FIG. 53 illustrates a correlation matrix of the sensor response to gas 1 in relation to the sensor response to gas 3.

FIG. 53 illustrates a correlation matrix that depicts the diversity of the sensor response at different frequencies to gas 1 in relation to the sensor response at different frequencies to gas 3. The map may visualize regions of response difference for pairs of frequencies. The significant response difference of the sensor between gas 1 vs gas 3 may be observed when the region of frequencies starting from about frequency 45 to about frequency 75 may be paired with the region of frequencies starting from about frequency 1 to about frequency 50.

Figure 54:
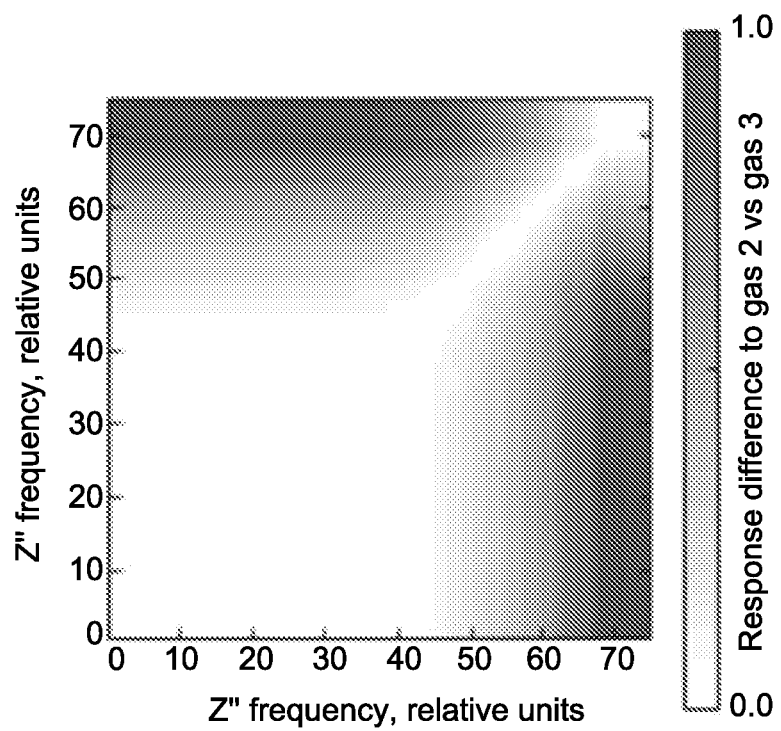
FIG. 54 illustrates a correlation matrix of the sensor response to gas 2 in relation to the sensor response to gas 3.

FIG. 54 illustrates a correlation matrix that depicts the diversity of the sensor response at different frequencies to gas 2 in relation to the sensor response at different frequencies to gas 3. The map may visualize regions of response difference for pairs of frequencies. The significant response difference of the sensor between gas 2 vs gas 3 may be observed when the region of frequencies starting from about frequency 65 to about frequency 75 may be paired with the region of frequencies starting from about frequency 1 to about frequency 60.

These correlation matrices depicted in FIG. 52, FIG. 53, and FIG. 54 may demonstrate that the developed multivariable sensor may have diverse responses to gas 1, gas 2, and gas 3 over the broad range of frequencies. These diverse responses to gas 1, gas 2, and gas 3 may allow the discrimination between these gases with a single multivariable sensor.

Figure 55:
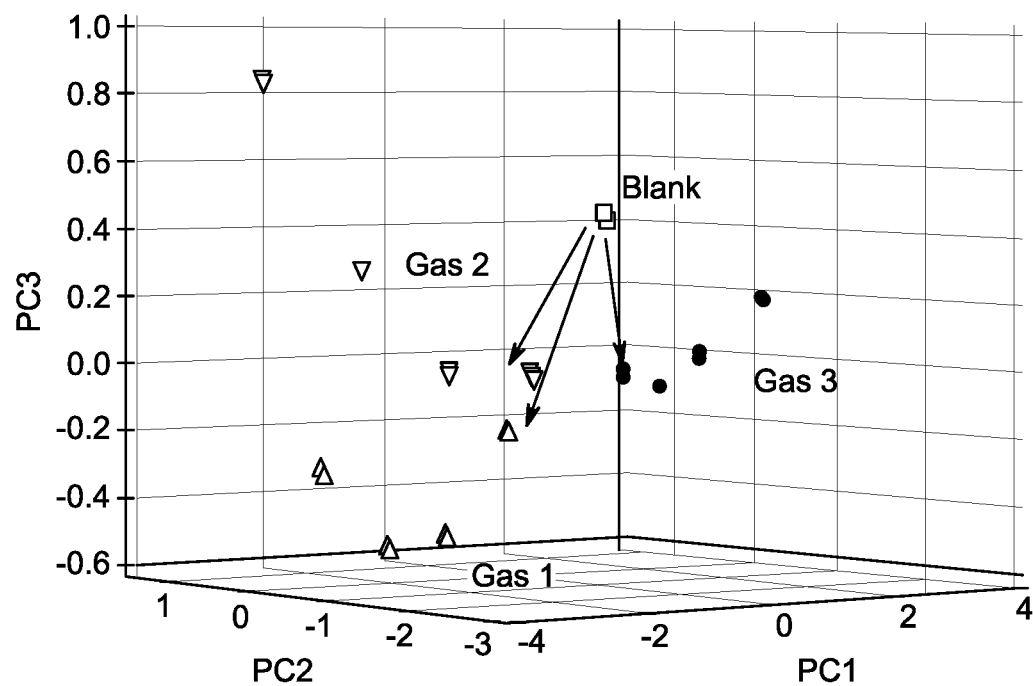
FIG. 55 depicts a scores plot of principal component 1 vs principal component 2 vs principal component 3 of the built principal component analysis model that discriminates between three individual gases such acetylene C2H2 (gas 1), hydrogen H2 (gas 2), and methane CH4 (gas 3) based on the Z' and Z" spectral features of a single multivariable sensor.

Several frequencies may be used to build multivariate models that enabled visualization of how the multivariate sensor responds to gas 1, gas 2, and gas 3. One multivariate model may be built using PCA. FIG. 55 illustrates a three-dimensional plot of a first principal component (PC1) versus a second principal component (PC2) and versus a third principal component (PC3). This score plot of PCs may visualize the response pattern of the sensor to gas 1, gas 2, and gas 3 based on their Z' and Z" spectral features. Acetylene $C_2H_2$ may be gas 1, hydrogen $H_2$ may be gas 2, and methane $CH_4$ may be gas 3. Such plot illustrates that PCA response of a single impedance sensor based on a $SnO_2$ sensing material starts from the response to a blank (clean air) and is further directed into different directions that may be dependent on the type of detected gas 1, gas 2, and gas 3. FIG. 55 illustrates that PCA response of a single impedance sensor based on a $SnO_2$ sensing material may have a high response dimensionality such as three dimensions. The higher the response dimensionality, the differentiation between the gases may improve relative to lower response dimensionality.

Figure 56:
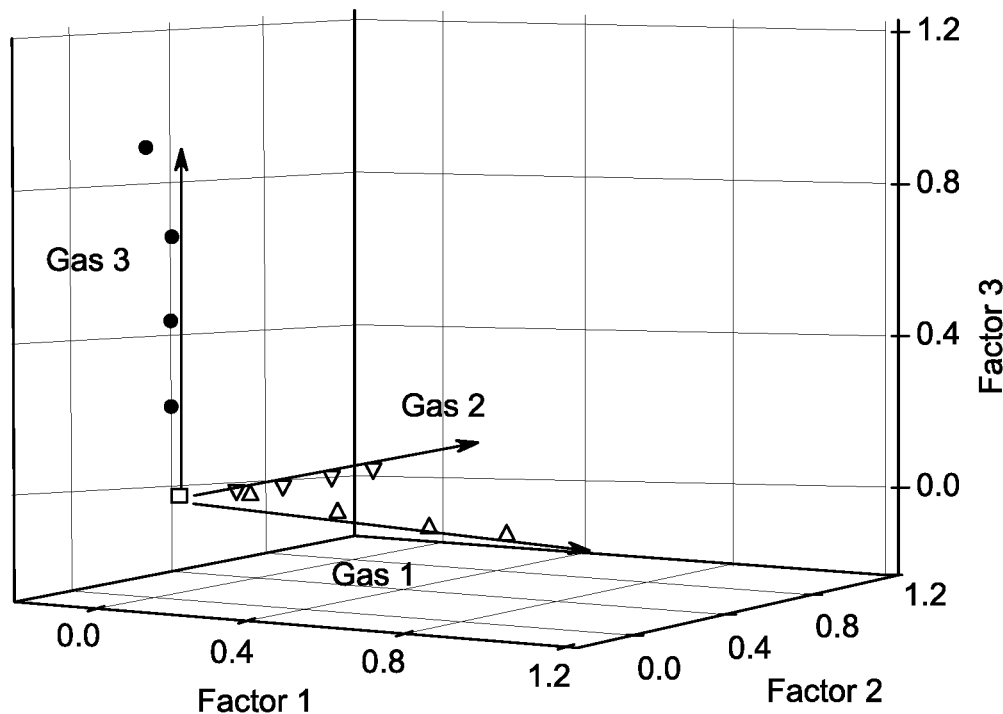
FIG. 56 depicts a plot of factor 1 vs factor 2 vs factor 3 of the built model that produces orthogonal response to three individual gases (gas 1 is acetylene C2H2, gas 2 is hydrogen H2, and methane CH4 is gas 3) with an improved linearity over PCA.

FIG. 56 depicts a plot of factor 1 versus factor 2 and versus factor 3 of another built model using a multivariate technique that may be different from PCA. This plot illustrates the ability to produce orthogonal response to different individual gases such as gas 1, gas 2, and gas 3 with an improved linearity over PCA.

In one embodiment, a method includes measuring an electrical response of a sensing material in a gas sensor probe assembly while the gas sensor probe assembly is in an OFF state, determining an aging effect of the gas sensor probe assembly based on the electrical response of the sensing material in the gas sensor probe assembly while the gas sensor probe assembly is in the OFF state, measuring an electrical response of the sensing material in the gas sensor probe assembly while the sensing material may be exposed to a fluid under examination and while the gas sensor probe assembly may be in an ON state, and correcting the electrical response of the sensing material in the gas sensor probe assembly that may be measured while the gas sensor probe assembly is in the ON state using the aging effect of the gas sensor probe assembly.

Optionally, the electrical response that may be measured while the gas sensor probe assembly is in the ON state represents an amount of at least one analyte gas that may be dissolved in an insulating oil of an electrical transformer.

Optionally, measuring the electrical response of the sensing material in the gas sensor probe assembly while the gas sensor probe assembly is in the OFF state may occur for a time period that may be at least ten times longer than measuring the electrical response of the sensing material in the gas sensor probe assembly while the sensing material is exposed to the insulating oil and while the gas sensor probe assembly is in the ON state.

Optionally, the electrical response that may be measured while the gas sensor probe assembly is in the ON state and that may be corrected using the aging effect quantifies an amount of one or more of hydrogen, carbon monoxide, or a hydrocarbon gas in the fluid under examination.

Optionally, the gas sensor probe assembly may measure the electrical response in the ON state by heating the sensing material and the gas sensor probe assembly may measure the electrical response in the OFF state by not heating the sensing material.

Optionally, the electrical response that may be measured while the gas sensor probe assembly is in the OFF state is an impedance response and the electrical response that may be measured while the gas sensor probe assembly is in the ON state is a resistance response.

Optionally, the electrical response that may be measured while the gas sensor probe assembly is in the OFF state may be a resistance response and the electrical response that may be measured while the gas sensor probe assembly is in the ON state is an impedance response.

Optionally, the electrical response that may be measured while the gas sensor probe assembly is in the OFF state and the electrical response that may be measured while the gas sensor probe assembly is in the ON state may be an impedance response.

Optionally, the electrical response that may be measured while the gas sensor probe assembly is in the OFF state and the electrical response that may be measured while the gas sensor probe assembly is in the ON state may be a resistance response.

Optionally, the electrical response of the gas probe sensor assembly may be measured while in the OFF state and the electrical response of the gas probe sensor assembly may be measured while in the ON state at different frequencies.

Optionally, correcting the electrical response that may be measured while the gas sensor probe assembly is in the ON state may use the aging effect of the gas sensor probe assembly and one or more transfer functions associated with one or more analytes of interest.

In one embodiment, a locomotive system may be provided that includes a platform, plural wheel-axle sets operably coupled to the platform, a reservoir attached to the platform and configured to hold a fluid, and a resonant sensor probe assembly coupled to the reservoir. The sensor probe assembly may include a substrate formed from one or more dielectric materials and free-standing electrodes coupled with the substrate. The free-standing electrodes may be placed into the fluid, to generate an electric field between the free-standing electrodes, and to measure an impedance response of the sensor to the fluid between the electrodes.

Optionally, the free-standing electrodes may not be directly mounted on the substrate. The free-standing electrodes may not be disposed within a footprint of the substrate. The free-standing electrodes may be configured to be placed into the fluid and to measure the impedance response of the sensor to the fluid without the substrate being placed into the fluid. The free-standing electrodes may include opposing planar plates positioned to receive at least some of the fluid between the plates. The free-standing electrodes can include an inner tube electrode disposed within and spaced apart from an outer tube electrode.

In one embodiment, a method for monitoring a health of equipment lubricant of a locomotive system may be provided. The method may include monitoring previous operational conditions of a locomotive engine of the locomotive system that operates using fuel and a lubricant, identifying one or more of an impurity content of the fuel supplied to the locomotive engine or an elapsed time since a previous addition of additional lubricant to the lubricant in the locomotive engine, and determining whether a change of the lubricant may be required prior to continued operation of the locomotive engine based on the previous operational conditions and the one or more of the impurity content of the fuel or the elapsed time since the previous addition of the additional lubricant to the lubricant in the locomotive engine.

Optionally, the method may include identifying the impurity content of the fuel and the impurity content may be an amount of sulfur in the fuel. The method may include both identifying the impurity content of the fuel and the elapsed time since the previous addition of the additional lubricant and determining whether the change of the lubricant may be required may be based on the previous operational conditions, the impurity content of the fuel, and the elapsed time since the previous addition of the additional lubricant. The previous operational conditions can include one or more of an elapsed operating time of the locomotive engine, an operating temperature of the locomotive engine, or an ambient temperature in which the locomotive engine operated.

The method also can include creating or updating a digital twin of the locomotive engine based on the previous operational conditions of the locomotive engine and forecasting upcoming operational conditions of the locomotive engine. Determining whether the change of the lubricant may be required prior to the continued operation of the locomotive engine can be based on the previous operational conditions, the one or more of the impurity content of the fuel or the elapsed time since the previous addition of the additional lubricant to the lubricant in the locomotive engine, the digital twin of the locomotive engine, and the upcoming operational conditions of the locomotive engine that are forecasted.

The method optionally can include changing the lubricant in the locomotive engine based on determining that the change in the lubricant may be required. Determining whether the change of the lubricant may be required can involve delaying the change of the lubricant beyond a previously scheduled maintenance of the locomotive engine that involves changing the lubricant.

In one embodiment, a locomotive system may include a platform, plural wheel-axle sets operably coupled to the platform, and a reservoir attached to the platform. The reservoir may be configured to hold a fluid. The locomotive system also can include a sensor probe assembly having a substrate formed from one or more dielectric materials and free-standing electrodes coupled with the substrate and configured to be placed into the fluid, to generate an electric field between the electrodes, and to measure an electric response of the sensor to the fluid between the electrodes. The locomotive system also may include a controller configured to determine the electric response of the sensor while the sensor may not be generating the electric field between the electrodes and to determine the electric response of the sensor while the sensor may be generating the electric field between the electrodes. The controller also may be configured to determine an aging effect of the sensor based on the electric response that may be measured while the sensor may not be generating the electric field between the electrodes. The controller may be configured to correct the electric response of the sensor that may be measured while the sensor may be generating the electric field between the electrodes using the aging effect that may be determined.

Optionally, the electric response that may be measured while the sensor may be generating the electric field between the electrodes represents an amount of at least one analyte gas that may be dissolved in an insulating oil of an electrical transformer onboard the platform. The sensor can be configured to measure the electric response of the sensor while the sensor may not be generating the electric field occurs for a time period that may be longer than the sensor measures the electric response while the sensor may not be generating the electric field between the electrodes. The sensor can be configured to measure the electric response while the sensor may be generating the electric field between the electrodes and that may be corrected using the aging effect quantifies an amount of one or more of hydrogen, carbon monoxide, or a hydrocarbon gas in the fluid.

The controller can be configured to direct one or more heating elements to heat the sensor while the sensor measures the electric response. The sensor can be configured to measure an impedance response of the sensor while the sensor may not be generating the electric field between the electrodes, and wherein the electrical response that is measured while the gas sensor probe assembly is in the ON state may be a resistance response. The sensor can be configured to measure the electric response while the sensor may not be generating the electric field between the electrodes as a resistance response of the sensor, and the sensor can be configured to measure the electric response while the sensor may be generating the electric field between the electrodes as an impedance response.

As used herein, the terms "module", "system," "device," "circuit," or "unit," may include a hardware and/or software system and circuitry that operates to perform one or more functions. For example, a module, unit, device, circuit, or system may include a computer processor, controller, or other logic-based device that performs operations based on instructions stored on a tangible and non-transitory computer readable storage medium, such as a computer memory. Alternatively, a module, unit, device, circuit, or system may include a hard-wired device that performs operations based on hard-wired logic and circuitry of the device. The modules, units, circuits, or systems shown in the attached figures may represent the hardware and circuitry that operates based on software or hardwired instructions, the software that directs hardware to perform the operations, or a combination thereof. The modules, systems, devices, circuits, or units can include or represent hardware circuits or circuitry that include and/or are connected with one or more processors, such as one or computer microprocessors.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

In one embodiment, the control system may have a local data collection system deployed that may use machine learning to enable derivation-based learning outcomes. The controller may learn from and make decisions on a set of data (including data provided by the various sensors), by making data-driven predictions and adapting according to the set of data. In embodiments, machine learning may involve performing a plurality of machine learning tasks by machine learning systems, such as supervised learning, unsupervised learning, and reinforcement learning. Supervised learning may include presenting a set of example inputs and desired outputs to the machine learning systems. Unsupervised learning may include the learning algorithm structuring its input by methods such as pattern detection and/or feature learning. Reinforcement learning may include the machine learning systems performing in a dynamic environment and then providing feedback about correct and incorrect decisions. In examples, machine learning may include a plurality of other tasks based on an output of the machine learning system. In examples, the tasks may be machine learning problems such as classification, regression, clustering, density estimation, dimensionality reduction, anomaly detection, and the like. In examples, machine learning may include a plurality of mathematical and statistical techniques. In examples, the many types of machine learning algorithms may include decision tree based learning, association rule learning, deep learning, artificial neural networks, genetic learning algorithms, inductive logic programming, support vector machines (SVMs), Bayesian network, reinforcement learning, representation learning, rule-based machine learning, sparse dictionary learning, similarity and metric learning, learning classifier systems (LCS), logistic regression, random forest, K-Means, gradient boost, K-nearest neighbors (KNN), a priori algorithms, and the like. In embodiments, certain machine learning algorithms may be used (e.g., for solving both constrained and unconstrained optimization problems that may be based on natural selection). In an example, the algorithm may be used to address problems of mixed integer programming, where some components restricted to being integer-valued. Algorithms and machine learning techniques and systems may be used in computational intelligence systems, computer vision, Natural Language Processing (NLP), recommender systems, reinforcement learning, building graphical models, and the like. In an example, machine learning may be used for vehicle performance and behavior analytics, and the like.

In one embodiment, the control system may include a policy engine that may apply one or more policies. These policies may be based at least in part on characteristics of a given item of equipment or environment. With respect to control policies, a neural network can receive input of a number of environmental and task-related parameters. These parameters may include an identification of a determined trip plan for a vehicle group, data from various sensors, and location and/or position data. The neural network can be trained to generate an output based on these inputs, with the output representing an action or sequence of actions that the vehicle group should take to accomplish the trip plan. During operation of one embodiment, a determination can occur by processing the inputs through the parameters of the neural network to generate a value at the output node designating that action as the desired action. This action may translate into a signal that causes the vehicle to operate. This may be accomplished via backpropagation, feed forward processes, closed loop feedback, or open loop feedback. Alternatively, rather than using backpropagation, the machine learning system of the controller may use evolution strategies techniques to tune various parameters of the artificial neural network. The controller may use neural network architectures with functions that may not always be solvable using backpropagation, for example functions that are non-convex. In one embodiment, the neural network has a set of parameters representing weights of its node connections. A number of copies of this network are generated and then different adjustments to the parameters are made, and simulations are done. Once the output from the various models are obtained, they may be evaluated on their performance using a determined success metric. The best model is selected, and the vehicle controller executes that plan to achieve the desired input data to mirror the predicted best outcome scenario. Additionally, the success metric may be a combination of the optimized outcomes, which may be weighed relative to each other.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, including the best mode, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general-purpose signal processor, microcontroller, random access memory, hard disk, or the like). Similarly, the programs may be stand alone programs, may be incorporated as subroutines in an operating system, may be functions in an installed software package, or the like. The various embodiments are not limited to the arrangements and instrumentality shown in the drawings.

As used herein, an element or step recited in the singular and proceeded with the word "a" or "an" should be understood as not excluding plural of said elements or operations, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "comprises," "including," "includes," "having," or "has" an element or a plurality of elements having a particular property may include additional such elements not having that property.

What is claimed is:

1. A resonant sensor probe assembly comprising:
   a dielectric substrate;
   free-standing electrodes coupled with the dielectric substrate; and
   a controller configured to control generation of an electric field between the free-standing electrodes and determine an impedance response of the resonant sensor probe assembly to a fluid between the free-standing electrodes responsive to generation of the electric field between the free-standing electrodes.

2. The resonant sensor probe assembly of claim 1, wherein the free-standing electrodes are not directly mounted on the dielectric substrate.

3. The resonant sensor probe assembly of claim 1, wherein the free-standing electrodes are not disposed within a footprint of the dielectric substrate.

4. The resonant sensor probe assembly of claim 1, wherein the free-standing electrodes are configured to be placed into the fluid and the controller is configured to measure the impedance response of the resonant sensor probe assembly to the fluid while the dielectric substrate is outside of the fluid.

5. The resonant sensor probe assembly of claim 1, wherein the free-standing electrodes include opposing planar plates positioned to receive at least some of the fluid between the opposing planar plates.

6. The resonant sensor probe assembly of claim 1, wherein the free-standing electrodes include an inner tube electrode disposed within and spaced apart from an outer tube electrode.

7. A method comprising:
   forming a substrate from one or more dielectric materials;
   coupling free-standing electrodes to the substrate;
   placing the free-standing electrodes into a fluid;
   generating an electric field between the free-standing electrodes; and
   measuring an impedance response of a sensor probe assembly to the fluid between the free-standing electrodes in response to the generation of the electric field between the free-standing electrodes.

8. The method of claim 7, further comprising positioning the free-standing electrodes such that the free-standing electrodes are not directly mounted on the substrate.

9. The method of claim 7, further comprising positioning the free-standing electrodes outside a footprint of the substrate.

10. The method of claim 7, further comprising placing the free-standing electrodes into the fluid and measuring the impedance response of the sensor probe assembly to the fluid while the substrate is outside of the fluid.

11. The method of claim 7, further comprising positioning opposing planar plates of the free-standing electrodes to receive at least some of the fluid between the opposing planar plates.

12. The method of claim 7, further comprising positioning an inner tube electrode of the free-standing electrodes within and spaced apart from an outer tube electrode.

13. A method comprising:
   forming a substrate from one or more dielectric materials;
   coupling free-standing electrodes to the substrate;
   placing the free-standing electrodes into a fluid;
   controlling generation of an electric field between the free-standing electrodes; and
   determining an impedance response of a sensor probe assembly to the fluid between the free-standing electrodes responsive to generation of the electric field between the free-standing electrodes.

14. The method of claim 13, further comprising positioning the free-standing electrodes such that the free-standing electrodes are not directly mounted on the substrate.

15. The method of claim 13, further comprising positioning the free-standing electrodes outside a footprint of the substrate.

16. The method of claim 13, further comprising placing the free-standing electrodes into the fluid and measuring the impedance response of the sensor probe assembly to the fluid while the substrate is outside of the fluid.

17. The method of claim 13, further comprising positioning opposing planar plates of the free-standing electrodes to receive at least some of the fluid between the opposing planar plates.

18. The method of claim 13, further comprising positioning an inner tube electrode of the free-standing electrodes within and spaced apart from an outer tube electrode.

19. The method of claim 13, further comprising measuring the impedance response while the sensor probe assembly is generating the electric field between the free-standing electrodes, the impedance response representing an amount of at least one analyte gas that is dissolved in an insulating oil of an electrical transformer.

20. The method of claim 13, further comprising measuring the impedance response while the sensor probe assembly is generating the electric field between the free-standing electrodes and correcting a measurement of the impedance response using an aging effect quantifies an amount of one or more of hydrogen, carbon monoxide, or a hydrocarbon gas in the fluid.

\* \* \* \* \*